(12) United States Patent
Tuch et al.

(10) Patent No.: US 10,870,889 B2
(45) Date of Patent: Dec. 22, 2020

(54) IMMUNOGLOBULIN EXPRESSION LEVELS AS BIOMARKER FOR PROTEASOME INHIBITOR RESPONSE

(71) Applicant: Onyx Therapeutics, Inc., South San Francisco, CA (US)

(72) Inventors: Brian Tuch, Brisbane, CA (US); Jeremiah Degenhardt, San Mateo, CA (US); Andrea Loehr, San Francisco, CA (US); Kevin Kwei, Mountain View, CA (US); Christopher J. Kirk, San Francisco, CA (US)

(73) Assignee: Onyx Therapeutics, Inc., Thousand Oaks, CA (US)

( * ) Notice: Subject to any disclaimer, the term of this patent is extended or adjusted under 35 U.S.C. 154(b) by 144 days.

(21) Appl. No.: 14/910,668

(22) PCT Filed: Aug. 8, 2014

(86) PCT No.: PCT/US2014/050333
§ 371 (c)(1),
(2) Date: Feb. 5, 2016

(87) PCT Pub. No.: WO2015/021376
PCT Pub. Date: Feb. 12, 2015

(65) Prior Publication Data
US 2016/0177402 A1    Jun. 23, 2016

Related U.S. Application Data

(60) Provisional application No. 62/005,904, filed on May 30, 2014, provisional application No. 61/875,954, filed on Sep. 10, 2013, provisional application No. 61/863,809, filed on Aug. 8, 2013.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57492* (2013.01); *C12Q 2600/106* (2013.01); *C12Q 2600/158* (2013.01); *G01N 2333/70535* (2013.01)

(58) Field of Classification Search
None
See application file for complete search history.

(56) References Cited

U.S. PATENT DOCUMENTS 8,278,038 B2 * 10/2012 Bryant ................ C12Q 1/6886
435/6.1
2006/0281122 A1    12/2006 Bryant et al.

2010/0099090 A1 *  4/2010 Tsuchihashi ......... C12Q 1/6809
435/7.24
2012/0015906 A1 *  1/2012 Shaughnessy, Jr. .........................
C12Q 1/6886
514/64
2016/0008382 A1 *  1/2016 Blakemore .......... G01N 33/574
514/19.3

FOREIGN PATENT DOCUMENTS

WO    WO 2013/071142    5/2013

OTHER PUBLICATIONS

The Free Dictionary definition for "measuring"; available via url: < thefreedictionary.com/measuring>, printed on Sep. 20, 2017.*
Fostier et al OncoTargets and Therapy. Sep. 27, 2012. 5:237-244.*
Caraguel et al., Selection of a cutoff value for real-time polymerase chain reaction results to fit a diagnostic purpose: analytical and epidemiologic approaches, J. Vet. Diagn. Invest., 23(1):2-15 (2011).
Dempster et al., Maximum likelihood from incomplete data via teh EM algorithm, J. Royal Statistical Soc. Series B, 39(1):1-38 (1977).
Flicek et al., Ensembl 2013, Nucleic Acids Res., 41(Database issue):D48-55 (2013).
Gray et al., Genenames.org: the HGNC resources in 2013, Nucleic Acids Res., 41(Database issue):D545-52 (2013).
Hajek et al., Design and rationale of FOCUS (PX-171-011): a randomized, open-label, phase 3 study of carfilzomib versus best supportive care regimen in patients with relapsed and refractory multiple myeloma (R/R MM), BMC Cancer, 12:415 (2012).
Hu et al., OSA: a fast and accurate alignment tool for RNA-Seq, Bioinformatics, 28(14):1933-4 (2012).
International Preliminary Report on Patentability, International Application No. PCT/US2014/050333, dated Feb. 9, 2016.
International Search Report and Written Opinion, International Application No. PCT/US2014/050333, dated Oct. 10, 2014.
Jiang et al., Biomarker-adaptive threshold design: a procedure for evaluating treatment with possible biomarker-defined subset effect, J. Natl. Cancer Inst., 99(13):1036-43 (2007).
Keats et al., Development of Methods to Perform Next Generation Sequencing (NGS)-Based Genomics Studies on Multiple Myeloma Clinical Samples, Blood, 122:5347 (2013).
Ling et al., Response of myeloma to teh proteasome inhibitor bortezomib is correlated with the unfolded protein response regulator XBP-1, Haematologica, 97(1):64-72 (2012).
Mackay et al., Real-time PCR in virology, Nucleic Acids Res., 30(6):1292-305 (2002).

(Continued)

*Primary Examiner* — Carla J Myers
(74) *Attorney, Agent, or Firm* — Marshall, Gerstein & Borun LLP

(57) ABSTRACT

Methods of treating a tumor in a subject and methods of determining a treatment regimen for a subject with a tumor are provided herein. In exemplary aspects, the methods comprise measuring the level of expression of immunoglobulin, FCGR2B, a gene listed in Table 4, or a combination thereof. In exemplary aspects, the subject is a subject from which a sample was obtained, wherein the level of immunoglobulin, FCGR2B, a gene listed in Table 4, or a combination thereof, has been measured from the sample. Related kits, computer readable-storage media, systems, and methods implemented by a processor in a computer are further provided.

13 Claims, 10 Drawing Sheets

Specification includes a Sequence Listing.

(56) References Cited

OTHER PUBLICATIONS

Meister et al., Extensive immunoglobulin production sensities myeloma cells for proteasome inhibition, Cancer Res., 67(4):1783-92 (2007).
Mulligan et al., Gene expression profiling and correlation with outcome in clinical trials of the proteasome inhibitor bortezomib, Blood, 109(8):3177-88 (2007).
Obeng et al., Proteasome inhibitors induce a terminal unfolded protein response in multiple myeloma cells, Blood, 107(12):4907-16 (2006).
Odell et al., Immunofluorescence techniques, J. Invest. Dermatol., 133(1):e4 (2013).
Rody et al., T-cell metagene predicts a favorable prognosis in estrogen receptor-negative and HER2-positive breast cancers, Breast Cancer Res., 11(2):R15 (2009).
Søreide, Receiver-operating characteristic curve analysis in diagnostic, prognostic and predictive biomarker research, J. Clin. Pathol., 62(1):1-5 (2009).
Tuch et al., Immunoglobulin expression is a major determinant of patient sensitivity to proteasome inhibitors, Blood, 122(21):1903 (2013).
Tuch et al., U.S. Appl. No. 61/863,809, "Immunoglobulin expression levels as biomarker for proteasome inhibitor", filed Sep. 2013.
Van de Donk et al., New developments in teh management and treatment of newly diagnosed and relapsed/refractory multiple myeloma patients, Exp. Opin. Pharmacotherapy, 14(12):1569-73 (2013).
Kawano et al., Multiple myeloma cells expressing low levels of CD138 have an immature phenotype and reduced sensitivity to lenalidomide, *Int. J. Oncol.* 41:876-84 (2012).
Vij et al., An open-label, single-arm, phase 2 study of single-agent carfilzomib in patients with relapsed and/or refractory multiple myeloma who have been previously treated with bortezomib, *Br. J. Haematol.* 158:739-48 (2012).

\* cited by examiner

IMMUNOGLOBULIN EXPRESSION LEVELS AS BIOMARKER FOR PROTEASOME INHIBITOR RESPONSE

CROSS REFERENCE TO RELATED APPLICATIONS

This application claims the priority benefit of Provisional U.S. Patent Application No. 61/863,809, filed on Aug. 8, 2013, Provisional U.S. Patent Application No. 61/875,954, filed on Sep. 10, 2013, and Provisional U.S. Patent Application No. 62/005,904, filed on May 30, 2014, each of which is incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 46,919,680 bytes ASCII (Text) file named "40058A_SeqListing.txt," created on Aug. 8, 2014."

TECHNICAL FIELD

This invention relates to the fields of molecular biology and cancer treatment. In some aspects, the invention relates to determining (e.g. predicting) a tumor's (e.g., a hematological tumor) sensitivity to treatment with a proteasome inhibitor. In some other aspects, the invention relates to methods useful for diagnosing, classifying, profiling, and treating cancer.

BACKGROUND

Multiple myeloma (MM) is an incurable malignancy that originates in the antibody-secreting bone marrow plasma cells. MM comprises approximately 10% of all hematologic malignancies. The progression of the tumor is well understood, and it can be diagnosed by the presence of multiple myeloma cells in the bone marrow and monitored by the amount of antibody secretion from the clonal population of plasma cells. With conventional treatment, median survival is approximately 3 to 4 years, but the clinical course is highly variable and difficult to predict. Several therapies for MM are now approved and many more are in development, promising improved outcomes for patients with this incurable cancer. With expanding treatment options, however, comes a pressing need to pair each patient with the most efficacious and safe treatment. With the narrow therapeutic index and the toxic potential of many available cancer therapies, such differential responses potentially contribute to patients undergoing unnecessary ineffective and even potentially harmful therapy regimens. If a designed therapy could be optimized to treat individual patients, such situations could be reduced or even eliminated. Furthermore, targeted designed therapy may provide more focused, successful patient therapy overall. Therefore, there is a need to better define patient-specific treatment strategies for the use of both standard and novel therapies.

Proteasome inhibition has emerged as an important strategy in cancer treatment, including in the treatment of multiple myeloma. By way of background, proteasomes are large, multienzyme complexes that play a key role in protein breakdown. The average human cell contains about 30,000 proteasomes, each of which contains several protein-digesting proteases. The proteasome mediates the proteasomal degradation pathway which is necessary to rid cells of excess and misfolded proteins. Proteasomal complexes help regulate a whole host of functions including transcription, viral infection, oncogenesis, cell cycle, stress response, ribosome biogenesis, abnormal protein catabolism, neural and muscular degeneration, antigen processing, DNA repair, and cellular differentiation. Proteasome activity is exquisitely controlled; when it becomes either overzealous (degrading more proteins than it should) or underachieving (neglecting to degrade certain proteins) disease can develop. Proteasome inhibitors (PIs), such as carfilzomib (marketed as Kyprolis® by Onyx Pharmaceuticals) and bortezomib (marketed as Velcade® by Millennium Pharmaceuticals), have become a standard therapy across all lines of MM therapy. Carfilzomib is a tetrapeptide epoxyketone, a selective proteasome inhibitor, and is approved for the treatment of patients with multiple myeloma who have already received at least two other treatments including bortezomib and an immunomodulatory agent (e.g., lenalidomide and/or thalidomide), and whose disease has progressed on their last therapy or within 60 days of their last therapy. Despite extensive study, the mechanism of selective tumor cell death following proteasome inhibition is poorly understood. Many patients have disease that does not respond to PIs, whereas others develop resistance, suggesting the need to better define patient-specific treatment strategies for the use of PI therapies.

SUMMARY

Provided herein are methods of treating a tumor in a subject. In exemplary embodiments, the method comprises (a) measuring the level of expression of (i) immunoglobulin (Ig), including gene or gene product, (ii) Fc gamma receptor 2B (FCGR2B), including gene or gene product, or (iii) both Ig and FCGR2B, in a sample obtained from the subject, wherein the sample comprises a cell from the tumor; and (b) administering to the subject an effective amount of a proteasome inhibitor, when the level of Ig expression and/or FCGR2B expression in the sample is greater than a reference level. When the level of Ig expression and/or FCGR2B expression in the sample is less than this reference level, then the patient is administered an alternative anti-tumor therapy that is not a proteasome inhibitor. In alternative or additional embodiments, the method comprises (a) measuring the level of expression of one or more genes or gene products listed in Table 4, in a sample obtained from the subject, wherein the sample comprises a cell from the tumor; and (b) administering to the subject an effective amount of a proteasome inhibitor, when (i) the level of expression of the one or more genes listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

In exemplary embodiments, the method comprises the step of administering to the subject an effective amount of a proteasome inhibitor. In exemplary aspects, the subject is a subject from which a sample was obtained and the level of expression of (i) immunoglobulin (Ig), (ii) Fc gamma receptor 2B (FCGR2B), or (iii) both Ig and FCGR2B, has been measured from the sample. In exemplary aspects, the proteasome inhibitor is administered, when the level of expression is greater than a reference level.

In alternative or additional aspects, the subject is a subject from which a sample was obtained and the level of expression of one or more genes or gene products listed in Table 4 has been measured from the sample. In exemplary aspects, the proteasome inhibitor is administered, when (i) the level of expression of the one or more genes or gene products listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

Also provided herein are methods of determining a treatment regimen for a subject with a tumor. In exemplary embodiments, the method comprises (a) measuring the level of expression of (i) immunoglobulin (Ig), (ii) Fc gamma receptor 2B (FCGR2B), or (iii) both Ig and FCGR2B, in a sample obtained from the subject, wherein the sample comprises a cell from the tumor, and (b) selecting a treatment regimen comprising administration of a proteasome inhibitor, when the level of Ig expression and/or FCGR2B expression in the sample is greater than a reference level. When the level of Ig expression and/or FCGR2B expression in the sample is less than this reference level, then the treatment regimen preferably includes administration of an alternative anti-tumor therapy that is not a proteasome inhibitor. In exemplary embodiments, the method comprises (a) measuring the level of expression of one or more genes or gene products listed in Table 4 in a sample obtained from the subject, wherein the sample comprises a cell from the tumor, and (b) selecting a treatment regimen comprising administration of a proteasome inhibitor, when (i) the level of expression of the one or more genes or gene products listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii). When (i) the level of expression of the one or more genes or gene products denoted in Table 4 as"up" is less than a reference level, or (ii) the level of expression of the one or more gene or gene products denoted in Table 4 as "down" is greater than a reference level, or both, then the treatment regimen preferably includes administration of an alternative anti-tumor therapy that is not a proteasome inhibitor.

Further provided herein are kits. In exemplary embodiments, the kit comprises one or more binding agents to an Ig gene or gene product, optionally an IgH, IgK or IgL gene segment or gene segment product, and a binding agent to FCGR2B gene or gene product. In exemplary embodiments, the kits comprises (i) one or more binding agents to an Ig gene or gene product, optionally an IgH, IgK or IgL gene segment or gene segment product, or a binding agent to FCGR2B gene or gene product and (ii) at least one binding agent to a gene or gene product listed in Table 4. In exemplary embodiments, the kit comprises at least a first binding agent and a second binding agent, wherein the first binding agent binds to a first gene or gene product encoded by a first gene listed in Table 4, wherein the second binding agent binds to a second gene or gene product encoded by a second gene listed in Table 4, wherein the first gene is different from the second gene.

Computer readable-storage media are furthermore provided herein. In exemplary embodiments, the computer readable storage medium is one having stored thereon a plurality of reference levels or ranges of reference levels, each reference level or range of reference levels corresponding to (i) an expression level of Ig or (ii) an expression level of FCGR2B, or (iii) an expression level of a gene listed in Table 4, or (iv) a combination thereof; and a data value that is an expression level of Ig and/or an expression level of FCGR2B and/or an expression level of a gene listed in Table 4, measured from a cell from a sample from a patient. In exemplary aspects, the the computer readable storage medium is one having stored thereon (I) a first set of data values and a second set of data values, wherein each data value of the first set is an expression level of Ig determined from a sample obtained from a responder and each data value of the second set is an expression level of Ig determined from a sample obtained from a non-responder; (II) a receiver operating characteristic (ROC) curve based on a first set of data values and a second set of data values, wherein each data value of the first set is an expression level of Ig determined from a sample obtained from a responder and each data value of the second set is an expression level of Ig determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

In exemplary embodiments, the computer readable storage medium is one having stored thereon (I) a first set of data values and a second set of data values, wherein each data value of the first set is an expression level of FCGR2B determined from a sample obtained from a responder and each data value of the second set is an expression level of FCGR2B deteremined from a sample obtained from a non-responder; (II) a receiver operating characteristic (ROC) curve based on a first set of data values and a second set of data values, wherein each data value of the first set is an expression level of FCGR2B determined from a sample obtained from a responder and each data value of the second set is an expression level of FCGR2B deteremined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

In exemplary embodiments, the computer readable storage medium is one having stored thereon (I) a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; (II) a receiver operating characteristic (ROC) curve based on a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a). In exemplary aspects, the computer readable storage medium comprises two or more of the foregoing media.

In exemplary embodiments, the computer readable storage medium is one having stored thereon machine-readable instructions executable by a processor, comprising: (a) instructions for receiving a data value, α, relating to a test level of Ig expression from a sample obtained from a test subject; and (b) instructions for displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, α, relating to a test level of FCGR2B expression from a sample obtained from a test subject; and (b) instructions for displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, α, relating to a test level of expression of a gene or gene product listed in Table 4 from a sample obtained from a test subject, wherein the change in gene expression level for the gene is denoted in Table 4 as "up"; and (b) instructions for displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, α, relating to a test level of expression of a gene or gene product listed in Table 4 from a sample obtained from a test subject, wherein the change in gene expression level for the gene is denoted in Table 4 as "down"; and (b) instructions for displaying an output relating to treating a patient for multiple myeloma with a proteasome inhibitor, when α is less than β, a cutoff correlative with a % specificity of at least 50% and a % sensitivity of at least 50%, as determined by a receiver operating characteristic (ROC) curve.

The invention additionally provides systems comprising: a processor; a memory device coupled to the processor, and machine readable instructions stored on the memory device. In exemplary embodiments, the machine readable instructions, when executed by the processor, cause the processor to: (i.) receive a data value, α, relating to a test level of Ig expression from a sample obtained from a test subject; and (ii) display an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of FCGR2B expression from a sample obtained from a test subject; and (ii) display an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of expression of a gene or gene product listed in Table 4, wherein the change in gene expression level for the gene is denoted in Table 4 as "up", from a sample obtained from a test subject; and (ii) display an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of expression of a gene or gene product listed in Table 4, wherein the change in gene expression level for the gene is denoted in Table 4 as "down", from a sample obtained from a test subject; and (ii) display an output relating to treating a patient for multiple myeloma with a proteasome inhibitor, when α is less than β, a cutoff correlative with a % specificity of at least 50% and a % sensitivity of at least 50%, as determined by a receiver operating characteristic (ROC) curve.

The invention further provides methods implemented by a processor in a computer. In exemplary embodiments, the method comprises the steps of: (a) receiving a data value, α, relating to a test level of Ig expression from a sample obtained from a test subject; and (b) displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of FCGR2B expression from a sample obtained from a test subject; and (b) displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of expression of a gene or gene product listed in Table 4 from a sample obtained from a test subject, wherein the change in gene expression level for the gene is denoted in Table 4 as "up"; and (b) displaying an output relating to treating a patient for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of expression of a gene or gene product listed in Table 4 from a sample obtained from a test subject, wherein the change in gene expression level for the gene is denoted in Table 4 as "down"; and (b) displaying an output relating to treating a patient for multiple myeloma with a proteasome inhibitor, when α is less than β, a cutoff correlative with a % specificity of at least 50% and a % sensitivity of at least 50%, as determined by a receiver operating characteristic (ROC) curve.

Other features and advantages of the invention will be apparent from the following detailed description and figures, and from the claims.

DETAILED DESCRIPTION

Methods of Treating a Tumor

Figure 1A:
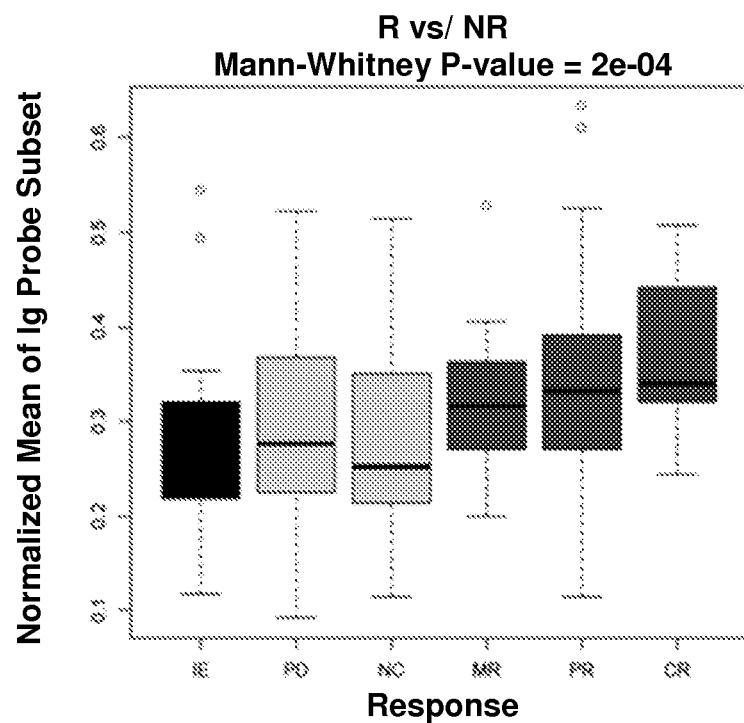
FIGS. 1A and 1B are graphs demonstrating the association between IG expression and bortezomib response. IE, response not evaluable; PD, progressive disease; no change, NC; minimal response, MR; partial response, PR; complete response, CR.

The invention provides methods of treating a tumor in a subject. In exemplary embodiments, the method comprises (a) measuring the level of expression of (i) immunoglobulin (Ig), including gene or gene product, (ii) Fc gamma receptor 2B (FCGR2B), including gene or gene product or (iii) both Ig and FCGR2B, in a sample obtained from the subject, wherein the sample comprises a cell from the tumor; and (b) administering to the subject an effective amount of a proteasome inhibitor when the level of Ig and/or FCGR2B expression in the sample is greater than a reference level.

In alternative or additional embodiments, the method comprises (a) measuring the level of expression of one or more genes or gene products listed in Table 4, in a sample obtained from the subject, wherein the sample comprises a cell from the tumor; and (b) administering to the subject an effective amount of a proteasome inhibitor, when (i) the level of expression of the one or more genes or gene products listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

The invention additional provides methods of treating a tumor in a subject, wherein the method comprises the step of administering to the subject an effective amount of a proteasome inhibitor and the subject is a subject from which a sample was obtained and the level of expression of (i) immunoglobulin (Ig), (ii) Fc gamma receptor 2B (FCGR2B), or (iii) both Ig and FCGR2B, has been measured from the sample. In exemplary aspects, the proteasome inhibitor is administered, when the level of expression is greater than a reference level.

In alternative or additional embodiments, the method of treating a tumor in a subject comprises the step of administering to the subject an effective amount of a proteasome inhibitor and the subject is a subject from which a sample was obtained and the level of expression of one or more genes or gene products listed in Table 4 has been measured from the sample. In exemplary aspects, the proteasome inhibitor is administered, when (i) the level of expression of the one or more genes listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

Methods of Determining a Treatment Regimen for a Subject with a Tumor

Also provided herein are methods of determining a treatment regimen for a subject with a tumor. In exemplary embodiments, the method comprises (a) measuring the level of expression of (i) immunoglobulin (Ig), (ii) Fc gamma receptor 2B (FCGR2B), or (iii) both Ig and FCGR2B, in a sample obtained from the subject, wherein the sample comprises a cell from the tumor, and (b) selecting a treatment regimen comprising administration of a proteasome inhibitor, when the level of Ig expression and/or FCGR2B expression in the sample is greater than a reference level. In additional or alternative embodiments, the method of determining a treatment regimen for a subject with a tumor comprises (a) measuring the level of expression of one or more genes or gene products listed in Table 4 in a sample obtained from the subject, wherein the sample comprises a cell from the tumor, and (b) selecting a treatment regimen comprising administration of a proteasome inhibitor, when (i) the level of expression of the one or more genes listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

Measurement of Expression Levels

In the methods of the invention, gene expression level(s) or gene segment expression level(s) is/are measured in a sample obtained from the subject. In exemplary aspects, the method comprises measuring the level, concentration, or amount of RNA, e.g., mRNA, encoded by the gene or gene segments in the sample. Levels of RNA, e.g., mRNA, may be measured by any technique known in the art, including but not limited to northern blotting or quantitative PCR (qPCR), including methods such as reverse transcription qPCR, real time qPCR, and end-point qPCR. Alternatively, "tag based" technologies, such as Serial analysis of gene expression (SAGE) and RNA-Seq, may be carried out to provide a relative measure of the cellular concentration of different mRNAs. Exemplary methods of measuring levels of RNA (e.g., mRNA) are also described herein at Example 5.

In alternative or additional aspects, the method comprises measuring the level, concentration, or amount of the protein product encoded by the gene or gene segments in the sample. Suitable methods of determining expression levels of protein products are known in the art and include immunoassays (e.g., Western blotting, an enzyme-linked immunosorbent assay (ELISA), a radioimmunoassay (RIA), and immunohistochemical assay. See, e.g., U.S. Patent Application Publication No. 2007/0212723 A1, Shang et al., *Circulation Research* 101: 1146-1154 (2007); and International Patent Application Publication Nos. WO/2012/094651 and WO/2010/129964. Exemplary methods of determining expression levels of protein products are also described herein at Example 6.

In alternative or additional aspects, the level of protein product is represented by a level of the protein product's biological activity, e.g., enzymatic activity. In exemplary aspects, the protein level is reflected by the levels of the substrate or product of the enzymatic reaction catalyzed by the protein product. Methods of assaying for the level of biological activity, e.g., enzymatic activity, are known in the art.

In some aspects, the level of the protein product is represented by the level of biological activity of a related protein, e.g., a protein which acts upstream or downstream of the protein product. For example, if the protein product is a phosphorylated protein in the active state, then, in some embodiments, the level of the protein product may be represented by the activity level of the kinase which phosphorylates the protein product. In other aspects, if the protein product is a transcription factor which activates expression of a gene, then, in some embodiments, the level of the protein product may be represented by the expression levels of the gene activated by the protein product.

In exemplary aspects, the expression level that is measured, may be normalized or calibrated to a level of a housekeeping gene. The housekeeping gene in some aspects is β-actin or GAPDH. In exemplary aspects, the housekeeping gene is any one of those set forth in the table below.

| Ensemble Gene ID | HGNC Gene ID |
|---|---|
| ENSG00000097007 | ABL1 |
| ENSG00000218739 | AC007390.5 |
| ENSG00000132842 | AP3B1 |
| ENSG00000065802 | ASB1 |
| ENSG00000108591 | DRG2 |
| ENSG00000181090 | EHMT1 |
| ENSG00000108262 | GIT1 |
| ENSG00000089022 | MAPKAPK5 |
| ENSG00000007047 | MARK4 |
| ENSG00000075975 | MKRN2 |
| ENSG00000198646 | NCOA6 |
| ENSG00000126653 | NSRP1 |
| ENSG00000107960 | OBFC1 |
| ENSG00000175470 | PPP2R2D |
| ENSG00000269277 | PPP2R2D |
| ENSG00000113456 | RAD1 |
| ENSG00000107185 | RGP1 |
| ENSG00000173456 | RNF26 |
| ENSG00000147164 | SNX12 |
| ENSG00000167182 | SP2 |
| ENSG00000110066 | SUV420H1 |
| ENSG00000149930 | TAOK2 |
| ENSG00000107021 | TBC1D13 |
| ENSG00000068354 | TBC1D25 |
| ENSG00000269499 | TBC1D25 |
| ENSG00000103671 | TRIP4 |
| ENSG00000130939 | UBE4B |
| ENSG00000170473 | WIBG |
| ENSG00000073050 | XRCC1 |
| ENSG00000121766 | ZCCHC17 |
| ENSG00000023041 | ZDHHC6 |

In exemplary aspects, the expression level that is measured, is not normalized or calibrated to a level of a housekeeping gene. In exemplary aspects, the expression level that is measured may represent an average expression level or a mean expression level based on more than one measurement of the expression level. In exemplary aspects, the measured expression level is an average or mean of several measurements of expression levels of the same sample. In exemplary aspects, the measured expression level is an average or mean of several measurements of expression levels of different samples containing the same components obtained from the same subject. In exemplary aspects, the measured expression level is quantile normalized, as is done in RNA Seq techniques.

Immunoglobulin (Ig)

In exemplary aspects, the sample obtained from the subject is measured for the expression level of immunoglobulins. Ig molecules comprise heavy chains and light chains, each of which have a constant region and a variable region. The genes encoding the segments of an Ig molecule are located at three loci within the human genome: the Ig heavy (IGH) locus, the Ig kappa (IGK) locus, and the Ig lambda (IGL) locus. The IGH locus is located on chromosome 14 (at ch. 14q32.33) and contains gene segments encoding Ig heavy chains. The IGK locus is located on chromosome 2 (at ch. 2p11.2) and contains gene segments encoding Ig light chains. The IGL locus is located on chromosome 22 (at ch. 22q11.2) and contains gene segments for Ig light chains. Each heavy chain and light chain gene contains multiple copies of different types of gene segments for the variable regions of the Ig molecule. For example, the immunoglobulin heavy chain region contains 44 Variable (V) gene segments[Matsuda et al., *J Expmtal Med* 188: 2151-2162 (1998)] plus 27 Diversity (D) gene segments and 6 Joining (J) gene segments. [Li et al., *Blood* 103: 4602-4609 (2004)]. Likewise, the light chain region possesses numerous V and J gene segments. However, light chain genes do not have D gene segments. DNA rearrangement causes one copy of each type of gene segment to be selected in any given lymphocyte, generating an enormous antibody repertoire; roughly $3 \times 10^{11}$ combinations are possible.

With regard to the inventive methods, when the sample obtained from the subject is measured for the expression level of immunoglobulins, the method may comprise measuring the expression level of any gene segment of the IGH locus, the IGK locus, or the IGL locus. In alternative or additional aspects, the method may comprise measuring the expression level of any IGH orphon gene segment which is not located at the IGH locus, any IGK orphon gene segment which is not located at the IGK locus, or any IGL orphon gene segment which is not located at the IGL locus. In exemplary aspects, the method comprises measuring the level of expression of one or more gene segments of the IGH locus, IGK locus, or IGL locus, or any IGH orphon gene segment, IGK orphon gene segment, or IGL orhon gene segment. In exemplary aspects, the method comprises measuring the level of expression of a combination of gene segments of at least two of the IGH locus, IGK locus, and IGL locus, or an orphon gene segment thereof. In exemplary aspects, the method comprises measuring the level of expression of a combination gene segments at each of the IGH locus, IGK locus, and IGL locus or at each of the IGH and IGK loci or at each of the IGH and IGL loci, or at each of the IGK and IGL loci. In alternative or additional aspects, the method comprises measuring the level of expression of a combination of IGH orphon gene segment(s), IGK orphon gene segment(s), and IGL orphon gene segment(s) or a combination of IGH orphon gene segments and IGK orphon gene segments or a combination of IGH orphon gene segments and IGL orphon gene segments or a combination of IGK orphon gene segments and IGL orphon gene segments.

In exemplary aspects, the method comprises measuring the level of expression of one or more gene segments at the IGH locus. In exemplary aspects, the one or more gene segments is selected from the group consisting of: IGHA1, IGHA2, IGHD, IGHD1-1, IGHD1-14, IGHD1-20, IGHD1-26, IGHD1-7, IGHD2-15, IGHD2-2, IGHD2-21, IGHD2-8, IGHD3-10, IGHD3-16, IGHD3-22, IGHD3-3, IGHD3-9, IGHD4-11, IGHD4-17, IGHD4-23, IGHD4-4, IGHD5-12, IGHD5-18, IGHD5-24, IGHD5-5, IGHD6-13, IGHD6-19, IGHD6-25, IGHD6-6, IGHD7-27, IGHE, IGHEP1, IGHEP2, IGHG1, IGHG2, IGHG3, IGHG4, IGHGP, IGHJ1, IGHJ1P, IGHJ2, IGHJ2P, IGHJ3, IGHJ3P, IGHJ4, IGHJ5, IGHJ6, IGHM, IGHMBP2, IGHV1-12, IGHV1-14, IGHV1-17, IGHV1-18, IGHV1-2, IGHV1-24, IGHV1-3, IGHV1-45, IGHV1-46, IGHV1-58, IGHV1-67, IGHV1-68, IGHV1-69, IGHV1-8, IGHV1OR21-1, IGHV2-10, IGHV2-26, IGHV2-5, IGHV2-70, IGHV2OR16-5, IGHV3-11, IGHV3-13, IGHV3-15, IGHV3-16, IGHV3-19, IGHV3-20, IGHV3-21, IGHV3-22, IGHV3-23, IGHV3-25, IGHV3-29, IGHV3-30, IGHV3-30-2, IGHV3-32, IGHV3-33, IGHV3-33-2, IGHV3-35, IGHV3-36, IGHV3-37, IGHV3-38, IGHV3-41, IGHV3-42, IGHV3-43, IGHV3-47, IGHV3-48, IGHV3-49, IGHV3-50, IGHV3-52, IGHV3-53, IGHV3-54, IGHV3-57, IGHV3-6, IGHV3-60, IGHV3-62, IGHV3-63, IGHV3-64, IGHV3-65, IGHV3-66, IGHV3-7, IGHV3-71, IGHV3-72, IGHV3-73, IGHV3-74, IGHV3-75, IGHV3-76, IGHV3-79, IGHV3-9, IGHV3OR16-8, IGHV4-28, IGHV4-31, IGHV4-34, IGHV4-39, IGHV4-4, IGHV4-55, IGHV4-59, IGHV4-61, IGHV4-80, IGHV5-51, IGHV5-78, IGHV6-1, IGHV7-27, IGHV7-34-1, IGHV7-40, IGHV7-56, IGHV7-81, IGHVII-1-1, IGHVII-15-1, IGHVII-20-1, IGHVII-22-1, IGHVII-26-2, IGHVII-28-1, IGHVII-30-1, IGHVII-31-1, IGHVII-33-1, IGHVII-40-1, IGHVII-43-1, IGHVII-44-2, IGHVII-46-1, IGHVII-49-1, IGHVII-51-2, IGHVII-53-1, IGHVII-60-1, IGHVII-62-1, IGHVII-65-1, IGHVII-67-1, IGHVII-74-1, IGHVII-78-1, IGHVIII-11-1, IGHVIII-13-1, IGHVIII-16-1, IGHVIII-2-1, IGHVIII-22-2, IGHVIII-25-1, IGHVIII-26-1, IGHVIII-38-1, IGHVIII-44, IGHVIII-47-1, IGHVIII-5-1, IGHVIII-51-1, IGHVIII-5-2, IGHVIII-67-2, IGHVIII-67-3, IGHVIII-67-4, IGHVIII-76-1, IGHVIII-82, and IGHVIV-44-1. In exemplary aspects, the one or more gene segments at the IgH locus comprises a sequence selected from the group consisting of SEQ ID NOs: 1-174. In exemplary aspects, the one or more gene segments at the IGH locus is one listed in the following table.

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5487 | IGHD1OR15-1A | immunoglobulin heavy diversity 1/OR15-1A (non-functional) | | IGHD1/OR15-1A, IGHD1OR151A | 15q11.2 | X55575 | | IGHO | "Immunoglobulins/ IGH orphons" |
| HGNC: 5488 | IGHD1OR15-1B | immunoglobulin heavy diversity 1/OR15-1B (non-functional) | | IGHD1/OR15-1B, IGHD1OR151B | 15q11.2 | X55576 | | IGHO | "Immunoglobulins/ IGH orphons" |
| HGNC: 5493 | IGHD2OR15-2A | immunoglobulin heavy diversity 2/OR15-2A (non-functional) | | IGHD2/OR15-2A, IGHD2OR152A | 15q11.2 | X55577 | | IGHO | "Immunoglobulins/ IGH orphons" |
| HGNC: 5494 | IGHD2OR15-2B | immunoglobulin heavy diversity 2/OR15-2B (non-functional) | | IGHD2/OR15-2B, IGHD2OR152B | 15q11.2 | X55578 | | IGHO | "Immunoglobulins/ IGH orphons" |
| HGNC: 5500 | IGHD3OR15-3A | immunoglobulin heavy diversity 3/OR15-3A (non-functional) | | IGHD3/OR15-3A, IGHD3OR153A | 15q11.2 | X55579 | | IGHO | "Immunoglobulins/ IGH orphons" |
| HGNC: 5501 | IGHD3OR15-3B | immunoglobulin heavy diversity 3/OR15-3B (non-functional) | | IGHD3/OR15-3B, IGHD3OR153B | 15q11.2 | X55580 | | IGHO | "Immunoglobulins/ IGH orphons" |

-continued

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5506 | IGHD4OR15-4A | immunoglobulin heavy diversity 4/OR15-4A (non-functional) | | IGHD4/OR15-4A, IGHD4OR154A | 15q11.2 | X55581 | | IGHO | "Immunoglobulins/ IGH orphons" |
| HGNC: 5507 | IGHD4OR15-4B | immunoglobulin heavy diversity 4/OR15-4B (non-functional) | | IGHD4/OR15-4B, IGHD4OR154B | 15q11.2 | X55582 | | IGHO | "Immunoglobulins/ IGH orphons" |
| HGNC: 5512 | IGHD5OR15-5A | immunoglobulin heavy diversity 5/OR15-5A (non-functional) | | IGHD5/OR15-5A, IGHD5OR155A | 15q11.2 | X55583 | | IGHO | "Immunoglobulins/ IGH orphons" |
| HGNC: 5513 | IGHD5OR15-5B | immunoglobulin heavy diversity 5/OR15-5B (non-functional) | | IGHD5/OR15-5B, IGHD5OR155B | 15q11.2 | X55584 | | IGHO | "Immunoglobulins/ IGH orphons" |
| HGNC: 5524 | IGHEP2 | immunoglobulin heavy constant epsilon P2 (pseudogene) | | | 9p24.1 | K01241 | NG_003254 | IGHO | "Immunoglobulins/ IGH orphons" |
| HGNC: 5563 | IGHV1OR15-1 | immunoglobulin heavy variable 1/OR15-1 (non-functional) | | IGHV1/OR15-1 | 15q11.2 | Z29631 | | IGHO | "Immunoglobulins/ IGH orphons" |
| HGNC: 5564 | IGHV1OR15-2 | immunoglobulin heavy variable 1/OR15-2 (pseudogene) | | IGHV1/OR15-2 | 15q11.1 | L25543 | | IGHO | "Immunoglobulins/ IGH orphons" |
| HGNC: 5565 | IGHV1OR15-3 | immunoglobulin heavy variable 1/OR15-3 (pseudogene) | | IGHV1/OR15-3 | 15q11.2 | Z29595 | | IGHO | "Immunoglobulins/ IGH orphons" |
| HGNC: 5566 | IGHV1OR15-4 | immunoglobulin heavy variable 1/OR15-4 (pseudogene) | | IGHV1/OR15-4 | 15q11.2 | Z29596 | | IGHO | "Immunoglobulins/ IGH orphons" |
| HGNC: 5567 | IGHV1OR15-5 | immunoglobulin heavy variable 1/OR15-5 (non-functional) | | IGHV1/OR15-5 | 15q11.2 | Z29633 | NG_016978 | IGHO | "Immunoglobulins/ IGH orphons" |
| HGNC: 5568 | IGHV1OR15-6 | immunoglobulin heavy variable 1/OR15-6 (pseudogene) | | IGHV1/OR15-6 | 15q11.2 | Z29634 | | IGHO | "Immunoglobulins/ IGH orphons" |
| HGNC: 5569 | IGHV1OR15-9 | immunoglobulin heavy variable 1/OR15-9 (non-functional) | VSIG7 | IGHV1/OR15-9, IGHV1OR159 | 15q11.1 | L25542 | | IGHO | "Immunoglobulins/ IGH orphons" |
| HGNC: 5570 | IGHV1OR16-1 | immunoglobulin heavy variable 1/OR16-1 (pseudogene) | | IGHV1/OR16-1 | 16p11.2 | Z29599 | | IGHO | "Immunoglobulins/ IGH orphons" |
| HGNC: 5571 | IGHV1OR16-2 | immunoglobulin heavy variable 1/OR16-2 (pseudogene) | | IGHV1/OR16-2 | 16p11.2 | Z29600 | | IGHO | "Immunoglobulins/ IGH orphons" |
| HGNC: 5572 | IGHV1OR16-3 | immunoglobulin heavy variable 1/OR16-3 (pseudogene) | | IGHV1/OR16-3 | 16p11.2 | Z29639 | | IGHO | "Immunoglobulins/ IGH orphons" |
| HGNC: 5573 | IGHV1OR16-4 | immunoglobulin heavy variable 1/OR16-4 (pseudogene) | | IGHV1/OR16-4 | 16p11.2 | Z17397 | | IGHO | "Immunoglobulins/ IGH orphons" |
| HGNC: 38040 | IGHV1OR21-1 | immunoglobulin heavy variable 1/OR21-1 (non-functional) | | IGHV1/OR21-1 | 21p11.2 | | NG_011680 | IGHO | "Immunoglobulins/ IGH orphons" |

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5579 | IGHV2OR16-5 | immunoglobulin heavy variable 2/OR16-5 (non-functional) | | IGHV2/OR16-5 | 16p11.2 | L25544 | | IGHO | "Immunoglobulins/ IGH orphons" |
| HGNC: 5633 | IGHV3OR15-7 | immunoglobulin heavy variable 3/OR15-7 (pseudogene) | | IGHV3/OR15-7 | 15q11.2 | Z29597 | | IGHO | "Immunoglobulins/ IGH orphons" |
| HGNC: 5641 | IGHV3OR16-6 | immunoglobulin heavy variable 3/OR16-6 (pseudogene) | | IGHV3/OR16-6 | 16p11.2 | L25545 | | IGHO | "Immunoglobulins/ IGH orphons" |
| HGNC: 5642 | IGHV3OR16-7 | immunoglobulin heavy variable 3/OR16-7 (pseudogene) | | IGHV3/OR16-7 | 16p11.2 | Z29604 | | IGHO | "Immunoglobulins/ IGH orphons" |
| HGNC: 5643 | IGHV3OR16-8 | immunoglobulin heavy variable 3/OR16-8 (non-functional) | | IGHV3/OR16-8 | 16p11.2 | Z29605 | | IGHO | "Immunoglobulins/ IGH orphons" |
| HGNC: 5644 | IGHV3OR16-9 | immunoglobulin heavy variable 3/OR16-9 (non-functional) | | IGHV3/OR16-9 | 16p11.2 | Z29606 | | IGHO | "Immunoglobulins/ IGH orphons" |
| HGNC: 5634 | IGHV3OR16-10 | immunoglobulin heavy variable 3/OR16-10 (non-functional) | | IGHV3/OR16-10 | 16p11.2 | Z29607 | | IGHO | "Immunoglobulins/ IGH orphons" |
| HGNC: 5635 | IGHV3OR16-11 | immunoglobulin heavy variable 3/OR16-11 (pseudogene) | | IGHV3/OR16-11 | 16p11.2 | Z29608 | | IGHO | "Immunoglobulins/ IGH orphons" |
| HGNC: 5636 | IGHV3OR16-12 | immunoglobulin heavy variable 3/OR16-12 (non-functional) | | IGHV3/OR16-12 | 16p11.2 | Z29609 | | IGHO | "Immunoglobulins/ IGH orphons" |
| HGNC: 5637 | IGHV3OR16-13 | immunoglobulin heavy variable 3/OR16-13 (non-functional) | | IGHV3/OR16-13 | 16p11.2 | Z29610 | NG_011771 | IGHO | "Immunoglobulins/ IGH orphons" |
| HGNC: 5638 | IGHV3OR16-14 | immunoglobulin heavy variable 3/OR16-14 (pseudogene) | | IGHV3/OR16-14 | 16p11.2 | Z29611 | | IGHO | "Immunoglobulins/ IGH orphons" |
| HGNC: 5639 | IGHV3OR16-15 | immunoglobulin heavy variable 3/OR16-15 (pseudogene) | | IGHV3/OR16-15 | 16p11.2 | L25546 | | IGHO | "Immunoglobulins/ IGH orphons" |
| HGNC: 5640 | IGHV3OR16-16 | immunoglobulin heavy variable 3/OR16-16 (pseudogene) | | IGHV3/OR16-16 | 16p11.2 | Z29613 | | IGHO | "Immunoglobulins/ IGH orphons" |
| HGNC: 5658 | IGHV4OR15-8 | immunoglobulin heavy variable 4/OR15-8 (non-functional) | VSIG6 | IGHV4/OR15-8, IGHV4OR158 | 15q11.2 | Z29598 | | IGHO | "Immunoglobulins/ IGH orphons" |

In exemplary aspects, the method comprises measuring the level of expression of one or more gene segments at the IGK locus. In exemplary aspects, the one or more gene segments is selected from the group consisting of: IGKC, IGKJ1, IGKJ2, IGKJ3, IGKJ4, IGKJ5, IGKV1-12, IGKV1-13, IGKV1-16, IGKV1-17, IGKV1-22, IGKV1-27, IGKV1-32, IGKV1-33, IGKV1-35, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-22, IGKV1D-27, IGKV1D-32, IGKV1D-33, IGKV1D-35, IGKV1D-37, IGKV1D-39, IGKV1D-42, IGKV1D-43, IGKV1D-8, IGKV1OR22-1, IGKV2-10, IGKV2-14, IGKV2-18, IGKV2-19, IGKV2-23, IGKV2-24, IGKV2-26, IGKV2-28, IGKV2-29, IGKV2-30, IGKV2-36, IGKV2-38, IGKV2-4, IGKV2-40, IGKV2D-10, IGKV2D-14, IGKV2D-18, IGKV2D-19, IGKV2D-23, IGKV2D-24, IGKV2D-26, IGKV2D-28, IGKV2D-29, IGKV2D-30, IGKV2D-36, IGKV2D-38, IGKV2D-40, IGKV2OR22-3, IGKV2OR22-4, IGKV3-11, IGKV3-15, IGKV3-20, IGKV3-25, IGKV3-31, IGKV3-34, IGKV3-7, IGKV3D-11, IGKV3D-15, IGKV3D-20, IGKV3D-25, IGKV3D-31, IGKV3D-34, IGKV3D-7, IGKV3OR22-2, IGKV4-1, IGKV5-2, IGKV6-21, IGKV6D-21, IGKV6D-41, IGKV7-3. In exemplary aspects, the one or more gene segments at the IgK locus comprises a sequence selected from the group consisting of SEQ ID NOs: 175-260. In exemplary aspects, the one or more gene segments at the IGK locus is one listed in the following table.

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5715 | IGK | immunoglobulin kappa locus | IGK@ | | 2p11.2 | | NG_000833 | IGK | "Immunoglobulins/ IGK locus" |
| HGNC: 5716 | IGKC | immunoglobulin kappa constant | | HCAK1 | 2p11.2 | J00241 | NG_000834 | IGK | "Immunoglobulins/ IGK locus" |
| HGNC: 5719 | IGKJ1 | immunoglobulin kappa joining 1 | | J1 | 2p11.2 | J00242 | NG_000834 | IGK | "Immunoglobulins/ IGK locus" |
| HGNC: 5720 | IGKJ2 | immunoglobulin kappa joining 2 | | J2 | 2p11.2 | J00242 | NG_000834 | IGK | "Immunoglobulins/ IGK locus" |
| HGNC: 5721 | IGKJ3 | immunoglobulin kappa joining 3 | | | 2p11.2 | J00242 | NG_000834 | IGK | "Immunoglobulins/ IGK locus" |
| HGNC: 5722 | IGKJ4 | immunoglobulin kappa joining 4 | | | 2p11.2 | J00242 | NG_000834 | IGK | "Immunoglobulins/ IGK locus" |
| HGNC: 5723 | IGKJ5 | immunoglobulin kappa joining 5 | | | 2p11.2 | J00242 | NG_000834 | IGK | "Immunoglobulins/ IGK locus" |
| HGNC: 5741 | IGKV1-5 | immunoglobulin kappa variable 1-5 | | | 2p11.2 | Z00001 | NG_000834 | IGK | "Immunoglobulins/ IGK locus" |
| HGNC: 5742 | IGKV1-6 | immunoglobulin kappa variable 1-6 | | | 2p11.2 | M64858 | NG_000834 | IGK | "Immunoglobulins/ IGK locus" |
| HGNC: 5743 | IGKV1-8 | immunoglobulin kappa variable 1-8 | | IGKV18, L9 | 2p11.2 | Z00014 | NG_000834 | IGK | "Immunoglobulins/ IGK locus" |
| HGNC: 5744 | IGKV1-9 | immunoglobulin kappa variable 1-9 | | IGKV19, L8 | 2p11.2 | Z00013 | NG_000834 | IGK | "Immunoglobulins/ IGK locus" |
| HGNC: 5730 | IGKV1-12 | immunoglobulin kappa variable 1-12 | | IGKV112, L19 | 2p11.2 | V01577 | NG_000834 | IGK | "Immunoglobulins/ IGK locus" |
| HGNC: 5731 | IGKV1-13 | immunoglobulin kappa variable 1-13 (gene/pseudogene) | | | 2p11.2 | Z00010 | NG_000834 | IGK | "Immunoglobulins/ IGK locus" |
| HGNC: 5732 | IGKV1-16 | immunoglobulin kappa variable 1-16 | | IGKV116, L1 | 2p11.2 | J00248 | NG_000834 | IGK | "Immunoglobulins/ IGK locus" |
| HGNC: 5733 | IGKV1-17 | immunoglobulin kappa variable 1-17 | | IGKV117, A30 | 2p11.2 | X72808 | NG_000834 | IGK | "Immunoglobulins/ IGK locus" |
| HGNC: 5734 | IGKV1-22 | immunoglobulin kappa variable 1-22 (pseudogene) | | | 2p11.2 | X71885 | NG_000834 | IGK | "Immunoglobulins/ IGK locus" |
| HGNC: 5735 | IGKV1-27 | immunoglobulin kappa variable 1-27 | | IGKV127, A20 | 2p11.2 | X63398 | NG_000834 | IGK | "Immunoglobulins/ IGK locus" |
| HGNC: 5736 | IGKV1-32 | immunoglobulin kappa variable 1-32 (pseudogene) | | | 2p11.2 | X71883 | NG_000834 | IGK | "Immunoglobulins/ IGK locus" |
| HGNC: 5737 | IGKV1-33 | immunoglobulin kappa variable 1-33 | | IGKV133, O18 | 2p11.2 | M64856 | NG_000834 | IGK | "Immunoglobulins/ IGK locus" |
| HGNC: 5738 | IGKV1-35 | immunoglobulin kappa variable 1-35 (pseudogene) | | | 2p11.2 | X71890 | NG_000834 | IGK | "Immunoglobulins/ IGK locus" |
| HGNC: 5739 | IGKV1-37 | immunoglobulin kappa variable 1-37 (non-functional) | | IGKV137, O14 | 2p11.2 | X59316 | NG_000834 | IGK | "Immunoglobulins/ IGK locus" |
| HGNC: 5740 | IGKV1-39 | immunoglobulin kappa variable 1-39 (gene/pseudogene) | | | 2p11.2 | X59315 | NG_000834 | IGK | "Immunoglobulins/ IGK locus" |
| HGNC: 5759 | IGKV1D-8 | immunoglobulin kappa variable 1D-8 | | | 2p11.2 | Z00008 | NG_000833 | IGK | "Immunoglobulins/ IGK locus" |
| HGNC: 5746 | IGKV1D-12 | immunoglobulin kappa variable 1D-12 | | | 2p11.2 | X17263 | NG_000833 | IGK | "Immunoglobulins/ IGK locus" |
| HGNC: 5747 | IGKV1D-13 | immunoglobulin kappa variable 1D-13 | | | 2p11.2 | X17262 | NG_000833 | IGK | "Immunoglobulins/ IGK locus" |
| HGNC: 5748 | IGKV1D-16 | immunoglobulin kappa variable 1D-16 | | | 2p11.2 | K01323 | NG_000833 | IGK | "Immunoglobulins/ IGK locus" |
| HGNC: 5749 | IGKV1D-17 | immunoglobulin kappa variable 1D-17 | | | 2p11.2 | X63392 | NG_000833 | IGK | "Immunoglobulins/ IGK locus" |
| HGNC: 5750 | IGKV1D-22 | immunoglobulin kappa variable 1D-22 (pseudogene) | | | 2p11.2 | X71887 | NG_000833 | IGK | "Immunoglobulins/ IGK locus" |

-continued

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5751 | IGKV1D-27 | immunoglobulin kappa variable 1D-27 (pseudogene) | | | 2p11.2 | Z00004 | NG_000833 | IGK | "Immunoglobulins/ IGK locus" |
| HGNC: 5752 | IGKV1D-32 | immunoglobulin kappa variable 1D-32 (pseudogene) | | | 2p11.2 | X71896 | NG_000833 | IGK | "Immunoglobulins/ IGK locus" |
| HGNC: 5753 | IGKV1D-33 | immunoglobulin kappa variable 1D-33 | | | 2p11.2 | M64855 | NG_000833 | IGK | "Immunoglobulins/ IGK locus" |
| HGNC: 5754 | IGKV1D-35 | immunoglobulin kappa variable 1D-35 (pseudogene) | | | 2p11.2 | X71894 | NG_000833 | IGK | "Immunoglobulins/ IGK locus" |
| HGNC: 5755 | IGKV1D-37 | immunoglobulin kappa variable 1D-37 (non-functional) | | IGKV1D37, O4 | 2p11.2 | X71893 | NG_000833 | IGK | "Immunoglobulins/ IGK locus" |
| HGNC: 5756 | IGKV1D-39 | immunoglobulin kappa variable 1D-39 | | | 2p11.2 | X59312 | NG_000833 | IGK | "Immunoglobulins/ IGK locus" |
| HGNC: 5757 | IGKV1D-42 | immunoglobulin kappa variable 1D-42 (non-functional) | | | 2p11.2 | X72816 | NG_000833 | IGK | "Immunoglobulins/ IGK locus" |
| HGNC: 5758 | IGKV1D-43 | immunoglobulin kappa variable 1D-43 | | | 2p11.2 | X72817 | NG_000833 | IGK | "Immunoglobulins/ IGK locus" |
| HGNC: 5788 | IGKV2-4 | immunoglobulin kappa variable 2-4 (pseudogene) | | | 2p11.2 | X72814 | NG_000834 | IGK | "Immunoglobulins/ IGK locus" |
| HGNC: 5776 | IGKV2-10 | immunoglobulin kappa variable 2-10 (pseudogene) | | | 2p11.2 | Z00012 | NG_000834 | IGK | "Immunoglobulins/ IGK locus" |
| HGNC: 5777 | IGKV2-14 | immunoglobulin kappa variable 2-14 (pseudogene) | | | 2p11.2 | X72810 | NG_000834 | IGK | "Immunoglobulins/ IGK locus" |
| HGNC: 5778 | IGKV2-18 | immunoglobulin kappa variable 2-18 (pseudogene) | | | 2p11.2 | X63400 | NG_000834 | IGK | "Immunoglobulins/ IGK locus" |
| HGNC: 5779 | IGKV2-19 | immunoglobulin kappa variable 2-19 (pseudogene) | | | 2p11.2 | X12692 | NG_000834 | IGK | "Immunoglobulins/ IGK locus" |
| HGNC: 5780 | IGKV2-23 | immunoglobulin kappa variable 2-23 (pseudogene) | | | 2p11.2 | X71885 | NG_000834 | IGK | "Immunoglobulins/ IGK locus" |
| HGNC: 5781 | IGKV2-24 | immunoglobulin kappa variable 2-24 | | | 2p11.2 | X12684 | NG_000834 | IGK | "Immunoglobulins/ IGK locus" |
| HGNC: 5782 | IGKV2-26 | immunoglobulin kappa variable 2-26 (pseudogene) | | | 2p11.2 | X71884 | NG_000834 | IGK | "Immunoglobulins/ IGK locus" |
| HGNC: 5783 | IGKV2-28 | immunoglobulin kappa variable 2-28 | | | 2p11.2 | X63397 | NG_000834 | IGK | "Immunoglobulins/ IGK locus" |
| HGNC: 5784 | IGKV2-29 | immunoglobulin kappa variable 2-29 (gene/pseudogene) | | | 2p11.2 | X63396 | NG_000834 | IGK | "Immunoglobulins/ IGK locus" |
| HGNC: 5785 | IGKV2-30 | immunoglobulin kappa variable 2-30 | | | 2p11.2 | X63403 | NG_000834 | IGK | "Immunoglobulins/ IGK locus" |
| HGNC: 5786 | IGKV2-36 | immunoglobulin kappa variable 2-36 (pseudogene) | | | 2p11.2 | X71889 | NG_000834 | IGK | "Immunoglobulins/ IGK locus" |
| HGNC: 5787 | IGKV2-38 | immunoglobulin kappa variable 2-38 (pseudogene) | | | 2p11.2 | X71888 | NG_000834 | IGK | "Immunoglobulins/ IGK locus" |
| HGNC: 5789 | IGKV2-40 | immunoglobulin kappa variable 2-40 | | | 2p11.2 | X59314 | NG_000834 | IGK | "Immunoglobulins/ IGK locus" |

-continued

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5792 | IGKV2D-10 | immunoglobulin kappa variable 2D-10 (pseudogene) | | | 2p11.2 | X17265 | NG_000833 | IGK | "Immunoglobulins/ IGK locus" |
| HGNC: 5793 | IGKV2D-14 | immunoglobulin kappa variable 2D-14 (pseudogene) | | | 2p11.2 | X72811 | NG_000833 | IGK | "Immunoglobulins/ IGK locus" |
| HGNC: 5794 | IGKV2D-18 | immunoglobulin kappa variable 2D-18 (pseudogene) | | | 2p11.2 | X63395 | NG_000833 | IGK | "Immunoglobulins/ IGK locus" |
| HGNC: 5795 | IGKV2D-19 | immunoglobulin kappa variable 2D-19 (pseudogene) | | | 2p11.2 | X71882 | NG_000833 | IGK | "Immunoglobulins/ IGK locus" |
| HGNC: 5796 | IGKV2D-23 | immunoglobulin kappa variable 2D-23 (pseudogene) | | | 2p11.2 | X71887 | NG_000833 | IGK | "Immunoglobulins/ IGK locus" |
| HGNC: 5797 | IGKV2D-24 | immunoglobulin kappa variable 2D-24 (non-functional) | | | 2p11.2 | X63401 | NG_000833 | IGK | "Immunoglobulins/ IGK locus" |
| HGNC: 5798 | IGKV2D-26 | immunoglobulin kappa variable 2D-26 | | | 2p11.2 | X12689 | NG_000833 | IGK | "Immunoglobulins/ IGK locus" |
| HGNC: 5799 | IGKV2D-28 | immunoglobulin kappa variable 2D-28 | | | 2p11.2 | X12691 | NG_000833 | IGK | "Immunoglobulins/ IGK locus" |
| HGNC: 5800 | IGKV2D-29 | immunoglobulin kappa variable 2D-29 | | | 2p11.2 | M31952 | NG_000833 | IGK | "Immunoglobulins/ IGK locus" |
| HGNC: 5801 | IGKV2D-30 | immunoglobulin kappa variable 2D-30 | | | 2p11.2 | X63402 | NG_000833 | IGK | "Immunoglobulins/ IGK locus" |
| HGNC: 5802 | IGKV2D-36 | immunoglobulin kappa variable 2D-36 (pseudogene) | | | 2p11.2 | X71893 | NG_000833 | IGK | "Immunoglobulins/ IGK locus" |
| HGNC: 5803 | IGKV2D-38 | immunoglobulin kappa variable 2D-38 (pseudogene) | | | 2p11.2 | X71892 | NG_000833 | IGK | "Immunoglobulins/ IGK locus" |
| HGNC: 5804 | IGKV2D-40 | immunoglobulin kappa variable 2D-40 | | | 2p11.2 | X59311 | NG_000833 | IGK | "Immunoglobulins/ IGK locus" |
| HGNC: 5821 | IGKV3-7 | immunoglobulin kappa variable 3-7 (non-functional) | | | 2p11.2 | X02725 | NG_000834 | IGK | "Immunoglobulins/ IGK locus" |
| HGNC: 5815 | IGKV3-11 | immunoglobulin kappa variable 3-11 | | | 2p11.2 | X01668 | NG_000834 | IGK | "Immunoglobulins/ IGK locus" |
| HGNC: 5816 | IGKV3-15 | immunoglobulin kappa variable 3-15 | | | 2p11.2 | M23090 | NG_000834 | IGK | "Immunoglobulins/ IGK locus" |
| HGNC: 5817 | IGKV3-20 | immunoglobulin kappa variable 3-20 | | | 2p11.2 | X12686 | NG_000834 | IGK | "Immunoglobulins/ IGK locus" |
| HGNC: 5818 | IGKV3-25 | immunoglobulin kappa variable 3-25 (pseudogene) | | | 2p11.2 | X06583 | NG_000834 | IGK | "Immunoglobulins/ IGK locus" |
| HGNC: 5819 | IGKV3-31 | immunoglobulin kappa variable 3-31 (pseudogene) | | | 2p11.2 | X71883 | NG_000834 | IGK | "Immunoglobulins/ IGK locus" |
| HGNC: 5820 | IGKV3-34 | immunoglobulin kappa variable 3-34 (pseudogene) | | | 2p11.2 | X71891 | NG_000834 | IGK | "Immunoglobulins/ IGK locus" |
| HGNC: 5829 | IGKV3D-7 | immunoglobulin kappa variable 3D-7 | | | 2p11.2 | X72820 | NG_000833 | IGK | "Immunoglobulins/ IGK locus" |
| HGNC: 5823 | IGKV3D-11 | immunoglobulin kappa variable 3D-11 | | | 2p11.2 | X17264 | NG_000833 | IGK | "Immunoglobulins/ IGK locus" |

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5824 | IGKV3D-15 | immunoglobulin kappa variable 3D-15 (gene/pseudogene) | | | 2p11.2 | X72815 | NG_000833 | IGK | "Immunoglobulins/IGK locus" |
| HGNC: 5825 | IGKV3D-20 | immunoglobulin kappa variable 3D-20 | | | 2p11.2 | X12687 | NG_000833 | IGK | "Immunoglobulins/IGK locus" |
| HGNC: 5826 | IGKV3D-25 | immunoglobulin kappa variable 3D-25 (pseudogene) | | | 2p11.2 | X71886 | NG_000833 | IGK | "Immunoglobulins/IGK locus" |
| HGNC: 5827 | IGKV3D-31 | immunoglobulin kappa variable 3D-31 (pseudogene) | | | 2p11.2 | X71896 | NG_000833 | IGK | "Immunoglobulins/IGK locus" |
| HGNC: 5828 | IGKV3D-34 | immunoglobulin kappa variable 3D-34 (pseudogene) | | | 2p11.2 | X71895 | NG_000833 | IGK | "Immunoglobulins/IGK locus" |
| HGNC: 5834 | IGKV4-1 | immunoglobulin kappa variable 4-1 | | IGKV41, B3 | 2p11.2 | Z00023 | NG_000834 | IGK | "Immunoglobulins/IGK locus" |
| HGNC: 5835 | IGKV5-2 | immunoglobulin kappa variable 5-2 | | IGKV52, B2 | 2p11.2 | X02485 | NG_000834 | IGK | "Immunoglobulins/IGK locus" |
| HGNC: 5836 | IGKV6-21 | immunoglobulin kappa variable 6-21 (non-functional) | | IGKV621, A26 | 2p11.2 | X63399 | NG_000834 | IGK | "Immunoglobulins/IGK locus" |
| HGNC: 5837 | IGKV6D-21 | immunoglobulin kappa variable 6D-21 (non-functional) | | IGKV6D21, A10 | 2p11.2 | X12683 | NG_000833 | IGK | "Immunoglobulins/IGK locus" |
| HGNC: 5838 | IGKV6D-41 | immunoglobulin kappa variable 6D-41 (non-functional) | | | 2p11.2 | X12688 | NG_000833 | IGK | "Immunoglobulins/IGK locus" |
| HGNC: 5839 | IGKV7-3 | immunoglobulin kappa variable 7-3 (pseudogene) | | | 2p11.2 | X12682 | NG_000834 | IGK | "Immunoglobulins/IGK locus" |

In exemplary aspects, the method comprises measuring the level of expression of one or more gene segments at the IGL locus. In exemplary aspects, the one or more gene segments is selected from the group consisting of: IGLC1, IGLC2, IGLC3, IGLC4, IGLC5, IGLC6, IGLC7, IGL-COR22-1, IGLJ1, IGLJ2, IGLJ3, IGLJ4, IGLJ5, IGLJ6, IGLJ7, IGLL1, IGLL3, IGLON5, IGLV10-54, IGLV10-67, IGLV11-55, IGLV1-36, IGLV1-40, IGLV1-41, IGLV1-44, IGLV1-47, IGLV1-50, IGLV1-51, IGLV1-62, IGLV2-11, IGLV2-14, IGLV2-18, IGLV2-23, IGLV2-28, IGLV2-33, IGLV2-34, IGLV2-5, IGLV2-8, IGLV3-1, IGLV3-10, IGLV3-12, IGLV3-13, IGLV3-15, IGLV3-16, IGLV3-17, IGLV3-19, IGLV3-2, IGLV3-21, IGLV3-22, IGLV3-24, IGLV3-25, IGLV3-26, IGLV3-27, IGLV3-29, IGLV3-30, IGLV3-31, IGLV3-32, IGLV3-4, IGLV3-6, IGLV3-7, IGLV3-9, IGLV4-3, IGLV4-60, IGLV4-69, IGLV5-37, IGLV5-45, IGLV5-48, IGLV5-52, IGLV6-57, IGLV7-35, IGLV7-43, IGLV7-46, IGLV8-61, IGLV9-49, IGLVI-20, IGLVI-38, IGLVI-42, IGLVI-56, IGLVI-63, IGLVI-68, IGLVI-70, IGLVIV-53, IGLVIV-59, IGLVIV-64, IGLVIV-65, IGLVIV-66-1, IGLVV-58, IGLVV-66, IGLVVI-22-1, IGLVVI-25-1, and IGLVVII-41-1. In exemplary aspects, the one or more gene segments at the IgL locus comprises a sequence selected from the group consisting of SEQ ID NOs: 261-350. In exemplary aspects, the one or more gene segments at the IGL locus is one listed in the following table.

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5853 | IGL | immunoglobulin lambda locus | IGL@ | | 22q11.2 | | NG_000002 | IGL | "Immunoglobulins/IGL locus" |
| HGNC: 5855 | IGLC1 | immunoglobulin lambda constant 1 (Mcg marker) | IGLC | | 22q11.2 | J00252 | NG_000002 | IGL | "Immunoglobulins/IGL locus" |
| HGNC: 5856 | IGLC2 | immunoglobulin lambda constant 2 (Kern–Oz–marker) | IGLC | | 22q11.2 | J00253 | NG_000002 | IGL | "Immunoglobulins/IGL locus" |

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5857 | IGLC3 | immunoglobulin lambda constant 3 (Kern−Oz+ marker) | IGLC | | 22q11.2 | J00254 | NG_000002 | IGL | "Immunoglobulins/ IGL locus" |
| HGNC: 5858 | IGLC4 | immunoglobulin lambda constant 4 (pseudogene) | IGLC | | 22q11.2 | J03009 | NG_000002 | IGL | "Immunoglobulins/ IGL locus" |
| HGNC: 5859 | IGLC5 | immunoglobulin lambda constant 5 (pseudogene) | IGLC | | 22q11.2 | J03010 | NG_000002 | IGL | "Immunoglobulins/ IGL locus" |
| HGNC: 5860 | IGLC6 | immunoglobulin lambda constant 6 (Kern+Oz− marker, gene/pseudogene) | IGLC | | 22q11.2 | J03011 | NG_000002 | IGL | "Immunoglobulins/ IGL locus" |
| HGNC: 5861 | IGLC7 | immunoglobulin lambda constant 7 | | | 22q11.2 | X51755 | NG_000002 | IGL | "Immunoglobulins/ IGL locus" |
| HGNC: 5863 | IGLJ1 | immunoglobulin lambda joining 1 | | | 22q11.2 | X04457 | NG_000002 | IGL | "Immunoglobulins/ IGL locus" |
| HGNC: 5864 | IGLJ2 | immunoglobulin lambda joining 2 | | | 22q11.2 | M15641 | NG_000002 | IGL | "Immunoglobulins/ IGL locus" |
| HGNC: 5865 | IGLJ3 | immunoglobulin lambda joining 3 | | | 22q11.2 | M15642 | NG_000002 | IGL | "Immunoglobulins/ IGL locus" |
| HGNC: 5866 | IGLJ4 | immunoglobulin lambda joining 4 (non-functional) | | | 22q11.2 | X51755 | NG_000002 | IGL | "Immunoglobulins/ IGL locus" |
| HGNC: 5867 | IGLJ5 | immunoglobulin lambda joining 5 (non-functional) | | | 22q11.2 | X51755 | NG_000002 | IGL | "Immunoglobulins/ IGL locus" |
| HGNC: 5868 | IGLJ6 | immunoglobulin lambda joining 6 | | | 22q11.2 | M18338 | NG_000002 | IGL | "Immunoglobulins/ IGL locus" |
| HGNC: 5869 | IGLJ7 | immunoglobulin lambda joining 7 | | | 22q11.2 | X51755 | NG_000002 | IGL | "Immunoglobulins/ IGL locus" |
| HGNC: 5876 | IGLV1-36 | immunoglobulin lambda variable 1-36 | | | 22q11.2 | Z73653 | NG_000002 | IGL | "Immunoglobulins/ IGL locus" |
| HGNC: 5877 | IGLV1-40 | immunoglobulin lambda variable 1-40 | | | 22q11.2 | M94116 | NG_000002 | IGL | "Immunoglobulins/ IGL locus" |
| HGNC: 5878 | IGLV1-41 | immunoglobulin lambda variable 1-41 (pseudogene) | | | 22q11.2 | M94118 | NG_000002 | IGL | "Immunoglobulins/ IGL locus" |
| HGNC: 5879 | IGLV1-44 | immunoglobulin lambda variable 1-44 | | | 22q11.2 | Z73654 | NG_000002 | IGL | "Immunoglobulins/ IGL locus" |
| HGNC: 5880 | IGLV1-47 | immunoglobulin lambda variable 1-47 | | | 22q11.2 | Z73663 | NG_000002 | IGL | "Immunoglobulins/ IGL locus" |
| HGNC: 5881 | IGLV1-50 | immunoglobulin lambda variable 1-50 (non-functional) | | | 22q11.2 | M94112 | NG_000002 | IGL | "Immunoglobulins/ IGL locus" |
| HGNC: 5882 | IGLV1-51 | immunoglobulin lambda variable 1-51 | | | 22q11.2 | Z73661 | NG_000002 | IGL | "Immunoglobulins/ IGL locus" |
| HGNC: 5883 | IGLV1-62 | immunoglobulin lambda variable 1-62 (pseudogene) | | | 22q11.2 | D87022 | NG_000002 | IGL | "Immunoglobulins/ IGL locus" |
| HGNC: 5894 | IGLV2-5 | immunoglobulin lambda variable 2-5 (pseudogene) | | | 22q11.2 | Z73641 | NG_000002 | IGL | "Immunoglobulins/ IGL locus" |
| HGNC: 5895 | IGLV2-8 | immunoglobulin lambda variable 2-8 | | | 22q11.2 | X97462 | NG_000002 | IGL | "Immunoglobulins/ IGL locus" |
| HGNC: 5887 | IGLV2-11 | immunoglobulin lambda variable 2-11 | | | 22q11.2 | Z73657 | NG_000002 | IGL | "Immunoglobulins/ IGL locus" |
| HGNC: 5888 | IGLV2-14 | immunoglobulin lambda variable 2-14 | | | 22q11.2 | Z73664 | NG_000002 | IGL | "Immunoglobulins/ IGL locus" |
| HGNC: 5889 | IGLV2-18 | immunoglobulin lambda variable 2-18 | | | 22q11.2 | Z73642 | NG_000002 | IGL | "Immunoglobulins/ IGL locus" |
| HGNC: 5890 | IGLV2-23 | immunoglobulin lambda variable 2-23 | | | 22q11.2 | X14616 | NG_000002 | IGL | "Immunoglobulins/ IGL locus" |

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5891 | IGLV2-28 | immunoglobulin lambda variable 2-28 (pseudogene) | | | 22q11.2 | X97466 | NG_000002 | IGL | "Immunoglobulins/ IGL locus" |
| HGNC: 5892 | IGLV2-33 | immunoglobulin lambda variable 2-33 (non-functional) | | | 22q11.2 | Z73643 | NG_000002 | IGL | "Immunoglobulins/ IGL locus" |
| HGNC: 5893 | IGLV2-34 | immunoglobulin lambda variable 2-34 (pseudogene) | | | 22q11.2 | D87013 | NG_000002 | IGL | "Immunoglobulins/ IGL locus" |
| HGNC: 5896 | IGLV3-1 | immunoglobulin lambda variable 3-1 | | | 22q11.2 | X57826 | NG_000002 | IGL | "Immunoglobulins/ IGL locus" |
| HGNC: 5904 | IGLV3-2 | immunoglobulin lambda variable 3-2 (pseudogene) | | | 22q11.2 | X97468 | NG_000002 | IGL | "Immunoglobulins/ IGL locus" |
| HGNC: 5915 | IGLV3-4 | immunoglobulin lambda variable 3-4 (pseudogene) | | | 22q11.2 | D87024 | NG_000002 | IGL | "Immunoglobulins/ IGL locus" |
| HGNC: 5916 | IGLV3-6 | immunoglobulin lambda variable 3-6 (pseudogene) | | | 22q11.2 | X97465 | NG_000002 | IGL | "Immunoglobulins/ IGL locus" |
| HGNC: 5917 | IGLV3-7 | immunoglobulin lambda variable 3-7 (pseudogene) | | | 22q11.2 | X97470 | NG_000002 | IGL | "Immunoglobulins/ IGL locus" |
| HGNC: 5918 | IGLV3-9 | immunoglobulin lambda variable 3-9 (gene/pseudogene) | | | 22q11.2 | X97473 | NG_000002 | IGL | "Immunoglobulins/ IGL locus" |
| HGNC: 5897 | IGLV3-10 | immunoglobulin lambda variable 3-10 | | | 22q11.2 | X97464 | NG_000002 | IGL | "Immunoglobulins/ IGL locus" |
| HGNC: 5898 | IGLV3-12 | immunoglobulin lambda variable 3-12 | | | 22q11.2 | Z73658 | NG_000002 | IGL | "Immunoglobulins/ IGL locus" |
| HGNC: 5899 | IGLV3-13 | immunoglobulin lambda variable 3-13 (pseudogene) | | | 22q11.2 | X97463 | NG_000002 | IGL | "Immunoglobulins/ IGL locus" |
| HGNC: 5900 | IGLV3-15 | immunoglobulin lambda variable 3-15 (pseudogene) | | | 22q11.2 | D87015 | NG_000002 | IGL | "Immunoglobulins/ IGL locus" |
| HGNC: 5901 | IGLV3-16 | immunoglobulin lambda variable 3-16 | | | 22q11.2 | X97471 | NG_000002 | IGL | "Immunoglobulins/ IGL locus" |
| HGNC: 5902 | IGLV3-17 | immunoglobulin lambda variable 3-17 (pseudogene) | | | 22q11.2 | X97472 | NG_000002 | IGL | "Immunoglobulins/ IGL locus" |
| HGNC: 5903 | IGLV3-19 | immunoglobulin lambda variable 3-19 | | | 22q11.2 | X56178 | NG_000002 | IGL | "Immunoglobulins/ IGL locus" |
| HGNC: 5905 | IGLV3-21 | immunoglobulin lambda variable 3-21 | | | 22q11.2 | X71966 | NG_000002 | IGL | "Immunoglobulins/ IGL locus" |
| HGNC: 5906 | IGLV3-22 | immunoglobulin lambda variable 3-22 (gene/pseudogene) | | | 22q11.2 | Z73666 | NG_000002 | IGL | "Immunoglobulins/ IGL locus" |
| HGNC: 5907 | IGLV3-24 | immunoglobulin lambda variable 3-24 (pseudogene) | | | 22q11.2 | X71968 | NG_000002 | IGL | "Immunoglobulins/ IGL locus" |
| HGNC: 5908 | IGLV3-25 | immunoglobulin lambda variable 3-25 | | | 22q11.2 | X97474 | NG_000002 | IGL | "Immunoglobulins/ IGL locus" |
| HGNC: 5909 | IGLV3-26 | immunoglobulin lambda variable 3-26 (pseudogene) | | | 22q11.2 | X97467 | NG_000002 | IGL | "Immunoglobulins/ IGL locus" |
| HGNC: 5910 | IGLV3-27 | immunoglobulin lambda variable 3-27 | | | 22q11.2 | D86994 | NG_000002 | IGL | "Immunoglobulins/ IGL locus" |
| HGNC: 5911 | IGLV3-29 | immunoglobulin lambda variable 3-29 (pseudogene) | | | 22q11.2 | Z73644 | NG_000002 | IGL | "Immunoglobulins/ IGL locus" |
| HGNC: 5912 | IGLV3-30 | immunoglobulin lambda variable 3-30 (pseudogene) | | | 22q11.2 | Z73646 | NG_000002 | IGL | "Immunoglobulins/ IGL locus" |

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5913 | IGLV3-31 | immunoglobulin lambda variable 3-31 (pseudogene) | | | 22q11.2 | X97469 | NG_000002 | IGL | "Immunoglobulins/ IGL locus" |
| HGNC: 5914 | IGLV3-32 | immunoglobulin lambda variable 3-32 (non-functional) | | | 22q11.2 | Z73645 | NG_000002 | IGL | "Immunoglobulins/ IGL locus" |
| HGNC: 5919 | IGLV4-3 | immunoglobulin lambda variable 4-3 | | | 22q11.2 | X57828 | NG_000002 | IGL | "Immunoglobulins/ IGL locus" |
| HGNC: 5920 | IGLV4-60 | immunoglobulin lambda variable 4-60 | | | 22q11.2 | Z73667 | NG_000002 | IGL | "Immunoglobulins/ IGL locus" |
| HGNC: 5921 | IGLV4-69 | immunoglobulin lambda variable 4-69 | | | 22q11.2 | Z73648 | NG_000002 | IGL | "Immunoglobulins/ IGL locus" |
| HGNC: 5922 | IGLV5-37 | immunoglobulin lambda variable 5-37 | | | 22q11.2 | Z73672 | NG_000002 | IGL | "Immunoglobulins/ IGL locus" |
| HGNC: 5923 | IGLV5-39 | immunoglobulin lambda variable 5-39 | | | 22q11.2 | Z73668 | | IGL | "Immunoglobulins/ IGL locus" |
| HGNC: 5924 | IGLV5-45 | immunoglobulin lambda variable 5-45 | | | 22q11.2 | Z73670 | NG_000002 | IGL | "Immunoglobulins/ IGL locus" |
| HGNC: 5925 | IGLV5-48 | immunoglobulin lambda variable 5-48 (non-functional) | | | 22q11.2 | Z73649 | NG_000002 | IGL | "Immunoglobulins/ IGL locus" |
| HGNC: 5926 | IGLV5-52 | immunoglobulin lambda variable 5-52 | | | 22q11.2 | Z73669 | NG_000002 | IGL | "Immunoglobulins/ IGL locus" |
| HGNC: 5927 | IGLV6-57 | immunoglobulin lambda variable 6-57 | | | 22q11.2 | Z73673 | NG_000002 | IGL | "Immunoglobulins/ IGL locus" |
| HGNC: 5928 | IGLV7-35 | immunoglobulin lambda variable 7-35 (pseudogene) | | | 22q11.2 | Z73660 | NG_000002 | IGL | "Immunoglobulins/ IGL locus" |
| HGNC: 5929 | IGLV7-43 | immunoglobulin lambda variable 7-43 | | | 22q11.2 | X14614 | NG_000002 | IGL | "Immunoglobulins/ IGL locus" |
| HGNC: 5930 | IGLV7-46 | immunoglobulin lambda variable 7-46 (gene/pseudogene) | | | 22q11.2 | Z73674 | NG_000002 | IGL | "Immunoglobulins/ IGL locus" |
| HGNC: 5931 | IGLV8-61 | immunoglobulin lambda variable 8-61 | | | 22q11.2 | Z73650 | NG_000002 | IGL | "Immunoglobulins/ IGL locus" |
| HGNC: 5933 | IGLV9-49 | immunoglobulin lambda variable 9-49 | | | 22q11.2 | Z73675 | NG_000002 | IGL | "Immunoglobulins/ IGL locus" |
| HGNC: 5884 | IGLV10-54 | immunoglobulin lambda variable 10-54 | | | 22q11.2 | Z73676 | NG_000002 | IGL | "Immunoglobulins/ IGL locus" |
| HGNC: 5885 | IGLV10-67 | immunoglobulin lambda variable 10-67 (pseudogene) | | | 22q11.2 | Z73651 | NG_000002 | IGL | "Immunoglobulins/ IGL locus" |
| HGNC: 5886 | IGLV11-55 | immunoglobulin lambda variable 11-55 (non-functional) | | | 22q11.2 | D86996 | NG_000002 | IGL | "Immunoglobulins/ IGL locus" |
| HGNC: 5934 | IGLVI-20 | immunoglobulin lambda variable (I)-20 (pseudogene) | | IGLV(I)-20 | 22q11.2 | D87007 | NG_000002 | IGL | "Immunoglobulins/ IGL locus" |
| HGNC: 5935 | IGLVI-38 | immunoglobulin lambda variable (I)-38 (pseudogene) | | IGLV(I)-38 | 22q11.2 | D87009 | NG_000002 | IGL | "Immunoglobulins/ IGL locus" |
| HGNC: 5936 | IGLVI-42 | immunoglobulin lambda variable (I)-42 (pseudogene) | | IGLV(I)-42 | 22q11.2 | X14613 | NG_000002 | IGL | "Immunoglobulins/ IGL locus" |

-continued

| HGNC ID | Approved Symbol | Approved Name | Previous Symbols | Synonyms | Chromosome | Accession Numbers | RefSeq IDs | Gene Family Tag | Gene family description |
|---|---|---|---|---|---|---|---|---|---|
| HGNC: 5937 | IGLVI-56 | immunoglobulin lambda variable (I)-56 (pseudogene) | | IGLV(I)-56 | 22q11.2 | D86996 | NG_000002 | IGL | "Immunoglobulins/ IGL locus" |
| HGNC: 5938 | IGLVI-63 | immunoglobulin lambda variable (I)-63 (pseudogene) | | IGLV(I)-63 | 22q11.2 | D87022 | NG_000002 | IGL | "Immunoglobulins/ IGL locus" |
| HGNC: 5939 | IGLVI-68 | immunoglobulin lambda variable (I)-68 (pseudogene) | | IGLV(I)-68 | 22q11.2 | D86993 | NG_000002 | IGL | "Immunoglobulins/ IGL locus" |
| HGNC: 5940 | IGLVI-70 | immunoglobulin lambda variable (I)-70 (pseudogene) | | IGLV(I)-70 | 22q11.2 | D86993 | NG_000002 | IGL | "Immunoglobulins/ IGL locus" |
| HGNC: 5941 | IGLVIV-53 | immunoglobulin lambda variable (IV)-53 (pseudogene) | | IGLV(IV)-53 | 22q11.2 | D86996 | NG_000002 | IGL | "Immunoglobulins/ IGL locus" |
| HGNC: 5942 | IGLVIV-59 | immunoglobulin lambda variable (IV)-59 (pseudogene) | | IGLV(IV)-59 | 22q11.2 | D87000 | NG_000002 | IGL | "Immunoglobulins/ IGL locus" |
| HGNC: 5943 | IGLVIV-64 | immunoglobulin lambda variable (IV)-64 (pseudogene) | | IGLV(IV)-64 | 22q11.2 | D87022 | NG_000002 | IGL | "Immunoglobulins/ IGL locus" |
| HGNC: 5944 | IGLVIV-65 | immunoglobulin lambda variable (IV)-65 (pseudogene) | | IGLV(IV)-65 | 22q11.2 | D87022 | NG_000002 | IGL | "Immunoglobulins/ IGL locus" |
| HGNC: 15692 | IGLVIV-66-1 | immunoglobulin lambda variable (IV)-66-1 (pseudogene) | | IGLV(IV)-66-1 | 22q11.2 | D87004 | NG_000002 | IGL | "Immunoglobulins/ IGL locus" |
| HGNC: 5945 | IGLVV-58 | immunoglobulin lambda variable (V)-58 (pseudogene) | | IGLV(V)-58 | 22q11.2 | D87000 | NG_000002 | IGL | "Immunoglobulins/ IGL locus" |
| HGNC: 5946 | IGLVV-66 | immunoglobulin lambda variable (V)-66 (pseudogene) | | IGLV(V)-66 | 22q11.2 | D87004 | NG_000002 | IGL | "Immunoglobulins/ IGL locus" |
| HGNC: 15689 | IGLVVI-22-1 | immunoglobulin lambda variable (VI)-22-1 (pseudogene) | | IGLV(VI)-22-1 | 22q11.2 | X71351 | NG_000002 | IGL | "Immunoglobulins/ IGL locus" |
| HGNC: 15690 | IGLVVI-25-1 | immunoglobulin lambda variable (VI)-25-1 (pseudogene) | | IGLV(VI)-25-1 | 22q11.2 | D86994 | NG_000002 | IGL | "Immunoglobulins/ IGL locus" |
| HGNC: 15691 | IGLVVII-41-1 | immunoglobulin lambda variable (VII)-41-1 (pseudogene) | | IGLV(VII)-41-1 | 22q11.2 | X99568 | NG_000002 | IGL | "Immunoglobulins/ IGL locus" |

In exemplary aspects, the method comprises measuring the expression of one or more IGH, IGK, or IGL orphon gene segments, and optionally, the one or more gene segments is one listed in the following table.

| HGNC ID | Approved Symbol | Approved Name | Previous Symbols | Synonyms | Chromosome |
|---|---|---|---|---|---|
| HGNC: 5487 | IGHD1OR15-1A | immunoglobulin heavy diversity 1/OR15-1A (non-functional) | | IGHD1/OR15-1A, IGHD1OR151A | 15q11.2 |

-continued

| | | | | |
|---|---|---|---|---|
| HGNC: 5488 | IGHD1OR15-1B | immunoglobulin heavy diversity 1/OR15-1B (non-functional) | IGHD1/OR15-1B, IGHD1OR151B | 15q11.2 |
| HGNC: 5493 | IGHD2OR15-2A | immunoglobulin heavy diversity 2/OR15-2A (non-functional) | IGHD2/OR15-2A, IGHD2OR152A | 15q11.2 |
| HGNC: 5494 | IGHD2OR15-2B | immunoglobulin heavy diversity 2/OR15-2B (non-functional) | IGHD2/OR15-2B, IGHD2OR152B | 15q11.2 |
| HGNC: 5500 | IGHD3OR15-3A | immunoglobulin heavy diversity 3/OR15-3A (non-functional) | IGHD3/OR15-3A, IGHD3OR153A | 15q11.2 |
| HGNC: 5501 | IGHD3OR15-3B | immunoglobulin heavy diversity 3/OR15-3B (non-functional) | IGHD3/OR15-3B, IGHD3OR153B | 15q11.2 |
| HGNC: 5506 | IGHD4OR15-4A | immunoglobulin heavy diversity 4/OR15-4A (non-functional) | IGHD4/OR15-4A, IGHD4OR154A | 15q11.2 |
| HGNC: 5507 | IGHD4OR15-4B | immunoglobulin heavy diversity 4/OR15-4B (non-functional) | IGHD4/OR15-4B, IGHD4OR154B | 15q11.2 |
| HGNC: 5512 | IGHD5OR15-5A | immunoglobulin heavy diversity 5/OR15-5A (non-functional) | IGHD5/OR15-5A, IGHD5OR155A | 15q11.2 |
| HGNC: 5513 | IGHD5OR15-5B | immunoglobulin heavy diversity 5/OR15-5B (non-functional) | IGHD5/OR15-5B, IGHD5OR155B | 15q11.2 |
| HGNC: 5524 | IGHEP2 | immunoglobulin heavy constant epsilon P2 (pseudogene) | | 9p24.1 |
| HGNC: 5563 | IGHV1OR15-1 | immunoglobulin heavy variable 1/OR15-1 (non-functional) | IGHV1/OR15-1 | 15q11.2 |
| HGNC: 5564 | IGHV1OR15-2 | immunoglobulin heavy variable 1/OR15-2 (pseudogene) | IGHV1/OR15-2 | 15q11.1 |
| HGNC: 5565 | IGHV1OR15-3 | immunoglobulin heavy variable 1/OR15-3 (pseudogene) | IGHV1/OR15-3 | 15q11.2 |
| HGNC: 5566 | IGHV1OR15-4 | immunoglobulin heavy variable 1/OR15-4 (pseudogene) | IGHV1/OR15-4 | 15q11.2 |

| | | | | | |
|---|---|---|---|---|---|
| HGNC: 5567 | IGHV1OR15-5 | immunoglobulin heavy variable 1/OR15-5 (non-functional) | | IGHV1/OR15-5 | 15q11.2 |
| HGNC: 5568 | IGHV1OR15-6 | immunoglobulin heavy variable 1/OR15-6 (pseudogene) | | IGHV1/OR15-6 | 15q11.2 |
| HGNC: 5569 | IGHV1OR15-9 | immunoglobulin heavy variable 1/OR15-9 (non-functional) | VSIG7 | IGHV1/OR15-9, IGHV1OR159 | 15q11.1 |
| HGNC: 5570 | IGHV1OR16-1 | immunoglobulin heavy variable 1/OR16-1 (pseudogene) | | IGHV1/OR16-1 | 16p11.2 |
| HGNC: 5571 | IGHV1OR16-2 | immunoglobulin heavy variable 1/OR16-2 (pseudogene) | | IGHV1/OR16-2 | 16p11.2 |
| HGNC: 5572 | IGHV1OR16-3 | immunoglobulin heavy variable 1/OR16-3 (pseudogene) | | IGHV1/OR16-3 | 16p11.2 |
| HGNC: 5573 | IGHV1OR16-4 | immunoglobulin heavy variable 1/OR16-4 (pseudogene) | | IGHV1/OR16-4 | 16p11.2 |
| HGNC: 38040 | IGHV1OR21-1 | immunoglobulin heavy variable 1/OR21-1 (non-functional) | | IGHV1/OR21-1 | 21p11.2 |
| HGNC: 5579 | IGHV2OR16-5 | immunoglobulin heavy variable 2/OR16-5 (non-functional) | | IGHV2/OR16-5 | 16p11.2 |
| HGNC: 5633 | IGHV3OR15-7 | immunoglobulin heavy variable 3/OR15-7 (pseudogene) | | IGHV3/OR15-7 | 15q11.2 |
| HGNC: 5641 | IGHV3OR16-6 | immunoglobulin heavy variable 3/OR16-6 (pseudogene) | | IGHV3/OR16-6 | 16p11.2 |
| HGNC: 5642 | IGHV3OR16-7 | immunoglobulin heavy variable 3/OR16-7 (pseudogene) | | IGHV3/OR16-7 | 16p11.2 |
| HGNC: 5643 | IGHV3OR16-8 | immunoglobulin heavy variable 3/OR16-8 (non-functional) | | IGHV3/OR16-8 | 16p11.2 |
| HGNC: 5644 | IGHV3OR16-9 | immunoglobulin heavy variable 3/OR16-9 (non-functional) | | IGHV3/OR16-9 | 16p11.2 |
| HGNC: 5634 | IGHV3OR16-10 | immunoglobulin heavy variable 3/OR16-10 (non-functional) | | IGHV3/OR16-10 | 16p11.2 |

| | | | | | |
|---|---|---|---|---|---|
| HGNC: 5635 | IGHV3OR16-11 | immunoglobulin heavy variable 3/OR16-11 (pseudogene) | | IGHV3/OR16-11 | 16p11.2 |
| HGNC: 5636 | IGHV3OR16-12 | immunoglobulin heavy variable 3/OR16-12 (non-functional) | | IGHV3/OR16-12 | 16p11.2 |
| HGNC: 5637 | IGHV3OR16-13 | immunoglobulin heavy variable 3/OR16-13 (non-functional) | | IGHV3/OR16-13 | 16p11.2 |
| HGNC: 5638 | IGHV3OR16-14 | immunoglobulin heavy variable 3/OR16-14 (pseudogene) | | IGHV3/OR16-14 | 16p11.2 |
| HGNC: 5639 | IGHV3OR16-15 | immunoglobulin heavy variable 3/OR16-15 (pseudogene) | | IGHV3/OR16-15 | 16p11.2 |
| HGNC: 5640 | IGHV3OR16-16 | immunoglobulin heavy variable 3/OR16-16 (pseudogene) | | IGHV3/OR16-16 | 16p11.2 |
| HGNC: 5658 | IGHV4OR15-8 | immunoglobulin heavy variable 4/OR15-8 (non-functional) | VSIG6 | IGHV4/OR15-8, IGHV4OR158 | 15q11.2 |
| HGNC: 5761 | IGKV1OR-2 | immunoglobulin kappa variable 1/OR-2 (pseudogene) | IGKVPZ2 | IGKV1/-2 | 9q21.11 |
| HGNC: 5762 | IGKV1OR-3 | immunoglobulin kappa variable 1/OR-3 (pseudogene) | IGKVPZ3 | IGKV1/-3 | 9q12 |
| HGNC: 5763 | IGKV1OR-4 | immunoglobulin kappa variable 1/OR-4 (pseudogene) | IGKVPZ4 | IGKV1/-4 | reserved |
| HGNC: 5764 | IGKV1OR1-1 | immunoglobulin kappa variable 1/OR1-1 (pseudogene) | IGKVP1 | IGKV1/OR1-1 | 1 |
| HGNC: 5766 | IGKV1OR2-0 | immunoglobulin kappa variable 1/OR2-0 (non-functional) | | IGKV1/OR2-0 | 2p11.2 |
| HGNC: 5760 | IGKV1OR2-1 | immunoglobulin kappa variable 1/OR2-1 (pseudogene) | IGKVPZ1, IGKV1OR-1 | IGKV1/OR-1, IGKV1/OR2-1 | 2p11.1 |
| HGNC: 5769 | IGKV1OR2-3 | immunoglobulin kappa variable 1/OR2-3 (pseudogene) | | IGKV1/OR2-3 | 2q11.2 |
| HGNC: 5770 | IGKV1OR2-6 | immunoglobulin kappa variable 1/OR2-6 (pseudogene) | | IGKV1/OR2-6 | 2q11.2 |
| HGNC: 5771 | IGKV1OR2-9 | immunoglobulin kappa variable 1/OR2-9 (pseudogene) | | IGKV1/OR2-9 | 2q11.2 |

-continued

| HGNC: 5768 | IGKV1OR2-11 | immunoglobulin kappa variable 1/OR2-11 (pseudogene) | | IGKV1/OR2-11 | 2q11.2 |
|---|---|---|---|---|---|
| HGNC: 5767 | IGKV1OR2-108 | immunoglobulin kappa variable 1/OR2-108 (non-functional) | | IGKV1/OR2-108, IGKV1OR2108, IGO1 | 2q12-q14 |
| HGNC: 37488 | IGKV1OR2-118 | immunoglobulin kappa variable 1/OR2-118 (pseudogene) | | IGKV1/OR2-118 | 2p11.1 |
| HGNC: 44978 | IGKV1OR10-1 | immunoglobulin kappa variable 1/OR10-1 (pseudogene) | | IGKV1/OR10-1 | 10q11.21 |
| HGNC: 5765 | IGKV1OR15-118 | immunoglobulin kappa variable 1/OR15-118 (pseudogene) | IGKVP2 | IGKV1/OR-118, IGKV1/OR15-118 | 15 |
| HGNC: 5772 | IGKV1OR22-1 | immunoglobulin kappa variable 1/OR22-1 (pseudogene) | IGKVP5 | IGKV1/OR22-1 | 22q11 |
| HGNC: 5773 | IGKV1OR22-5 | immunoglobulin kappa variable 1/OR22-5 (pseudogene) | IGKVP7, IGKV1OR22-5A | IGKV1/OR22-5, IGKV1/OR22-5A | 22q11 |
| HGNC: 37729 | IGKV1ORY-1 | immunoglobulin kappa variable 1/ORY-1 (pseudogene) | | IGKV1/ORY-1 | Yq11.21 |
| HGNC: 5805 | IGKV2OR2-1 | immunoglobulin kappa variable 2/OR2-1 (pseudogene) | IGKV2OR2-1A | IGKV2/OR2-1, IGKV2/OR2-1A | 2q11.2 |
| HGNC: 5808 | IGKV2OR2-2 | immunoglobulin kappa variable 2/OR2-2 (pseudogene) | | IGKV2/OR2-2 | 2q11.2 |
| HGNC: 5809 | IGKV2OR2-4 | immunoglobulin kappa variable 2/OR2-4 (pseudogene) | | IGKV2/OR2-4 | 2q11.2 |
| HGNC: 5810 | IGKV2OR2-7 | immunoglobulin kappa variable 2/OR2-7 (pseudogene) | | IGKV2/OR2-7 | 2q11.2 |
| HGNC: 37489 | IGKV2OR2-7D | immunoglobulin kappa variable 2/OR2-7D (pseudogene) | | IGKV2/OR2-7D | 2q11.2 |
| HGNC: 5811 | IGKV2OR2-8 | immunoglobulin kappa variable 2/OR2-8 (pseudogene) | | IGKV2/OR2-8 | 2q11.2 |
| HGNC: 5806 | IGKV2OR2-10 | immunoglobulin kappa variable 2/OR2-10 (pseudogene) | | IGKV2/OR2-10 | 2q11.2 |

| | | | | | |
|---|---|---|---|---|---|
| HGNC: 5812 | IGKV2OR22-3 | immunoglobulin kappa variable 2/OR22-3 (pseudogene) | IGKVP4 | IGKV2/OR22-3 | 22q11 |
| HGNC: 5813 | IGKV2OR22-4 | immunoglobulin kappa variable 2/OR22-4 (pseudogene) | IGKVP6 | IGKV2/OR22-4 | 22q11 |
| HGNC: 5832 | IGKV3OR2-5 | immunoglobulin kappa variable 3/OR2-5 (pseudogene) | | IGKV3/OR2-5 | 2q11.2 |
| HGNC: 5830 | IGKV3OR2-268 | immunoglobulin kappa variable 3/OR2-268 (non-functional) | IGKV268, IGKV3OR2-268A | IGKV3/OR2-268, IGKV3/OR2-268A | 2p12 |
| HGNC: 5833 | IGKV3OR22-2 | immunoglobulin kappa variable 3/OR22-2 (pseudogene) | IGKVP3 | IGKV3/OR22-2 | 22q11 |
| HGNC: 15696 | IGLCOR22-1 | immunoglobulin lambda constant/OR22-1 (pseudogene) | | IGLC/OR22-1 | 22q12.2-q12.3 |
| HGNC: 15697 | IGLCOR22-2 | immunoglobulin lambda constant/OR22-2 (pseudogene) | | IGLC/OR22-2 | 22q12.2-q12.3 |
| HGNC: 28614 | IGLJCOR18 | immunoglobulin lambda joining-constant/OR18 (pseudogene) | | IGLJ-COR18, IGLJ-C/OR18 | 18p11.31 |
| HGNC: 5932 | IGLV8OR8-1 | immunoglobulin lambda variable 8/OR8-1 (pseudogene) | | IGLV8/OR8-1 | 8q11.2 |
| HGNC: 15694 | IGLVIVOR22-1 | immunoglobulin lambda variable (IV)/OR22-1 (pseudogene) | | IGLV(IV)/OR22-1 | 22q11.2-q12.1 |
| HGNC: 15695 | IGLVIVOR22-2 | immunoglobulin lambda variable (IV)/OR22-2 (pseudogene) | | IGLV(IV)/OR22-2 | 22q12.2-q12.3 |

| HGNC ID | Accession Numbers | RefSeq IDs | Gene Family Tag | Gene family description |
|---|---|---|---|---|
| HGNC: 5487 | X55575 | | IGHO | "Immunoglobulins/IGH orphons" |
| HGNC: 5488 | X55576 | | IGHO | "Immunoglobulins/IGH orphons" |
| HGNC: 5493 | X55577 | | IGHO | "Immunoglobulins/IGH orphons" |
| HGNC: 5494 | X55578 | | IGHO | "Immunoglobulins/IGH orphons" |
| HGNC: 5500 | X55579 | | IGHO | "Immunoglobulins/IGH orphons" |
| HGNC: 5501 | X55580 | | IGHO | "Immunoglobulins/IGH orphons" |
| HGNC: 5506 | X55581 | | IGHO | "Immunoglobulins/IGH orphons" |
| HGNC: 5507 | X55582 | | IGHO | "Immunoglobulins/IGH orphons" |
| HGNC: 5512 | X55583 | | IGHO | "Immunoglobulins/IGH orphons" |
| HGNC: 5513 | X55584 | | IGHO | "Immunoglobulins/IGH orphons" |

| | | | | |
|---|---|---|---|---|
| HGNC: 5524 | K01241 | NG_003254 | IGHO | "Immunoglobulins/ IGH orphons" |
| HGNC: 5563 | Z29631 | | IGHO | "Immunoglobulins/ IGH orphons" |
| HGNC: 5564 | L25543 | | IGHO | "Immunoglobulins/ IGH orphons" |
| HGNC: 5565 | Z29595 | | IGHO | "Immunoglobulins/ IGH orphons" |
| HGNC: 5566 | Z29596 | | IGHO | "Immunoglobulins/ IGH orphons" |
| HGNC: 5567 | Z29633 | NG_016978 | IGHO | "Immunoglobulins/ IGH orphons" |
| HGNC: 5568 | Z29634 | | IGHO | "Immunoglobulins/ IGH orphons" |
| HGNC: 5569 | L25542 | | IGHO | "Immunoglobulins/ IGH orphons" |
| HGNC: 5570 | Z29599 | | IGHO | "Immunoglobulins/ IGH orphons" |
| HGNC: 5571 | Z29600 | | IGHO | "Immunoglobulins/ IGH orphons" |
| HGNC: 5572 | Z29639 | | IGHO | "Immunoglobulins/ IGH orphons" |
| HGNC: 5573 | Z17397 | | IGHO | "Immunoglobulins/ IGH orphons" |
| HGNC: 3804 | | NG_011680 | IGHO | "Immunoglobulins/ IGH orphons" |
| HGNC: 5579 | L25544 | | IGHO | "Immunoglobulins/ IGH orphons" |
| HGNC: 5633 | Z29597 | | IGHO | "Immunoglobulins/ IGH orphons" |
| HGNC: 5641 | L25545 | | IGHO | "Immunoglobulins/ IGH orphons" |
| HGNC: 5642 | Z29604 | | IGHO | "Immunoglobulins/ IGH orphons" |
| HGNC: 5643 | Z29605 | | IGHO | "Immunoglobulins/ IGH orphons" |
| HGNC: 5644 | Z29606 | | IGHO | "Immunoglobulins/ IGH orphons" |
| HGNC: 5634 | Z29607 | | IGHO | "Immunoglobulins/ IGH orphons" |
| HGNC: 5635 | Z29608 | | IGHO | "Immunoglobulins/ IGH orphons" |
| HGNC: 5636 | Z29609 | | IGHO | "Immunoglobulins/ IGH orphons" |
| HGNC: 5637 | Z29610 | NG_011771 | IGHO | "Immunoglobulins/ IGH orphons" |
| HGNC: 5638 | Z29611 | | IGHO | "Immunoglobulins/ IGH orphons" |
| HGNC: 5639 | L25546 | | IGHO | "Immunoglobulins/ IGH orphons" |
| HGNC: 5640 | Z29613 | | IGHO | "Immunoglobulins/ IGH orphons" |
| HGNC: 5658 | Z29598 | | IGHO | "Immunoglobulins/ IGH orphons" |
| HGNC: 5761 | X64640 | NG_011657 | IGKO | "Immunoglobulins/ IGK orphons" |
| HGNC: 5762 | X64641 | | IGKO | "Immunoglobulins/ IGK orphons" |
| HGNC: 5763 | X64642 | | IGKO | "Immunoglobulins/ IGK orphons" |
| HGNC: 5764 | M20809 | NG_011766 | IGKO | "Immunoglobulins/ IGK orphons" |
| HGNC: 5766 | Y08392 | | IGKO | "Immunoglobulins/ IGK orphons" |
| HGNC: 5760 | Z12367 | | IGKO | "Immunoglobulins/ IGK orphons" |
| HGNC: 5769 | X05102 | | IGKO | "Immunoglobulins/ IGK orphons" |
| HGNC: 5770 | X05103 | | IGKO | "Immunoglobulins/ IGK orphons" |
| HGNC: 5771 | X51879 | | IGKO | "Immunoglobulins/ IGK orphons" |
| HGNC: 5768 | X51885 | | IGKO | "Immunoglobulins/ IGK orphons" |
| HGNC: 5767 | X51887 | | IGKO | "Immunoglobulins/ IGK orphons" |
| HGNC: 37488 | | NG_011659 | IGKO | "Immunoglobulins/ IGK orphons" |

| | | | | |
|---|---|---|---|---|
| HGNC: 44978 | | | IGKO | "Immunoglobulins/IGK orphons" |
| HGNC: 5765 | | | IGKO | "Immunoglobulins/IGK orphons" |
| HGNC: 5772 | Z00040 | NG_011658 | IGKO | "Immunoglobulins/IGK orphons" |
| HGNC: 5773 | Z00003 | | IGKO | "Immunoglobulins/IGK orphons" |
| HGNC: 37729 | | | IGKO | "Immunoglobulins/IGK orphons" |
| HGNC: 5805 | X05101 | | IGKO | "Immunoglobulins/IGK orphons" |
| HGNC: 5808 | X51884 | | IGKO | "Immunoglobulins/IGK orphons" |
| HGNC: 5809 | X51883 | | IGKO | "Immunoglobulins/IGK orphons" |
| HGNC: 5810 | X51881 | NG_011671 | IGKO | "Immunoglobulins/IGK orphons" |
| HGNC: 37489 | X51881 | | IGKO | "Immunoglobulins/IGK orphons" |
| HGNC: 5811 | X51880 | NG_011662 | IGKO | "Immunoglobulins/IGK orphons" |
| HGNC: 5806 | X51886 | NG_011661 | IGKO | "Immunoglobulins/IGK orphons" |
| HGNC: 5812 | Z00041 | | IGKO | "Immunoglobulins/IGK orphons" |
| HGNC: 5813 | M20707 | | IGKO | "Immunoglobulins/IGK orphons" |
| HGNC: 5832 | X51882 | | IGKO | "Immunoglobulins/IGK orphons" |
| HGNC: 5830 | X74459 | | IGKO | "Immunoglobulins/IGK orphons" |
| HGNC: 5833 | Z00042 | | IGKO | "Immunoglobulins/IGK orphons" |
| HGNC: 15696 | AL008723 | | IGLO | "Immunoglobulins/IGL orphons" |
| HGNC: 15697 | AL021937 | | IGLO | "Immunoglobulins/IGL orphons" |
| HGNC: 28614 | J00255 | XM_497569 | IGLO | "Immunoglobulins/IGL orphons" |
| HGNC: 5932 | Y08831 | | IGLO | "Immunoglobulins/IGL orphons" |
| HGNC: 15694 | AL008721 | | IGLO | "Immunoglobulins/IGL orphons" |
| HGNC: 15695 | AL021937 | | IGLO | "Immunoglobulins/IGL orphons" |

In exemplary aspects of the inventive methods provided herein, the method comprises measuring the level of expression of all the gene segments at the IGH, IGK, and IGL loci and all the IGH orhpon gene segments, all the IGK orphon gene segments, and all the IGL orphon gene segments. In exemplary aspects, the level of expression is the sum of the expression levels of more than one gene segment of the IgH locus, IgK locus, and/or IgL locus. In exemplary aspects, the level of Ig expression is the sum of the expression levels of all the gene segments of the IgH locus and optionally all the IGH orphon gene segments. In exemplary aspects, the level of Ig expression is the sum of the expression levels of all the gene segments of the IgK locus and optionally all the IGK orphon gene segments. In exemplary aspects, the level of Ig expression is the sum of the expression levels of all the gene segments of the IgL locus and optionally all the IGL orphon gene segments. In exemplary aspects, the level of expression of Ig is the sum of (i) the levels of expression of all the gene segments of the IgH locus, (ii) the levels of expression of all the gene segments of the IgK locus, and (iii) the levels of expression of all the gene segments of the IgL locus, and optionally, all the IgH orphon gene segments, all the IgK orphon gene segments, and all the IgL orphon gene segments.

FCGR2B

In exemplary aspects, the sample obtained from the subject is measured for the expression level of FCGR2B. FCGR2B is also known as CD32 of the Fc fragmen of IgG, low affinity IIb, receptor. The gene encoding FCGR2B is located at ch. 1q23. Exemplary sequences encoding FCGR2B are provided herein as SEQ ID NO: 351 and 352, but are also known in the art. The FCGR2B gene is Entrez Gene No. 2213. The nucleotide sequence and amino acid sequence are available in the NCBI's nucleotide database as Accession No. NM_004001 and NP_003992.3 (SEQ ID NOs: 352-353, respectively).

Genes and Gene Segments of Table 4

In exemplary aspects, the sample obtained from the subject is measured for the expression level of one or more genes (or gene segments) listed in Table 4 set forth below. As used herein, the term "gene" refers to both a gene and gene segments. Table 4 includes, for each gene (or gene segment): (i) the HUGO gene symbol, if available, (ii) the Ensembl Gene Name, (iii) gene expression level data, and (iv) statistical data: the P-value and Q-value. The HUGO Gene Symbol is a name determined and approved by the HUGO Gene Nomenclature Committee (HGNC). The HGNC approves both a short-form abbreviation known as a gene symbol, and also a longer and more descriptive name.

Each gene symbol is unique and the HGNC ensures that each gene is only given one approved gene symbol. This unique gene symbol allows for clear and unambiguous reference to genes in scientific communications, and facilitates electronic data retrieval from databases and publications. Gene symbols also maintain parallel construction for different members of a gene family and can also be used for orthologous genes in other vertebrate species. A record for each gene symbol listed in Table 4 is accessible by the public via the HGNC database. The HGNC database is a curated online repository of HGNC-approved gene nomenclature, gene families, and associated resources including links to genomic, proteomic and phenotypic information. The HGNC database contains records for over 38,000 gene symbols is accessible to the public on the internet at http://www.genenames.org. The Ensemble Gene Name provided in Table 4 is the one listed in the HGNC database record for the indicated gene or gene segment. The Ensembl project produces genome databases for vertebrates and other eukaryotic species, and makes this information freely available on the internet at http://uswest.ensembl.org/index.html. When this Ensembl gene name or accession number is entered in the search window at the above web address, the sequence of the gene, as well as other structural information of the gene, may be accessed.

Reference Levels and Reference Values

In exemplary embodiments of the inventive methods, the expression level of the indicated gene(s) or gene segment(s) is/are compared to a reference level or reference value. As used herein, the term "reference level" is a cutoff or threshold against which the measured expression level is compared, which correlates with a pre-determined % specificity and/or pre-determined % sensitivity, as determined by a receiver operative characteristics (ROC) curve. In exemplary aspects, the ROC curve is based on the distribution of biomarker expression levels of a population of responders and the distribution of biomarker expression levels of a population of non-responders. In exemplary aspects, the reference level is a cutoff which correlates with X % specificity and Y % sensitivity, as determined by an ROC curve, wherein each of X and Y is selected from 25, 30, 35, 40, 45, 50, 55, 60, 65, 70, 75, 80, 85, 90, 91, 92, 93, 94, 95, 96, 97, 98, and 99.

In exemplary aspects, when the level of expression of an Ig is measured or has been measured, the reference level is a cutoff correlative with a pre-determined % specificity and/or pre-determined % sensitivity, as determined by a receiver operative characteristics (ROC) curve. In exemplary aspects, the ROC curve is based on the distribution of Ig expression levels of a population of responders and the distribution of Ig expression levels of a population of non-responders. Exemplary definitions of responders and non-responders are found herein at Example 2. In exemplary aspects, the reference level is the point on the ROC curve at which the % specificity is X %, wherein X is selected from 25, 30, 35, 40, 45, 50, 55, 60, 65, 70, 75, 80, 85, 90, 91, 92, 93, 94, 95, 96, 97, 98, and 99. In exemplary aspects, the reference level is the point on the ROC curve at which the % sensitivity is Y %, wherein Y is selected from 25, 30, 35, 40, 45, 50, 55, 60, 65, 70, 75, 80, 85, 90, 91, 92, 93, 94, 95, 96, 97, 98, and 99. In exemplary aspects, the reference level is a cut off correlative with a % specificity of at least 50% and a % sensitivity of at least 50%, as determined by the ROC curve. In exemplary aspects, the reference level is a cut off correlative with a % specificity of at least 75% and a % sensitivity of at least 75%, as determined by the ROC curve. In exemplary aspects, the reference level is a cut off correlative with a % specificity of at least 85% and a % sensitivity of at least 85%, as determined by the ROC curve. In exemplary aspects, the reference level is a cut off correlative with a % specificity of at least 90% and a % sensitivity of at least 90%, as determined by the ROC curve.

In exemplary aspects, when the level of expression of FCGR2B is measured or has been measured, the reference level is a cutoff correlative with a pre-determined % specificity and/or pre-determined % sensitivity, as determined by an ROC curve. In exemplary aspects, the ROC curve is based on the distribution of FCGR2B expression levels of a population of responders and the distribution of FCGR2B expression levels of a population of non-responders. Exemplary definitions of responders and non-responders are found herein at Example 2. In exemplary aspects, the reference level is the point on the ROC curve at which the % specificity is X %, wherein X is selected from 25, 30, 35, 40, 45, 50, 55, 60, 65, 70, 75, 80, 85, 90, 91, 92, 93, 94, 95, 96, 97, 98, and 99. In exemplary aspects, the reference level is the point on the ROC curve at which the % sensitivity is Y %, wherein Y is selected from 25, 30, 35, 40, 45, 50, 55, 60, 65, 70, 75, 80, 85, 90, 91, 92, 93, 94, 95, 96, 97, 98, and 99. In exemplary aspects, the reference level is a cut off correlative with a % specificity of at least 50% and a % sensitivity of at least 50%, as determined by the ROC curve. In exemplary aspects, the reference level is a cut off correlative with a % specificity of at least 75% and a % sensitivity of at least 75%, as determined by the ROC curve. In exemplary aspects, the reference level is a cut off correlative with a % specificity of at least 85% and a % sensitivity of at least 85%, as determined by the ROC curve. In exemplary aspects, the reference level is a cut off correlative with a % specificity of at least 90% and a % sensitivity of at least 90%, as determined by the ROC curve.

In exemplary aspects, when the level of expression of a gene or gene segment listed in Table 4 is measured or has been measured, the reference level is a cutoff correlative with a pre-determined % specificity and/or pre-determined % sensitivity, as determined by an ROC curve. In exemplary aspects, the ROC curve is based on the distribution of expression levels of the gene or gene segment listed in Table 4 of a population of responders and the distribution of expression levels of the a gene or gene segment listed in Table 4 of a population of non-responders. Exemplary definitions of responders and non-responders are found herein at Example 2. In exemplary aspects, the reference level is the point on the ROC curve at which the % specificity is X %, wherein X is selected from 25, 30, 35, 40, 45, 50, 55, 60, 65, 70, 75, 80, 85, 90, 91, 92, 93, 94, 95, 96, 97, 98, and 99. In exemplary aspects, the reference level is the point on the ROC curve at which the % sensitivity is Y %, wherein Y is selected from 25, 30, 35, 40, 45, 50, 55, 60, 65, 70, 75, 80, 85, 90, 91, 92, 93, 94, 95, 96, 97, 98, and 99. In exemplary aspects, the reference level is a cut off correlative with a % specificity of at least 50% and a % sensitivity of at least 50%, as determined by the ROC curve. In exemplary aspects, the reference level is a cut off correlative with a % specificity of at least 75% and a % sensitivity of at least 75%, as determined by the ROC curve. In exemplary aspects, the reference level is a cut off correlative with a % specificity of at least 85% and a % sensitivity of at least 85%, as determined by the ROC curve. In exemplary aspects, the reference level is a cut off correlative with a % specificity of at least 90% and a % sensitivity of at least 90%, as determined by the ROC curve.

In exemplary aspects, the expression level measured in the sample is above the reference level or reference value. In exemplary aspects, when the expression level measured in the sample is above the reference level or reference value and the expression level measured is that of an Ig, FCGR2B, or a gene or gene segment listed in Table 4 and labeled as having a change in gene expression level of "up", the method comprises administering to the subject an effective amount of a proteasome inhibitor or selecting a treatment regimen comprising administration of a proteasome inhibitor. In exemplary aspects, when the expression level measured in the sample is below the reference level or reference value and the expression level measured is that of an Ig, FCGR2B, or a gene or gene segment listed in Table 4 and labeled as having a change in gene expression level of "up", an effective amount of a proteasome inhibitor is not administered to the subject or a treatment regimen comprising administration of a proteasome inhibitor is not selected or a treatment regimen lacking administration of a proteasome inhibitor is selected.

In exemplary aspects, the expression level measured in the sample is below the reference level or reference value. In exemplary aspects, when the expression level measured in the sample is below the reference level or reference value and the expression level measured is that of a gene or gene segment listed in Table 4 and labeled as having a change in gene expression level of "down", the method comprises administering to the subject an effective amount of a proteasome inhibitor or selecting a treatment regimen comprising administration of a proteasome inhibitor. In exemplary aspects, when the expression level measured in the sample is above the reference level or reference value and the expression level measured is that of a gene or gene segment listed in Table 4 and labeled as having a change in gene expression level of "down", an effective amount of a proteasome inhibitor is not administered to the subject or a treatment regimen comprising administration of a proteasome inhibitor is not selected or a treatment regimen lacking administration of a proteasome inhibitor is selected.

In exemplary aspects, the expression level measured in the sample is greater than or above the reference level or reference value. The extent to which the measured expression level is above the reference level or reference value may be to any extent. In exemplary aspects, the measured expression level is at least or about 10% greater than the reference level (e.g., at least or about 15% greater than the reference level, at least or about 20% greater than the reference level, at least or about 25% greater than the reference level, at least or about 30% greater than the reference level, at least or about 35% greater than the reference level, at least or about 40% greater than the reference level, at least or about 45% greater than the reference level, at least or about 50% greater than the reference level, at least or about 55% greater than the reference level, at least or about 60% greater than the reference level, at least or about 65% greater than the reference level, at least or about 70% greater than the reference level, at least or about 75% greater than the reference level, at least or about 80% greater than the reference level, at least or about 85% greater than the reference level, at least or about 90% greater than the reference level, at least or about 95% greater than the reference level). In exemplary aspects, the measured expression level is at least 2-fold greater than the reference level, at least 3-fold greater than the reference level, at least 4-fold greater than the reference level, at least 5-fold greater than the reference level, at least 6-fold greater than the reference level, at least 7-fold greater than the reference level, at least 8-fold greater than the reference level, at least 9-fold greater than the reference level, or at least 10-fold greater than the reference level.

In exemplary aspects, the expression level measured in the sample is below or less than the reference level or reference value. The extent to which the measured expression level is below the reference level or reference value may be to any extent. In exemplary aspects, the measured expression level is at least or about 10% less than the reference level, at least or about 15% less than the reference level, at least or about 20% less than the reference level, at least or about 25% less than the reference level, at least or about 30% less than the reference level, at least or about 35% less than the reference level, at least or about 40% less than the reference level, at least or about 45% less than the reference level, at least or about 50% less than the reference level, at least or about 55% less than the reference level, at least or about 60% less than the reference level, at least or about 65% less than the reference level, at least or about 70% less than the reference level, at least or about 75% less than the reference level, at least or about 80% less than the reference level, at least or about 85% less than the reference level, at least or about 90% less than the reference level, at least or about 95% less than the reference level. In exemplary aspects, the measured expression level is at least 2-fold less than the reference level, at least 3-fold less than the reference level, at least 4-fold less than the reference level, at least 5-fold less than the reference level, at least 6-fold less than the reference level, at least 7-fold less than the reference level, at least 8-fold less than the reference level, at least 9-fold less than the reference level, or at least 10-fold less than the reference level.

In exemplary aspects, the reference level is normalized to a housekeeping gene, such as, the β-actin gene or GADPH gene. The levels may be normalized to another housekeeping gene, such as any of those described herein. In exemplary aspects, the reference level is not normalized to a housekeeping gene. In exemplary aspects, the reference level is normalized wherein the measured expression level is normalized or not normalized when the measured expression level is not normalized.

Responders and Non-Responders

As used herein, the term "responder" refers to one who has multiple myeloma, has been treated with the referenced drug, e.g., proteasome inhibitor, and has responded to treatment with the referenced drug, wherein response to treatment is as defined by the International Myeloma Working Group in Durie et al., "International uniform response criteria for multiple myeloma" *Leukemia, Volume* 20, No. 10, (2006). In exemplary aspects, a responder is one who has demonstrated a complete response (CR), a stringent complete response (sCR), a very good partial response (VGPR), or a partial response (PR). The definitions for a CR, sCR, VGPR, and PR are known in the art. See, Durie et al., 2006, supra. In exemplary aspects, a responder is one who has demonstrated a CR, sCR, VGPR, PR or a minimal response (MR). A response who has demonstrated an MR is one who has demonstrated at least a 25% decrease in paraprotein levels upon treatment.

As used herein, the term "non-responder" refers to one who has multiple myeloma, has been treated with the referenced drug, e.g., proteasome inhibitor, and has not responded to treatment with the reference drug, wherein response treatment is defined by the International Myeloma Working Group in Durie et al., 2006, supra. In exemplary aspects, a non-responder is one does not meet the criteria for a responder. In exemplary aspects, a non-responder is one who has demonstrated progressive disease (PD). In exemplary aspects, a non-responder is one who has demonstrated PD or stable disease (SD).

Additional Steps

In exemplary aspects, the method may include additional steps. For example, the method may include repeating one or more of the recited step(s) of the method. Accordingly, in exemplary aspects, the method comprises measuring the level of expression of Ig, FCGR2B, and/or one or more genes listed in Table 4 more than one time. In exemplary aspects, the method comprises measuring samples obtained from the subject every 6 to 12 months, wherein the measurement is based on a different biological sample obtained from the same subject.

In exemplary aspects, the method comprises measuring the sample for more than one expression level. For example, the method may comprise measuring the sample for Ig expression level and FCGR2B. In additional or alternative aspects, the method may comprise measuring the sample for at least one gene listed in Table 4. In exemplary aspects, the method may comprise measuring the sample for Ig expression and at least one gene listed in Table 4 or may comprise measuring the sample for FCGR2B expression and at least one gene listed in Table 4. In exemplary aspects, the method comprises measuring the expression level of more than one, more than two, more than three, more than four, more than five, more than six, more than seven, more than eight, more than nine, more than 10, more than 11, more than 12, more than 13, more than 14, more than 15, more than 16, more than 17, more than 18, more than 19, more than 20, more than 21, more than 22, more than 23, more than 24, more than 25, more than 26, more than 27, more than 28, more than 29, or more than 30 genes listed in Table 4. In exemplary aspects, the method comprises measuring the expression level of more than 100, more than 200, more than 300, more than 400 genes listed in Table 4. In exemplary aspects, the method comprises measuring the expression levels of all of the genes listed in Table 4.

In exemplary aspects, the method comprises measuring the RNA expression level of Ig, FCGR2B, or the one or more genes listed in Table 4, and comprises measuring the protein expression level of Ig, FCGR2B, or the one or more genes listed in Table 4.

In exemplary aspects, the subject's medical history is analyzed for expression levels of Ig, FCGR2B, and/or a gene or gene segment listed in Table 4.

In exemplary aspects, the method comprises sample preparation steps. For example, in some aspects, the method comprises selecting a specific cell population from the sample obtained from the subject. In exemplary aspects, the method comprises selecting for CD138-positive cells from the sample. The selection step may be carried out by any means known in the art, including, but not limited to FACS or chromatography. In exemplary aspects, wherein RNA expression levels are measured, the method may further comprise a step to extract or isolate the RNA from the cells of the sample. In exemplary aspects, the method comprises extracting RNA from CD138-positive tumor cells.

In exemplary aspects, wherein the method comprises measuring expression levels by measuring nucleic acids, e.g., RNA, mRNA, encoded by the Ig gene segment, the FCGR2B gene, and/or the gene listed in Table 4, the method further comprises amplifying at least a fragment of the nucleic acids to be measured. In exemplary aspects, the amplification is carried out via PCR or RT-PCR.

In exemplary aspects, the method comprises measuring the Ig expression level in the cell using a microarray platform that map to genes encoding Ig-related proteins. In exemplary aspects, the method comprises measuring the Ig protein load in the cells with an anti-human Ig antibody. In exemplary aspects, the measuring comprises measuring the presence, absence, or amount of a human Ig protein in the sample In exemplary aspects of the inventive methods of determining a treatment regimen for a subject with a tumor, the method may optionally include an administering step, wherein a therapeutic agent or device is administered to the subject, when the expression level of Ig, FCGR2B, and/or a gene or gene segment listed in Table 4 having a change in gene expression level denoted in Table 4 as "up" is increased. For example, the methods described herein may optionally comprise a step of providing an appropriate therapy (administering a pharmaceutical agent or implementing a standard of care) to the subject determined to have a need therefor. In exemplary aspects, the therapeutic agent is a proteasome inhibitor, including those discussed herein. In exemplary aspects, the therapeutic agent is carfilzomib, bortezomib, disulfiram, or oprozomib. The therapeutic agent may be administered to the subject by any suitable route of administration known in the art, some routes of which are described herein below.

Any and all possible combinations of the steps described herein are contemplated for purposes of the inventive methods.

Tumors and Cancer

As used herein, the term "tumor" refers to an abnormal mass of tissue that results when cells divide at a higher rate than a healthy cell and/or when the cells do not die. In exemplary aspects, the tumor is a malignant tumor. In exemplary aspects, the tumor is a carcinoma, sarcoma, lymphoma, leukemia, germ cell tumor, or a blastoma. In exemplary aspects, the tumor is a hematological tumor, and in further exemplary aspects, the hematological tumor is derived from lymphoid cells. In alternative aspects, the hematological tumor is derived from myeloid cells. In exemplary aspects, the hematological tumor is a lymphoma, e.g., a Hodgkin's lymphoma or a non-Hodgkin's lymphoma. In exemplary aspects, the non-Hodgkin's lymphoma is mantle cell lymphoma. In exemplary aspects, the hematological tumor is a multiple myeloma, including, but not limited to, smouldering myeloma, relapsed multiple myeloma, or refractory myeloma. The multiple myeloma may be of any stage of the International Staging System, including Stage I, Stage II, and Stage III (Greipp et al., *J Clin Oncol* 23: 3412-3420 (2005). In exemplary aspects, the multiple myeloma is a Stage I, Stage II, or Stage III multiple myeloma according to the Durie-Salmon staging system (Durie et al., *Cancer* 36:842-854 (1975).

Samples

With regard to the methods disclosed herein, in exemplary embodiments, the sample obtained from the subject comprises a bodily fluid, including, but not limited to, blood, plasma, serum, lymph, breast milk, saliva, mucous, semen, vaginal secretions, cellular extracts, inflammatory fluids, cerebrospinal fluid, feces, vitreous humor, or urine obtained from the subject. In some aspects, the sample is a composite panel of at least two of the foregoing samples. In exemplary aspects, the sample comprises blood or a fraction thereof (e.g., plasma, serum, fraction obtained via leukopheresis). In exemplary aspects, the sample comprises white blood cells obtained from the subject. In exemplary aspects, the sample comprises a cell or cells from the tumor being treated. The tumor may be any of those described herein, including but not limited to, a hematological tumor, e.g., multiple myeloma tumor, mantle cell lymphoma. In exemplary aspects, the sample comprises bone marrow cells, e.g., intact bone marrow cells. In exemplary aspects, the sample comprises intact bone marrow cells and the method comprises contacting antibodies specific for FCGR2B or for Ig with the sample. In exemplary aspects, the sample comprises blood, serum, a biopsy sample, or bone marrow cells. In exemplary aspects, the sample comprises CD138-positive tumor cells. In exemplary aspects, the sample is a sample obtained from any of the subjects described herein. In exemplary aspects, the sample is a bone marrow aspirate.

Subjects

With regard to the methods disclosed herein, the subject in exemplary aspects is a mammal, preferably a human.

In exemplary aspects, the subject is a subject with a tumor. In exemplary aspects, the tumor is any of those mentioned herein. In exemplary aspects, the subject has cancer. In exemplary aspects, the cancer is any of those mentioned herein. In exemplary aspects, the subject has previously been treated for multiple myeloma. In exemplary aspects, the subject has previously been diagnosed with multiple myeloma. In exemplary aspects, the subject is a human patient having or suspected of having multiple myeloma, refractory multiple myeloma, or relapsed multiple myeloma. In alternative aspects, the subject has never been treated for multiple myeloma. In exemplary aspects, the subject has been newly diagnosed for multiple myeloma.

Proteasome Inhibitors

As used herein, the term "proteasome inhibitor" refers to any drug that blocks the action of proteasomes. In exemplary aspects, the proteasome inhibitor is lactacystin, bortezomib, disulfiram, epigallocatechin-3-gallate, salinosporamide A, carfilzomib, ONX0912, CEP-18770, MLN9708, epoxomicin, MG132, and the like. In exemplary aspects, the proteasome inhibitor is carfilzomib, bortezomib, disulfiram, and oprozomib. In exemplary aspects, the proteasome inhibitor is carfilzomib or bortezomic or a structural analog thereof. In exemplary aspects, the proteasome inhibitor is carfilzomib.

Formulations and Routes of Administration

With regard to the administration of a therapeutic agent, e.g., proteasome inhibitor, the agent may be administered through any suitable means, compositions and routes known in the art.

Kits

The invention further provides kits. In exemplary embodiments, the kit comprises one or more binding agents to an Ig gene or gene segment, or a gene product thereof. In exemplary aspects, the kit comprises a binding agent which specifically binds to an IgH, IgK or IgL gene segment (including orphon gene segments) or a product encoded thereby, and a binding agent to an FCGR2B gene or gene product. In exemplary embodiments, the kits comprises (i) one or more binding agents to an Ig gene segment or a product encoded thereby, optionally an IgH, IgK or IgL gene segment or product encoded thereby, or a binding agent to FCGR2B gene or gene product and (ii) at least one binding agent to a gene listed in Table 4 or a gene product encoded thereby. In exemplary embodiments, the kit comprises at least a first binding agent and a second binding agent, wherein the first binding agent binds to a first gene or gene product encoded by a first gene listed in Table 4, wherein the second binding agent binds to a second gene or gene product encoded by a second gene listed in Table 4, wherein the first gene is different from the second gene.

In exemplary aspects, the kit comprises a proteasome inhibitor, e.g., any of those described herein. In exemplary aspects, the kit comprises a container suitable for holding a blood sample. In exemplary aspects, the kit comprises a vial, a tube, a microtiter plate, a dish, a flask, or the like. In exemplary aspects, the container holds about 5 mL of fluid, or less. In exemplary aspects, the kit comprises heparin to prevent the blood from clotting. In exemplary aspects, the kit comprises reagents suitable for isolating RNA or proteins from tumor cells. In exemplary aspects, the kit comprises reagents suitable for reverse transcribing the RNA into complimentary DNA (cDNA) and for amplification of the cDNA. In exemplary aspects, the kit comprises a reagent that produces a signal indicative of a reference level In exemplary aspects, the product encoded by said gene or gene segment is a nucleic acid molecule, e.g., an mRNA. In exemplary aspects, the binding agent is a nucleic acid probe. In exemplary aspects, the product encoded by said gene or gene segment is a protein, polypeptide, or peptide. In exemplary aspects, the binding agent is an antibody or an antigen-binding fragment thereof or a derivative thereof. In exemplary aspects, the kit comprises both nucleic acid probes and antibodies, or antigen binding fragments or derivatives thereof.

Binding Agents: Nucleic Acid Molecules

In exemplary embodiments, the binding agent is a nucleic acid molecule, e.g., a nucleic acid probe which specifically binds to (i) at least a portion of an Ig gene segment, a FCGR2B gene, or a gene or gene segment listed in Table 4, or (ii) at least a portion of a product encoded by the Ig gene segment, FCGR2B, or the gene or gene segment listed in Table 4, which product comprises nucleic acids. In exemplary aspects, the binding agent is a nucleic acid molecule which is about 5, about 10, about 15, about 20, about 25, about 30, about 35, about 40, about 45 or about 50 nucleotides in length. In exemplary aspects, the nucleic acid molecule is about 15 to about 30 nucleotides in length or about 20 to 30 nucleotides in length or about 25 to 30 nucleotides in length. In exemplary aspects, the nucleic acid molecule is about 25 nucleotides in length.

In exemplary aspects, the nucleic acid molecule comprises DNA or RNA. In exemplary aspects, the nucleic acid molecule comprises at least one non-naturally-occurring nucleotide and/or at least one non-naturally-occurring internucleotide linkage and/or one or more modified nucleotides, all of which are well known in the art. Binding Agents: Antibodies and derivatives Any polynucleotide or polypeptide that binds the gene product may be used to detect its expression levels. In some embodiments, the polypeptide is a fragment of a receptor or ligand of the gene product. In some embodiments of the invention, the binding agent is an antibody that binds to a protein product encoded by an Ig gene segment, an FCGR2B gene, or a gene or gene segment listed in Table 4. The antibody may be any type of immunoglobulin known in the art. In exemplary embodiments, the antibody is an antibody of isotype IgA, IgD, IgE, IgG, or IgM. Also, the antibody in some embodiments is a monoclonal antibody. In other embodiments, the antibody is a polyclonal antibody.

In some embodiments, the antibody is a naturally-occurring antibody, e.g., an antibody isolated and/or purified from a mammal, or produced by a hybridoma generated from a mammalian cell. Methods of producing antibodies are well known in the art.

In some embodiments, the antibody is a genetically-engineered antibody, e.g., a single chain antibody, a humanized antibody, a chimeric antibody, a CDR-grafted antibody, a humaneered antibody, a bispecific antibody, a trispecific antibody, and the like. Genetic engineering techniques also provide the ability to make fully human antibodies in a non-human source.

In some aspects, the antibody is in polymeric, oligomeric, or multimeric form. In certain embodiments in which the antibody comprises two or more distinct antigen binding regions fragments, the antibody is considered bispecific, trispecific, or multi-specific, or bivalent, trivalent, or multivalent, depending on the number of distinct epitopes that are recognized and bound by the antibody.

Antigen Binding Fragments

In some aspects of the invention, the binding agent is an antigen binding fragment of an antibody. The antigen binding fragment (also referred to herein as "antigen binding portion") may be an antigen binding fragment of any of the antibodies described herein. The antigen binding fragment can be any part of an antibody that has at least one antigen binding site, including, but not limited to, Fab, F(ab')$_2$, dsFv, sFv, diabodies, triabodies, bis-scFvs, fragments expressed by a Fab expression library, domain antibodies, VhH domains, V-NAR domains, VH domains, VL domains, and the like.

Computer Related Inventions

Computer readable-storage media are furthermore provided herein. In exemplary embodiments, the computer readable storage medium is one having stored thereon a plurality of reference levels or ranges of reference levels, each reference level or range of reference levels corresponding to (i) an expression level of Ig or (ii) an expression level of FCGR2B, or (iii) an expression level of a gene listed in Table 4, or (iv) a combination thereof; and a data value that is an expression level of Ig and/or an expression level of FCGR2B and/or an expression level of a gene listed in Table 4, measured from a cell from a sample from a patient. In exemplary aspects, the data value that is the expression level of Ig is the sum of the expression levels of more than one gene segment of the IgH, IgK, and/or IgL locus, optionally, wherein the expression level of Ig is indicative of a responder or non-responder In exemplary aspects, the computer readable storage medium is one having stored thereon (I) a first set of data values and a second set of data values, wherein each data value of the first set is an expression level of Ig determined from a sample obtained from a responder and each data value of the second set is an expression level of Ig determined from a sample obtained from a non-responder; (II) a receiver operating characteristic (ROC) curve based on a first set of data values and a second set of data values, wherein each data value of the first set is an expression level of Ig determined from a sample obtained from a responder and each data value of the second set is an expression level of Ig determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

In exemplary embodiments, the computer readable storage medium is one having stored thereon (I) a first set of data values and a second set of data values, wherein each data value of the first set is an expression level of FCGR2B determined from a sample obtained from a responder and each data value of the second set is an expression level of FCGR2B deteremined from a sample obtained from a non-responder; (II) a receiver operating characteristic (ROC) curve based on a first set of data values and a second set of data values, wherein each data value of the first set is an expression level of FCGR2B determined from a sample obtained from a responder and each data value of the second set is an expression level of FCGR2B deteremined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

In exemplary embodiments, the computer readable storage medium is one having stored thereon (I) a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; (II) a receiver operating characteristic (ROC) curve based on a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a). In exemplary aspects, the computer readable storage medium comprises two or more of the foregoing media.

In exemplary embodiments, the computer readable storage medium is one having stored thereon machine-readable instructions executable by a processor, comprising: (a) instructions for receiving a data value, $\alpha$, relating to a test level of Ig expression from a sample obtained from a test subject, e.g., a level of Ig expression measured from a sample obtained from a test subject; and (b) instructions for displaying an output relating to treating the test subject for multiple myeloma with a proteasome inhibitor, when $\alpha$ is greater than $\beta$, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, $\alpha$, relating to a test level of FCGR2B expression from a sample obtained from a test subject, e.g., a level of FCGR2B expression measured from a sample obtained from a test subject; and (b) instructions for displaying an output relating to treating the test subject for multiple myeloma with a proteasome inhibitor, when $\alpha$ is greater than $\beta$, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, $\alpha$, relating to a test level of expression of a gene listed in Table 4 from a sample obtained from a test subject, wherein the change in gene expression level for the gene is denoted in Table 4 as "up", e.g., a level of expression of the gene listed in Table 4 measured from a sample obtained from a test subject; and (b) instructions for displaying an output relating to treating the test subject for multiple myeloma with a proteasome inhibitor, when $\alpha$ is greater than $\beta$, a cutoff correlative with a % specificity of at least 50% and a % sensitivity of at least 50%, as determined by a receiver operating characteristic (ROC) curve.

In exemplary embodiments, the computer readable storage medium is one having stored thereon machine-readable instructions executable by a processor, comprising: (a) instructions for receiving a data value, α, relating to a test level of expression of a gene listed in Table 4 from a sample obtained from a test subject, wherein the change in gene expression level for the gene is denoted in Table 4 as "down", e.g., a level of expression of the gene listed in Table 4 measured from a sample obtained from a test subject; and (b) instructions for displaying an output relating to treating the test subject for multiple myeloma with a proteasome inhibitor, when α is less than β, a cutoff correlative with a % specificity of at least 50% and a % sensitivity of at least 50%, as determined by a receiver operating characteristic (ROC) curve.

The invention additionally provides systems comprising: a processor; a memory device coupled to the processor, and machine readable instructions stored on the memory device. In exemplary embodiments, the machine readable instructions, when executed by the processor, cause the processor to: (i.) receive a data value, α, relating to a test level of Ig expression from a sample obtained from a test subject, e.g., a level of expression of Ig measured from a sample obtained from a test subject; and (ii) display an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of FCGR2B expression from a sample obtained from a test subject, e.g., a level of expression of FCGR2B measured from a sample obtained from a test subject; and (ii) display an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of expression of a gene listed in Table 4, wherein the change in gene expression level for the gene is denoted in Table 4 as "up", from a sample obtained from a test subject, e.g., a level of expression of the gene listed in Table 4 measured from a sample obtained from a test subject; and (ii) display an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve.

In exemplary embodiments, the machine readable instructions, when executed by the processor, cause the processor to: (i) receive a data value, α, relating to a test level of expression of a gene listed in Table 4, wherein the change in gene expression level for the gene is denoted in Table 4 as "down", from a sample obtained from a test subject e.g., a level of expression of the gene listed in Table 4 measured from a sample obtained from a test subject; and (ii) display an output relating to treating the test subject for multiple myeloma with a proteasome inhibitor, when α is less than β, a cutoff correlative with a % specificity of at least 50% and a % sensitivity of at least 50%, as determined by a receiver operating characteristic (ROC) curve.

The invention further provides methods implemented by a processor in a computer. In exemplary embodiments, the method comprises the steps of: (a) receiving a data value, α, relating to a test level of Ig expression from a sample obtained from a test subject e.g., a level of expression of Ig measured from a sample obtained from a test subject; and (b) displaying an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of FCGR2B expression from a sample obtained from a test subject e.g., a level of expression of FCGR2B measured from a sample obtained from a test subject; and (b) displaying an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of expression of a gene listed in Table 4 from a sample obtained from a test subject, wherein the change in gene expression level for the gene is denoted in Table 4 as "up" e.g., a level of expression of the gene listed in Table 4 measured from a sample obtained from a test subject; and (b) displaying an output relating to treating the test subject for multiple myeloma with a proteasome inhibitor, when α is greater than β, a cutoff correlative with a % specificity of at least 50% and a % sensitivity of at least 50%, as determined by a receiver operating characteristic (ROC) curve. In exemplary embodiments, the method comprises the steps of: (a) receiving a data value, α, relating to a test level of expression of a gene listed in Table 4 from a sample obtained from a test subject, wherein the change in gene expression level for the gene is denoted in Table 4 as "down" e.g., a level of expression of the gene listed in Table 4 measured from a sample obtained from a test subject; and (b) displaying an output relating to treating the test subject for multiple myeloma with a proteasome inhibitor, when α is less than β, a cutoff correlative with a % specificity of at least 50% and a % sensitivity of at least 50%, as determined by a receiver operating characteristic (ROC) curve.

Figure 10:
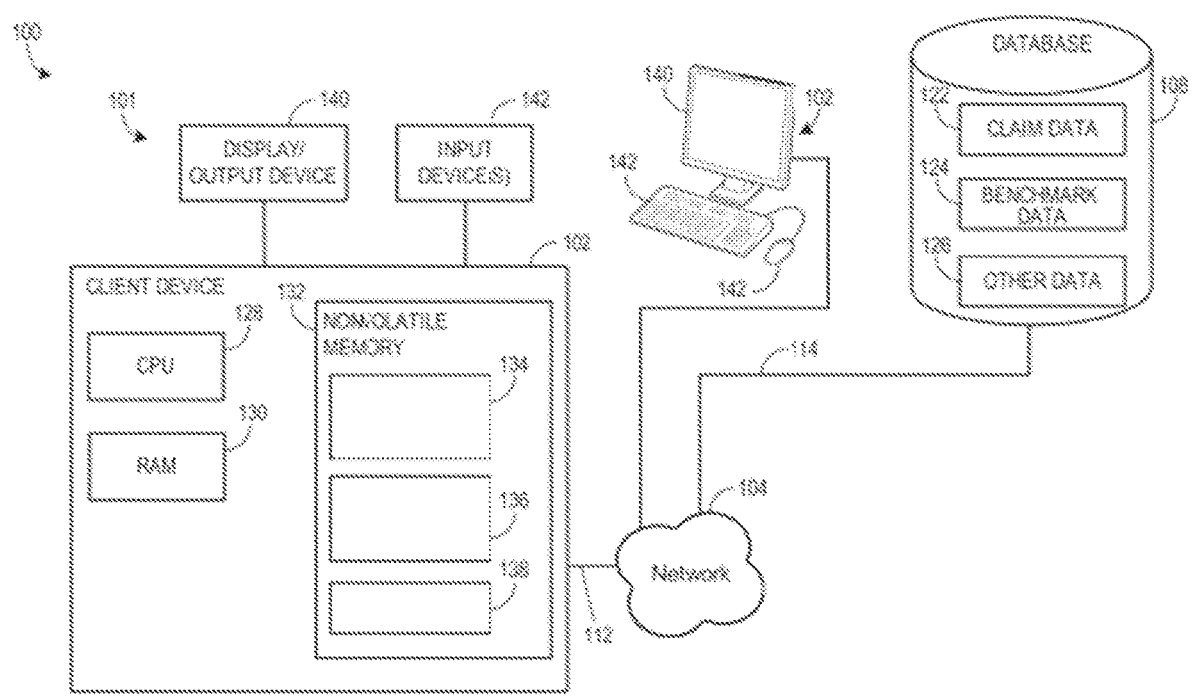
FIG. 10 is a schematic of an exemplary embodiment 101 of a system 100 for determining a therapeutic regimen for a subject with a tumor.

FIG. 10 illustrates an exemplary embodiment 101 of a system 100 for determining a therapeutic regimen for a subject with a tumor. Generally, the system 100 may include one or more client devices 102, a network 104, and a database 108. Each client device 102 may be communicatively coupled to the network 104 by one or more wired or wireless network connections 112, which may be, for example, a connection complying with a standard such as one of the IEEE 802.11 standards ("Wi-Fi"), the Ethernet standard, or any other appropriate network connection. Similarly, the database 108 may be communicatively coupled to the network 104 via one or more connections 114. (Of course, the database could alternatively be internal to one or more of the client devices 102.) The database 108 may store data related to the determination of the therapeutic regimen for a subject with a tumor including, but not limited to, data of a sample obtained from the subject, data of a sample obtained from a subject from a non-responder category or from a responder category, etc. The data of the samples may be, for example, related to one or more of a level of expression of an Ig gene segment, FCGR2B, or a gene or gene segment listed in Table 4.

As will be understood, the network 104 may be a local area network (LAN) or a wide-area network (WAN). That is, network 104 may include only local (e.g., intra-organization) connections or, alternatively, the network 104 may include connections extending beyond the organization and onto one or more public networks (e.g., the Internet). In some embodiments, for example, the client device 102 and the database 108 may be within the network operated by a single company (Company A). In other embodiments, for example, the client device(s) 102 may be on a network operated by Company A, while the database 108 may be on a network operated by a second company (Company B), and the networks of Company A and Company B may be coupled by a third network such as, for example, the Internet.

Referring still to FIG. 10, the client device 102 includes a processor 128 (CPU), a RAM 130, and a non-volatile memory 132. The non-volatile memory 132 may be any appropriate memory device including, by way of example and not limitation, a magnetic disk (e.g., a hard disk drive), a solid state drive (e.g., a flash memory), etc. Additionally, it will be understood that, at least with regard to FIG. 10, the database 108 need not be separate from the client device 102. Instead, in some embodiments, the database 108 is part of the non-volatile memory 132 and the data 122, 124, 126 may be stored as data within the memory 132. For example, the data 122 may be included as data in a spreadsheet file stored in the memory 132, instead of as data in the database 108. In addition to storing the records of the database 108 (in some embodiments), the memory 132 stores program data and other data necessary to analyze data of one or more sample and/or control populations, determine a mean of the data, determine a threshold against which data of the subject may be compared, and/or determine the therapeutic regimen for a subject with a tumor. For example, in an embodiment, the memory 132 stores a first routine 134, a second routine 136, and a third routine 138. The first routine 134 may receive data values related to one or more sample and/or control populations, and determine a mean of the data values received by the routine 134. The second routine 136 may compute one or more statistical parameters of the data collected by the first routine 134, such as determining a mean value, a standard deviation value, etc. Additionally and/or alternatively, the second routine 136 may set a first cutoff against which data from one or more subjects may be compared in order to determine the therapeutic regiment for a subject with a tumor. The third routine 138 may, for example, receive data for one or more subjects, compare the data of the one or more subjects to the cutoff value(s) determined by the second routine 136, and/or determine the therapeutic regimen for a subject with a tumor according to the comparison of the subject's data to the cutoff value. Regardless, each of the routines is executable by the processor 128 and comprises a series of compiled or compilable machine-readable instructions stored in the memory 132. Additionally, the memory 132 may store generated reports or records of data output by one of the routines 134 or 136. Alternatively, the reports or records may be output to the database 108. One or more display/output devices 140 (e.g., printer, display, etc.) and one or more input devices 142 (e.g., mouse, keyboard, tablet, touch-sensitive interface, etc.) may also be coupled to the client device 102, as is generally known.

As will be understood, although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

For example, the network 104 may include but is not limited to any combination of a LAN, a MAN, a WAN, a mobile, a wired or wireless network, a private network, or a virtual private network. Moreover, while only two clients 102 are illustrated in FIG. 10 to simplify and clarify the description, it is understood that any number of client computers are supported and can be in communication with one or more servers (not shown).

Additionally, certain embodiments are described herein as including logic or a number of routines. Routines may constitute either software routines (e.g., code embodied on a machine-readable medium or in a transmission signal) or hardware routines. A hardware routine is tangible unit capable of performing certain operations and may be configured or arranged in a certain manner. In example embodiments, one or more computer systems (e.g., a standalone, client or server computer system) or one or more hardware routines of a computer system (e.g., a processor or a group of processors) may be configured by software (e.g., an application or application portion) as a hardware routine that operates to perform certain operations as described herein.

Similarly, the methods or routines described herein may be at least partially processor-implemented. For example, at least some of the operations of a method may be performed by one or processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Additional Embodiments

The inventions described herein are based, in part, on the discovery that (i) high levels of immunoglobulin expression in cancer cells (e.g., hematological tumor cells) correlate with response to one or more proteasome inhibitors (e.g., carfilzomib, bortezomib, oprozomib); (ii) increased levels of FCGR2B expression in cancer cells (e.g., hematological tumor cells) correlate with response to one or more proteasome inhibitors (e.g., carfilzomib, bortezomib, oprozomib); and/or (iii) decreased levels of FCGR2B expression in cancer cells (e.g., hematological tumor cells) correlate with non-response to proteasome inhibitors (e.g., carfilzomib, bortezomib, oprozomib).

Provided herein are methods for treatment of tumors and/or determining efficacy of a treatment of a tumor with a proteasome inhibitor (e.g., carfilzomib, bortezomib, oprozomib) in a subject by determining the level of Ig expression or FCGR2B expression in a sample obtained from the tumor. These methods require detecting the level of Ig expression or overall Ig protein load in a sample or FCGR2B expression or overall FCGR2B protein load in a sample.

The disclosed methods can be employed to determine the efficacy of treatments for multiple myeloma in subjects who are undergoing carfilzomib therapy and/or in subjects who are undergoing therapy with other chemotherapeutic agents including, but not limited to, other proteasome inhibitors (e.g., oprozomib, bortezomib). Also provided are methods of selecting a subject for participation in a clinical study that include determining the level of Ig expression or FCGR2B expression in a sample (e.g., a biological sample) obtained form a subject having a tumor, or at risk for having a tumor.

The invention also provides additional methods of treating a tumor. In exemplary aspects, the method includes detecting the level of Ig expression or FCGR2B expression in a sample (e.g., a biological sample) obtained from a subject identified as having, or at risk for having a tumor, wherein a difference in the Ig expression level or FCGR2B expression level in the tumor cell compared to a reference level is an indication of the subject's responsiveness to treatment with a proteasome inhibitor. In one embodiment, the Ig expression level or FCGR2B expression level in the tumor cell is elevated as compared to the reference level, and the elevated levels indicate that the tumor is sensitive (e.g., susceptible) to the therapy with one or more proteasome inhibitors. According to one aspect, the methods disclosed herein comprise administering to subjects having elevated levels of Ig expression or FCGR2B expression in the tumor cell as compared to the reference level an effective amount of one or more proteasome inhibitors (e.g. carfilzomib, bortezomib or oprozomib). In one embodiment, the subject is administered an effective amount of carfilzomib.

In another embodiment, the Ig expression level or FCGR2B expression level in the tumor cell is reduced as compared to the reference level, and the reduced levels indicate that the tumor is not sensitive to the therapy with one or more proteasome inhibitors. According to one aspect, the methods disclosed herein comprise administering to subjects having reduced levels of Ig expression or FCGR2B expression in the tumor cell as compared to the reference level an effective amount of a chemotherapeutic agent other than a proteasome inhibitor. In one embodiment, the subject is administered an effective amount of a chemotherapeutic agent other than a carfilzomib. In some embodiments, the tumor is a hematologic tumor (e.g., a myeloma).

In exemplay aspects, the method of treating a tumor in a subject comprises identifying a subject having a tumor, or at risk for having a tumor; providing a sample comprising a cell from a tumor; detecting the level of immunoglobulin (Ig) expression in the sample; identifying a subject with elevated levels of Ig expression in a cell of the tumor as compared to a reference level; and administering to the identified subject an effective amount of a proteasome inhibitor. In exemplary aspects, the method comprises identifying a subject having a tumor, or at risk for having a tumor; providing a sample comprising a cell from a tumor; detecting the level of immunoglobulin (Ig) in the sample; identifying a subject with reduced levels of Ig in a cell of the tumor as compared to a reference level; and administering to the subject a chemotherapeutic agent other than a proteasome inhibitor.

In exemplary aspects, the method of treating a tumor in a subject comprises identifying a subject having a tumor, or at risk for having a tumor; providing a sample comprising a cell from a tumor; detecting the level of Fc gamma receptor 2B (FCGR2B) expression in the sample; identifying a subject with elevated levels of FCGR2B expression in a cell of the tumor as compared to a reference level; and administering to the identified subject an effective amount of a proteasome inhibitor. In exemplary aspects, the method comprises identifying a subject having a tumor, or at risk for having a tumor; providing a sample comprising a cell from a tumor; detecting the level of FCGR2B in the sample; identifying a subject with reduced levels of FCGR2B in a cell of the tumor as compared to a reference level; and administering to the subject a chemotherapeutic agent other than a proteasome inhibitor.

The invention also provides a method for determining whether to treat a subject having a tumor, e.g., a hematological tumor, with a proteasome inhibitor, e.g., carfilzomib. In exemplary aspects, the method of determining whether to treat a subject comprises identifying a subject having a hematological tumor, or at risk for having a hematological tumor. In one aspect, the hematological tumor is multiple myeloma. The level of Ig expression or FCGR2B expression in a sample (e.g., a biological sample) obtained from a subject is detected, and compared to a reference level. According to one aspect, the methods include determining to treat the subject with carfilzomib if the sample has elevated levels of Ig or FCGR2B, as compared to a reference level. In one embodiment, the subject is administered an effective amount of carfilzomib. Conversely, the methods include determining to treat the subject with a chemotherapeutic agent other than carfilzomib if the sample has reduced levels of Ig or FCGR2B as compared to a reference level. In exemplary aspects, the method comprises identifying a subject having a tumor, or at risk for having a tumor; providing a sample comprising a cell from the tumor; detecting the level of immunoglobulin (Ig) expression in the sample; and determining to treat a subject with a proteasome inhibitor, e.g., carfilzomib, if the subject has elevated levels of Ig in the sample as compared to a reference level. In exemplary aspects, the method further includes the step of administering to subject an effective amount of a proteasome inhibitor, e.g., carfilzomib.

In alternative or additional aspects, the method comprises identifying a subject having, at risk for, having a tumor, e.g., a hematological tumor; providing a sample comprising a cell from the tumor; detecting the level of FCGR2B expression in the sample; and determining to treat a subject with a proteasome inhibitor, e.g, carfilzomib, if the subject has elevated levels of FCGR2B in the sample as compared to a reference level. In exemplary aspects, the method further includes the step of administering to subject an effective amount of a proteasome inhibitor, e.g., carfilzomib.

The invention further provides a method of predicting the sensitivity of a tumor (e.g., a hematological tumor) to treatment with a proteasome inhibitor. In exemplary embodiments, the methods comprise identifying a subject having a tumor, or at risk for having a tumor. In one aspect, the tumor is multiple myeloma. These methods include detecting the level of Ig expression or FCGR2B expression in a sample (e.g., a biological sample) obtained from a subject identified as having, or at risk for having a tumor, and predicting that the tumor will be sensitive to (e.g., susceptible to) treatment with proteasome inhibitor if the sample has elevated levels of Ig or FCGR2B in the sample relative to a reference level. In one embodiment, the Ig expression level or the FCGR2B expression level in the sample is elevated as compared to the reference level, and the elevated levels indicate that the tumor is sensitive (e.g., susceptible) to the therapy with a proteasome inhibitor. According to one aspect, the methods disclosed herein comprise administering to subjects having elevated levels of Ig expression or FCGR2B expression in the sample as compared to the reference level an effective amount of proteasome inhibitor, including carfilzomib. In exemplary aspects, the method comprises identifying a subject having a tumor, or at risk for having a tumor; providing a sample comprising a cell from the tumor; detecting the level of Ig expression in the sample; comparing the level of Ig expressiong in the sample with a reference level; predicting that the tumor will be sensitive to treatment with a proteasome inhibitor if the sample has elevated levels of Ig in the sample relative to a reference level. In exemplary aspects, the method further includes the step of administering to the subject having a tumor predicted to be sensitive to treatment with a proteasome inhibitor, e.g., carfilzomib, an effective amount of a proteasome inhibitor, e.g., carfilzomib. In alternative or additional aspects, the method comprises identifying a subject having a tumor, or at risk for having a tumor; providing a sample comprising a cell from the tumor; detecting the level of FCGR2B expression in the sample; comparing the level of FCGR2B expression in the sample with a reference level; predicting that the tumor will be sensitive to treatment with a proteasome inhibitor if the sample has elevated levels of FCGR2B in the sample relative to a reference level. In exemplary aspects, the method further includes the step of administering to the subject having a tumor predicted to be sensitive to treatment with proteasome inhibitor, e.g., carfilzomib, an effective amount of a proteasome inhibitor, e.g., carfilzomib.

In another embodiment, the methods include detecting the level of Ig expression or FCGR2B expression in a sample (e.g., a biological sample) obtained from a subject identified as having, or at risk for having a tumor, and predicting that the tumor will not be sensitive (e.g., susceptible to) to treatment with proteasome inhibitor if the sample has reduced levels of Ig or FCGR2B in the sample relative to a reference level. According to one aspect, the methods disclosed herein comprise administering to subjects having reduced levels of Ig expression or FCGR2B expression in the tumor cell as compared to the reference level an effective amount of a chemotherapeutic agent other than a proteasome inhibitor. In one embodiment, the methods further comprise administering to the subject an effective amount of a chemotherapeutic agent other than a proteasome inhibitor (e.g., a chemotherapeutic agent other than carfilzomib).

Some embodiments, where the treatment has been indicated to be ineffective in the subject, further include administering, recommending, or prescribing an alternate treatment to the subject. In some embodiments, the alternate treatment can be a different therapeutic agent or a different combination of one or more therapeutic agents. In some embodiments, the alternate treatment can be an increased dosage of one or more therapeutic agents currently being taken by the subject, an increase in the frequency of administration of one or more therapeutic agents currently being taken by the subject, or an alteration in the route of delivery of one or more therapeutic agents being currently taken by the subject.

In exemplary aspects of the foregoing methods, the proteasome inhibitor is selected from the group consisting of carfilzomib, bortezomib and oprozomib. In exemplary aspects, the tumor is a hematological tumor, including, but not limited to multiple myeloma. In exemplary aspecst, the the cell is a CD138+ tumor cell.

In exemplary aspects of the foregoing methods comprising detecting the level of immunoglobulin (Ig) in the sample, the detecting comprises amplifying a fragment of a human Ig mRNA. In one embodiment, the detecting comprises measuring the Ig expression level in the cell using a microarray platform that map to genes encoding Ig-related proteins. In yet another embodiment, the detecting comprises measuring the Ig expression level in the cells using an anti-Ig antibody (e.g., an anti-human Ig antibody). In exemplary aspects of the foregoing methods comprising detecting the level of immunoglobulin (Ig) in the sample, the detecting comprises (i) amplifying a fragment of a human Ig mRNA; (ii) measuring the Ig expression level in the cell using a microarray platform that map to genes encoding Ig-related proteins; or (iii) measuring the Ig protein load in the cells with an anti-human Ig antibody.

In exemplary aspects of the foregoing methods comprising detecting the level of FCGR2B in the sample, the detecting comprises amplifying a fragment of a human FCGR2B mRNA. In one embodiment, the detecting comprises measuring the FCGR2B expression level in the cell using a microarray platform that map to genes encoding FCGR2B. In yet another embodiment, the detecting comprises measuring the Ig expression level in the cells using an anti-FCGR2B antibody (e.g., an anti-human FCGR2B antibody). In exemplary aspects of the foregoing methods comprising detecting the level of FCGR2B in the sample, the detecting comprises (i) amplifying a fragment of a human FCGR2B mRNA; (ii) measuring the FCGR2B expression level in the cell using a microarray platform that map to genes encoding FCGR2B; or (iii) measuring the FCGR2B protein load in the cells with an anti-human FCGR2B antibody.

The invention moreover provides a method of inhibiting proliferation of multiple myeloma cells in a subject. In exemplary aspects, the methods include detecting the level of Ig expression or FCGR2B expression level in multiple myeloma cells obtained from a subject, wherein a difference in the Ig expression level or FCGR2B expression level in the multiple myeloma cells compared to a reference level is an indication that treating the subject with a proteasome inhibitor will inhibit proliferation of multiple myeloma cells in the subject. In an exemplary embodiment, the Ig expression level or FCGR2B expression level in the multiple myeloma cells is elevated as compared to the reference level, and the elevated levels indicate that treating the subject with a proteasome inhibitor will inhibit proliferation of multiple myeloma cells in the subject. According to one aspect, the methods disclosed herein comprise administering to the subject an effective amount of a proteasome inhibitor. In one embodiment, the subject is administered an effective amount of carfilzomib. In another embodiment, the methods disclosed herein include designing a chemotherapeutic regimen comprising carfilzomib effective to inhibit proliferation of the tumor cells; and administering carfilzomib to the subject thereby treating the tumor.

In another embodiment, the Ig expression level or FCGR2B expression level in the multiple myeloma cells is reduced as compared to the reference level, and the reduced levels indicate that treating the subject with a proteasome inhibitor may not inhibit proliferation of multiple myeloma cells in the subject. According to one aspect, the methods disclosed herein comprise administering to the subjects an effective amount of a chemotherapeutic agent other than a proteasome inhibitor. In one embodiment, the subject is administered an effective amount of a chemotherapeutic agent other than a carfilzomib.

In exemplary aspects, the method of inhibiting proliferation of multiple myeloma cells in a subject comprises identifying a subject having, at risk for, or suspected of having multiple myeloma; detecting the level of Ig expression in multiple myeloma cells obtained from the subject; comparing the level of Ig expression in the multiple myeloma cells with a control sample; and a) administering to the subject an effective amount of a proteasome inhibitor to the subject if it has been determined that the multiple myeloma cells have elevated Ig expression relative to a reference level; or b) administering to the subject an effective amount of a chemotherapeutic agent other than a proteasome inhibitor to the subject if it has been determined that the multiple myeloma cells have reduced Ig expression relative to a reference level. In alternative or additional aspects, the method comprises identifying a subject having, at risk for, or suspected of having multiple myeloma; detecting the level of FCGR2B expression in multiple myeloma cells obtained from the subject; comparing the level of FCGR2B expression in the multiple myeloma cells with a control sample; and a) administering to the subject an effective amount of a proteasome inhibitor to the subject if it has been determined that the multiple myeloma cells have elevated FCGR2B expression relative to a reference level; or b) administering to the subject an effective amount of a chemotherapeutic agent other than a proteasome inhibitor to the subject if it has been determined that the multiple myeloma cells have reduced or unchanged FCGR2B expression relative to a reference level.

In exemplary aspects, the methods provided herein, (e.g., the method of determining whether to treat a subject), further comprises designing a chemotherapeutic regimen comprising carfilzomib effective to inhibit proliferation of the tumor cells (e.g., multiple myeloma cells); and administering carfilzomib to the subject thereby treating the tumor.

In exemplary aspects of any of the foregoing methods, the reference level of Ig is based on the Ig expression level determined from a plasma cell obtained from a healthy individual or the reference level of FCGR2B is based on the FCGR2B expression level determined from a plasma cell obtained from a healthy individual. In exemplary aspects, the reference level of Ig expression is based on the Ig expression level determined from a plasma cell obtained from an individual classified as non-responsive to therapy with a proteasome inhibitor. In exemplary embodiments, the reference level of FCGR2B expression is based on the FCGR2B expression level determined from a plasma cell obtained from a healthy individual. In another embodiment, the reference level of FCGR2B expression is based on the FCGR2B expression level determined from a plasma cell obtained from an individual classified as non-responsive to therapy with a proteasome inhibitor.

In exemplary aspects of any of the foregoing methods, the subject has previously been treated for multiple myeloma or has previously been diagnosed with multiple myeloma. In exemplary aspects of any of the foregoing methods, the sample is a blood, serum, or biopsy sample.

Also, in exemplary aspects of any of the foregoing methods, the detecting comprises amplifying a fragment of a human Ig mRNA or amplifying a fragment of a human FCGR2B mRNA. Optionally, the amplifying is by polymerase chain reaction (PCR) or RT-PCR. In exemplary aspects, the amplifying employs a detectably-labeled primer or probe.

With regard to the foregoing methods, the Ig expression levels or FCGR2B expression levels in a biological sample can be determined, for example, by using one or more oligonucleotides that are specific for genes encoding Ig-related proteins or for FCGR2B. For example, the levels of mRNA corresponding to a human Ig or human FCGR2B can be detected using oligonucleotides in Southern hybridizations, in situ hybridizations, and quantitative real-time PCR amplification (qRT-PCR). A plurality of oligonucleotides specific for a plurality genes encoding Ig-related proteins can be employed in an array format wherein each oligonucleotide is immobilized at a pre-determined location on a substrate, such as nitrocellulose membrane. Methods for performing such assays are well known to those of skill in the art.

The oligonucleotides employed in such methods are generally single-stranded molecules, such as synthetic antisense molecules or cDNA fragments, and are, for example, 6-60 nt, 15-30 or 20-25 nt in length.

Oligonucleotides specific for a polynucleotide encoding Ig-related proteins are prepared using techniques well known to those of skill in the art. For example, oligonucleotides can be designed using known computer algorithms to identify oligonucleotides of a defined length that are unique to the polynucleotide, have a GC content within a range suitable for hybridization, and lack predicted secondary structure that may interfere with hybridization. Oligonucleotides can be synthesized using methods well known to those in the art. For use in array formats, the oligonucleotides may be synthesized directly on the surface of a substrate. Oligonucleotides specific for the prostate cancer biomarkers disclosed herein are known in the art and are commercially available.

In certain embodiments, the oligonucleotides are labeled using one or more detectable moieties. DNA or mRNA isolated from a biological sample is contacted with the labeled oligonucleotides under conditions that allow for formation of hybridization complexes, and the amount of label associated with the hybridization complexes is measured and compared to a standard value.

In alternative or additional aspects, the detecting comprises measuring the presence, absence, or amount of a human Ig protein or FCGR2B protein in the test sample. In exemplary aspects, the measuring uses an antibody that specifically binds to a human Ig protein or a human FCGR2B protein. Antibodies that bind to human Ig employed in the present methods, together with ELISA kits that employ such antibodies for the detection of human Ig employed herein, are well known to those of skill in the art and are available commercially. Optionally, the measuring is by an ELISA assay, a western blot assay, or an immunohistochemical assay.

In certain embodiments, the Ig or FCGR2B, expression level is determined using a binding agent, such as a protein, antibody or antibody fragment, that specifically binds to the human Ig or FCGR2B, for example in an enzyme-linked immunosorbent assay (ELISA), radioimmunoassay, antibody array, Western blot, immunohistochemical, immunoprecipitation or immunofluoresence assay. Methods for performing such assays are well known to those of skill in the art.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate.

With regard to the foregoing methods, in exemplary aspects, the subject is a human patient having or suspected of having multiple myeloma, refractory multiple myeloma, or relapsed multiple myeloma.

In exemplary embodiments, the method further comprises administering to the subject one or more chemotherapeutic agents other than a proteasome inhibitor (e.g., carfilzomib, bortezomib or oprozomib). In some embodiments, the subject is a participant in a clinical trial. In alternative embodiments, the method further comprises administering to the subject one or more chemotherapeutic agents other than a proteasome inhibitor.

In exemplary embodiments, the difference is an increase in the level of Ig expression or FCGR2B expression in the tumor cell compared to the reference level and the increase is prognostic for an improved overall survival of the subject undergoing the therapy, compared to individuals afflicted with multiple myeloma that do not have the increase in the expression level of Ig or FCGR2B in the tumor cell compared to a reference level.

In one embodiment, the difference is a decrease in the level of Ig expression in the tumor cell in the subject compared to the reference level and the decrease indicates that the multiple myeloma is resistant to therapy with one or more proteasome inhibitors. In one embodiment, the difference is a decrease in the level of Ig expression in the tumor cell compared to the reference level and the decrease is prognostic for a diminished overall survival of the subject compared to individuals that do not have the decrease in the level of Ig expression in the tumor cell. In exemplary aspects, the difference is an decrease in the level of FCGR2B expression in the tumor cell compared to the reference level and the decrease is prognostic for an diminished overall survival of the subject undergoing the therapy, compared to individuals afflicted with multiple myeloma that do not have an decrease in the expression level of FCGR2B in the tumor cell compared to a reference level.

In exemplary embodiments, the method further includes determining whether the patient will be a candidate for therapy with one or more proteasome inhibitors, prior to the administering, wherein an increase in a level of Ig expression or FCGR2B expression in a tumor cell from the patient compared to a reference level indicates that the patient is a candidate for the foregoing therapies.

Provided herein are methods for determining whether to treat a patient having a tumor (e.g., a hematological tumor) with a proteasome inhibitor (e.g., carfilzomib) that include identifying a subject having, at risk for, having a hematological tumor, providing a sample comprising a cell from the tumor, detecting the level of Ig expression in the sample, determining to treat the patient with a proteasome inhibitor (e.g., carfilzomib) if the level of Ig expression in a cell of the tumor is greater than a predetermined reference level. In some embodiments, the hematological tumor is a myeloma. In some embodiments, the myeloma is multiple myeloma.

Provided herein are methods for determining whether to treat a patient having a tumor (e.g., a hematological tumor, such as multiple myeloma) with a proteasome inhibitor (e.g., carfilzomib, oprozomib, or bortezomib) that include identifying a subject having a tumor, or at risk for having a tumor, providing a sample comprising a cell from the tumor, detecting the level of FCGR2B expression in the sample, determining to treat the patient with a chemotherapeutic agent other than a proteasome inhibitor when if the level of FCGR2B expression in a cell of the tumor is less than a predetermined reference level. In some embodiments, the hematological tumor is a myeloma. In some embodiments, the myeloma is multiple myeloma.

Some embodiments further include assessing, or alternatively obtaining, providing, or using previously determined information regarding, the level of Ig expression or FCGR2B expression from samples taken from a control population of normal, or healthy (disease-free) subjects.

Some embodiments further include recording the results of these methods in the subject's medical records (e.g., recording the results in a computer readable medium) or performing a diagnostic test. In some embodiments, these methods can be performed by a medical professional (e.g., a physician, a physician's assistant, a nurse, a nurse's assistant, or a laboratory technician).

In one aspect, the disclosure generally provides compositions, which include therapeutic agents and pharmaceutically acceptable carriers therefor.

In this regard, the disclosure provides for one or more therapeutic agents, e.g., proteasome inhibitors, which are administered to a MM patient. The therapeutic agents can be administered to a patient prior to, during, or after other conventional chemotherapeutic treatments. In one embodiment, the therapeutic agents are administered to a patient subsequent to determining that the patient is a candidate for such treatment. In this respect, the therapeutic agents are administered to a subject, prior to, or in combination with, conventional chemotherapeutic treatments.

In one aspect, the therapeutic agents, alone or in combination, are administered to a patient in an effective amount, e.g., a therapeutically effective dose of proteasome inhibitor or other chemotherapeutic agent. A therapeutic dose may vary depending upon the type of therapeutic agent, route of administration, and dosage form. Dosage unit forms generally contain between from about 1 mg to about 500 mg of an active ingredient. The preferred composition or compositions is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation.

In the compositions for treating multiple myeloma described herein, the therapeutically effective amount of the proteasome inhibitor can range from about 0.001 mg/kg to about 30 mg/kg body weight of the subject. In some embodiments, the therapeutically effective amount of the agent can range from about 0.05 mg/kg to about 30 mg/kg, from about 0.1 mg/kg to about 30 mg/kg, from about 1 mg/kg to about 25 mg/kg, from about 1 mg/kg to about 20 mg/kg, or from about 1 or 2 mg/kg to about 15 mg/kg.

The methods described herein include the manufacture and use of pharmaceutical compositions, which include compounds (e.g., proteasome inhibitors and/or other chemotherapeutic agents) identified by a method described herein as active ingredients. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., chemotherapeutic agents.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

With regard to the inventions described in the section titled "Additional Embodiments" the following applies:

As disclosed herein, the term "immunoglobulin expression" or "Ig expression" refers to the expression level of one or more of the known immunoglobulin classes including IgA, IgG, IGM, IgE, and IgD.

As used herein, the term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)2 as well as single chains (scFv) or diabodies. Immunoglobulins can come in different varieties known as isotypes or classes. In placental mammals there are five antibody isotypes known as IgA, IgD, IgE, IgG and IgM. They are each named with an "Ig" prefix that stands for immunoglobulin, another name for antibody, and differ in their biological properties, functional locations and ability to deal with different antigens.

As used herein, the term "antibody" refers to an immunoglobulin and any antigen-binding portion of an immunoglobulin, e.g., IgG, IgD, IgA, IgM and IgE, or a polypeptide that contains an antigen binding site, which specifically binds or "immunoreacts with" an antigen. Antibodies can comprise at least one heavy (H) chain and at least one light (L) chain inter-connected by at least one disulfide bond. The term "VH" refers to a heavy chain variable region of an antibody. The term "VL" refers to a light chain variable region of an antibody. In exemplary embodiments, the term "antibody" specifically covers monoclonal and polyclonal antibodies. A "polyclonal antibody" refers to an antibody which has been derived from the sera of animals immunized with an antigen or antigens. A "monoclonal antibody" refers to an antibody produced by a single clone of hybridoma cells.

As used herein, the term "biomarker" refers to a molecule that is associated either quantitatively or qualitatively with a biological change. Examples of biomarkers include: polypeptides, proteins or fragments of a polypeptide or protein; polynucleotides, such as a gene product, RNA or RNA fragment; and other body metabolites.

As disclosed herein, the term "hematological malignancy" or "hematological tumor" refers to cancers that affect blood and bone marrow.

The term "myeloma" as used herein means any tumor or cancer composed of cells derived from the hemopoietic tissues of the bone marrow. For example, myeloma includes multiple myeloma.

The "proteasome" as used herein refers to a multimeric enzymatic complex involved in the degradation of protein.

As disclosed herein, the term "proteasome inhibitor" is intended to include compounds which target, decrease or inhibit the activity of the proteasome. Compounds which target, decrease or inhibit the activity of the proteasome include, but are not limited to, carfilzomib (Kyprolis), oprozomib and bortezomib (Velcade).

As used herein, to "inhibit" or "suppress" or "reduce" a function or activity, such as proteasomal activity, is to reduce the function or activity when compared to otherwise same conditions except for a condition or parameter of interest, or alternatively, as compared to another condition.

As used herein, the term "reference level" refers to a level of a substance which may be of interest for comparative purposes. In one embodiment, a reference level may be the expression level of a protein or nucleic acid expressed as an average of the level of the expression level of a protein or nucleic acid from samples taken from a control population of normal, or healthy (disease-free) subjects. In another embodiment, the reference level may be the level in the same subject at a different time, e.g., before the present assay, such as the level determined prior to the subject developing the disease or prior to initiating therapy. In general, samples are normalized by a common factor. For example, body fluid samples are normalized by volume body fluid and cell-containing samples are normalized by protein content or cell count. In another embodiment, the reference level may also refer to the level of expression of the same biomarker in a corresponding control sample or control group of subjects which do not respond to PI treatment (e.g., treatment with carfilzomib, oprozomib or bortezomib).

As used herein, the term "subject" refers to a mammal, preferably a human, who may or may not have cancer. Typically, the terms "subject" and "patient" are used interchangeably herein in reference to a human subject. The subject may be a patient undergoing proteasome inhibition s (e.g., carfilzomib, oprozomib, bortezomib or other related agent) therapy using a sole therapeutic agent. The subject may be a patient undergoing proteasome inhibition s (e.g., carfilzomib, oprozomib, bortezomib or other related agent) therapy using a therapeutic agent in conjunction with another agent (e.g., a chemotherapeutic agent).

As used herein, the term "sample" or "test sample" refers to any liquid or solid material, specimen or culture obtained from any source containing nucleic acids or proteins. In suitable embodiments, a test sample is obtained from a biological source, e.g., a "biological sample". Biological samples include blood products (such as plasma, serum, whole blood and peripheral blood mononuclear cells (PBMCs)), urine, saliva, blood, serum, or biopsy sample and the like. Biological samples also include tissue samples, such as biopsy tissues or pathological tissues that have previously been fixed (e.g., formalin, snap frozen, cytological processing, etc.). In an exemplary embodiment, the sample is a tumor sample.

The terms "detecting", "determining," "measuring," "assessing," and "assaying" are used interchangeably and include both quantitative and qualitative determinations. These terms refer to any form of measurement, and include determining if a characteristic, trait, or feature is present or not.

As used herein, the phrase "difference of the level" refers to differences in the quantity of a particular marker, such as a biomarker protein or nucleic acid, in a sample as compared to a control or reference level. For example, the quantity of particular protein or nucleic acid may be present at an elevated amount or at a decreased amount in samples of patients with a disease compared to a reference level. In one embodiment, a "difference of a level" may be a difference between the level of biomarker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a statistically significant difference between the level of the biomarker present in a sample as compared to a control. For example, a difference may be statistically significant if the measured level of the biomarker falls outside of about 1.0 standard deviations, about 1.5 standard deviations, about 2.0 standard deviations, or about 2.5 standard deviations of the mean of any control or reference group.

The term "elevated levels", "increased levels" or "higher levels" as used herein refers to levels of a biomarker protein or nucleic acid that are higher than what would normally be observed in a comparable sample from control or normal subjects, e.g., a reference value. In some embodiments, "control levels", e.g., normal levels, refer to a range of biomarker protein or nucleic acid levels that would normally be expected to be observed in a sample from a mammal that does not have a disease. A control level may be used as a reference level for comparative purposes. "Elevated levels" refer to biomarker protein or nucleic acid levels that are above the range of reference levels (e.g, control levels). The ranges accepted as "elevated levels" or "reference levels" are dependent on a number of factors. For example, one laboratory may routinely determine the level of biomarker protein or nucleic acid in a sample that are different than the level obtained for the same sample by another laboratory. Also, different assay methods may achieve different value ranges. Value ranges may also differ in various sample types, for example, different body fluids or by different treatments of the sample. One of ordinary skill in the art is capable of considering the relevant factors and establishing appropriate reference ranges for "control values" and "elevated values" of the present disclosure. For example, a series of samples from control subjects and subjects diagnosed with cancer can be used to establish ranges that are "normal" or "control" levels and ranges that are "elevated" or "higher" than the control range. In one embodiment, expression/amount of a gene or biomarker (e.g., Ig expression levels) in a sample is at an "elevated level" compared with a reference value if the expression level/amount of the gene or biomarker in the sample is at least about 1.5×, 1.75×, 2×, 3×, 4×, 5×, 6×, 7×, 8×, 9× or 10× the expression level/amount of the gene or biomarker in reference value.

Similarly, "reduced levels" or "lower levels" as used herein refer to levels of a biomarker protein or nucleic acid that are lower than what would normally be observed in a comparable sample from control or normal subjects, e.g., a reference value. In some embodiments, "control levels", e.g., normal levels, refer to a range of biomarker protein or nucleic acid levels that would be normally be expected to be observed in a mammal that does not have a disease and "reduced levels" refer to biomarker protein or nucleic acid levels that are below the range of control levels.

As used herein, the terms "gene expression" or "expression" refer to the process of converting genetic information encoded in a gene into RNA, e.g., mRNA, rRNA, tRNA, or snRNA, through transcription of the gene, e.g., via the enzymatic action of an RNA polymerase, and for protein encoding genes, into protein through translation of mRNA. Gene expression can be regulated at many stages in the process.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, e.g. there may be differential diagnoses that can be inferred from a diagnostic factor or symptom. Likewise, there may be instances where a factor or symptom that is indicative of a particular disease is present in an individual that does not have the particular disease. The term "diagnosis" also encompasses determining the therapeutic effect of a drug therapy, or predicting the pattern of response to a drug therapy. The diagnostic methods may be used independently, or in combination with other diagnosing and/or staging methods known in the medical arts for a particular disease or disorder, e.g., MM.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. The terms "favorable prognosis" and "positive prognosis," or "unfavorable prognosis" and "negative prognosis" as used herein are relative terms for the prediction of the probable course and/or likely outcome of a condition or a disease. A favorable or positive prognosis predicts a better outcome for a condition than an unfavorable or negative prognosis. In a general sense, a "favorable prognosis" is an outcome that is relatively better than many other possible prognoses that could be associated with a particular condition, whereas an unfavorable prognosis predicts an outcome that is relatively worse than many other possible prognoses that could be associated with a particular condition. Typical examples of a favorable or positive prognosis include a better than average remission rate, a lower propensity for metastasis, a longer than expected life expectancy, differentiation of a benign process from a cancerous process, and the like.

As used herein, the term "effective amount" or "pharmaceutically effective amount" or "therapeutically effective amount" refers to is a quantity of the compound(s) in a preparation which, when administered as part of a dosage regimen (to a mammal, e.g., a human) sufficient to achieve a desired therapeutic and/or prophylactic effect, e.g., an amount which alleviates a symptom, ameliorates a condition, or slows the onset of disease conditions according to clinically acceptable standards for the disorder or condition to be treated. The amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds and/or treatments.

As used herein, the term "treating" or "treatment" includes reversing, reducing, or arresting the symptoms, clinical signs, and underlying pathology of a condition in manner to improve or stabilize a subject's condition.

As used herein, "microarray" or "gene expression array" or "array" or "tissue microarray" refers to an arrangement of a collection of nucleic acids, e.g., nucleotide sequences in a centralized location. Arrays can be on a solid substrate, such as a glass slide, or on a semi-solid substrate, such as nitrocellulose membrane. The nucleotide sequences can be DNA, RNA, or any combination or permutations thereof. The nucleotide sequences can also be partial sequences or fragments from a gene, primers, whole gene sequences, non-coding sequences, coding sequences, published sequences, known sequences, or novel sequences.

Exemplary embodiments of the invention include:

1. A method of treating a tumor in a subject, comprising:
   a) measuring the level of expression of (i) immunoglobulin (Ig), (ii) Fc gamma receptor 2B (FCGR2B), or (iii) both Ig and FCGR2B, in a sample obtained from the subject, wherein the sample comprises a cell from the tumor; and
   b) administering to the subject an effective amount of a proteasome inhibitor when the level of Ig expression and/or FCGR2B expression in the sample is greater than a reference level.

2. A method of treating a tumor in a subject from which a sample was obtained, wherein the level of expression of (i) immunoglobulin (Ig), (ii) Fc gamma receptor 2B (FCGR2B), or (iii) both Ig and FCGR2B, has been measured from the sample, the method comprising the step of administering to the subject an effective amount of a proteasome inhibitor when the level of expression is greater than a reference level.

3. A method of determining a treatment regimen for a subject with a tumor, comprising:
   a) measuring the level of expression of (i) immunoglobulin (Ig), (ii) Fc gamma receptor 2B (FCGR2B), or (iii) both Ig and FCGR2B, in a sample obtained from the subject, wherein the sample comprises a cell from the tumor, and
   b) selecting a treatment regimen comprising administration of a proteasome inhibitor, when the level of Ig expression and/or FCGR2B expression in the sample is greater than a reference level.

4. The method of any one of claims 1-3, wherein the proteasome inhibitor is selected from the group consisting of carfilzomib, bortezomib, disulfiram, and oprozomib.

5. The method of any one of claims 1-4, wherein the tumor is a hematological tumor, optionally, a hematological tumor derived from lymphoid cells.

6. The method of claim 5, wherein the hematological tumor is a lymphoma, optionally a non-Hodgkin's lymphoma.

7. The method of claim 6, wherein the non-Hodgkin's lymphoma is mantle cell lymphoma.

8. The method of claim 5, wherein the hematological tumor is a multiple myeloma.

9. The method of claim 8, wherein the multiple myeloma is smouldering myeloma, relapsed multiple myeloma, or refractory myeloma.

10. The method of any one of claims 1-9, wherein the level of expression of (i) Ig, (ii) FCGR2B, or (iii) both Ig and FCGR2B, is measured in CD138-positive tumor cells obtained from the subject.

11. The method of claim 10, comprising extracting RNA from the CD138-positive tumor cells.

12. The method of any one of claims 1-11, wherein the sample comprises bone marrow cells, blood, serum, or a biopsy sample.

13. The method of claim 12, comprising contacting antibodies specific for FCGR2B or for Ig with the sample comprising intact bone marrow cells.

14. The method of any one of claims 1-13, comprising measuring the level of expression of one or more gene segments of the IgH locus, IgK locus, or IgL locus, or an IgH orphon gene segment, an IgK orphon gene segment, or an IgL orphon gene segment, or a combination thereof.

15. The method of claim 14, wherein the one or more gene segments at the IgH locus or the IgH orphon gene segment is selected from the group consisting of: IGHA1, IGHA2, IGHD, IGHD1-1, IGHD1-14, IGHD1-20, IGHD1-26, IGHD1-7, IGHD2-15, IGHD2-2, IGHD2-21, IGHD2-8, IGHD3-10, IGHD3-16, IGHD3-22, IGHD3-3, IGHD3-9, IGHD4-11, IGHD4-17, IGHD4-23, IGHD4-4, IGHD5-12, IGHD5-18, IGHD5-24, IGHD5-5, IGHD6-13, IGHD6-19, IGHD6-25, IGHD6-6, IGHD7-27, IGHE, IGHEP1, IGHEP2, IGHG1, IGHG2, IGHG3, IGHG4, IGHGP, IGHJ1, IGHJ1P, IGHJ2, IGHJ2P, IGHJ3, IGHJ3P, IGHJ4, IGHJ5, IGHJ6, IGHM, IGHMBP2, IGHV1-12, IGHV1-14, IGHV1-17, IGHV1-18, IGHV1-2, IGHV1-24, IGHV1-3, IGHV1-45, IGHV1-46, IGHV1-58, IGHV1-67, IGHV1-68, IGHV1-69, IGHV1-8, IGHV1OR21-1, IGHV2-10, IGHV2-26, IGHV2-5, IGHV2-70, IGHV2OR16-5, IGHV3-11, IGHV3-13, IGHV3-15, IGHV3-16, IGHV3-19, IGHV3-20, IGHV3-21, IGHV3-22, IGHV3-23, IGHV3-25, IGHV3-29, IGHV3-30, IGHV3-30-2, IGHV3-32, IGHV3-33, IGHV3-33-2, IGHV3-35, IGHV3-36, IGHV3-37, IGHV3-38, IGHV3-41, IGHV3-42, IGHV3-43, IGHV3-47, IGHV3-48, IGHV3-49, IGHV3-50, IGHV3-52, IGHV3-53, IGHV3-54, IGHV3-57, IGHV3-6, IGHV3-60, IGHV3-62, IGHV3-63, IGHV3-64, IGHV3-65, IGHV3-66, IGHV3-7, IGHV3-71, IGHV3-72, IGHV3-73, IGHV3-74, IGHV3-75, IGHV3-76, IGHV3-79, IGHV3-9, IGHV3OR16-8, IGHV4-28, IGHV4-31, IGHV4-34, IGHV4-39, IGHV4-4, IGHV4-55, IGHV4-59, IGHV4-61, IGHV4-80, IGHV5-51, IGHV5-78, IGHV6-1, IGHV7-27, IGHV7-34-1, IGHV7-40, IGHV7-56, IGHV7-81, IGHVII-1-1, IGHVII-15-1, IGHVII-20-1, IGHVII-22-1, IGHVII-26-2, IGHVII-28-1, IGHVII-30-1, IGHVII-31-1, IGHVII-33-1, IGHVII-40-1, IGHVII-43-1, IGHVII-44-2, IGHVII-46-1, IGHVII-49-1, IGHVII-51-2, IGHVII-53-1, IGHVII-60-1, IGHVII-62-1, IGHVII-65-1, IGHVII-67-1, IGHVII-74-1, IGHVII-78-1, IGHVIII-11-1, IGHVIII-13-1, IGHVIII-16-1, IGHVIII-2-1, IGHVIII-22-2, IGHVIII-25-1, IGHVIII-26-1, IGHVIII-38-1, IGHVIII-44, IGHVIII-47-1, IGHVIII-5-1, IGHVIII-51-1, IGHVIII-5-2, IGHVIII-67-2, IGHVIII-67-3, IGHVIII-67-4, IGHVIII-76-1, IGHVIII-82, and IGHVIV-44-1, wherein the one or more gene segments at the IgK locus or the IgK orphon gene segment is selected from the group consisting of: IGKC, IGKJ1, IGKJ2, IGKJ3, IGKJ4, IGKJ5, IGKV1-12, IGKV1-13, IGKV1-16, IGKV1-17, IGKV1-22, IGKV1-27, IGKV1-32, IGKV1-33, IGKV1-35, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-22, IGKV1D-27, IGKV1D-32, IGKV1D-33, IGKV1D-35, IGKV1D-37, IGKV1D-39, IGKV1D-42, IGKV1D-43, IGKV1D-8, IGKV1OR22-1, IGKV2-10, IGKV2-14, IGKV2-18, IGKV2-19, IGKV2-23, IGKV2-24, IGKV2-26, IGKV2-28, IGKV2-29, IGKV2-30, IGKV2-36, IGKV2-38, IGKV2-4, IGKV2-40, IGKV2D-10, IGKV2D-14, IGKV2D-18, IGKV2D-19, IGKV2D-23, IGKV2D-24, IGKV2D-26, IGKV2D-28, IGKV2D-29, IGKV2D-30, IGKV2D-36, IGKV2D-38, IGKV2D-40, IGKV2OR22-3, IGKV2OR22-4, IGKV3-11, IGKV3-15, IGKV3-20, IGKV3-25, IGKV3-31, IGKV3-34, IGKV3-7, IGKV3D-11, IGKV3D-15, IGKV3D-20, IGKV3D-25, IGKV3D-31, IGKV3D-34, IGKV3D-7, IGKV3OR22-2, IGKV4-1, IGKV5-2, IGKV6-21, IGKV6D-21, IGKV6D-41, and IGKV7-3, wherein the one or more gene segments at the IgL locus or the IgL orphon gene segment is selected from the group consisting of: IGLC1, IGLC2, IGLC3, IGLC4, IGLC5, IGLC6, IGLC7, IGLCOR22-1, IGLJ1, IGLJ2, IGLJ3, IGLJ4, IGLJ5, IGLJ6, IGLJ7, IGLL1, IGLL3, IGLON5, IGLV10-54, IGLV10-67, IGLV11-55, IGLV1-36, IGLV1-40, IGLV1-41, IGLV1-44, IGLV1-47, IGLV1-50, IGLV1-51, IGLV1-62, IGLV2-11, IGLV2-14, IGLV2-18, IGLV2-23, IGLV2-28, IGLV2-33, IGLV2-34, IGLV2-5, IGLV2-8, IGLV3-1, IGLV3-10, IGLV3-12, IGLV3-13, IGLV3-15, IGLV3-16, IGLV3-17, IGLV3-19, IGLV3-2, IGLV3-21, IGLV3-22, IGLV3-24, IGLV3-25, IGLV3-26, IGLV3-27, IGLV3-29, IGLV3-30, IGLV3-31, IGLV3-32, IGLV3-4, IGLV3-6, IGLV3-7, IGLV3-9, IGLV4-3, IGLV4-60, IGLV4-69, IGLV5-37, IGLV5-45, IGLV5-48, IGLV5-52, IGLV6-57, IGLV7-35, IGLV7-43, IGLV7-46, IGLV8-61, IGLV9-49, IGLVI-20, IGLVI-38, IGLVI-42, IGLVI-56, IGLVI-63, IGLVI-68, IGLVI-70, IGLVIV-53, IGLVIV-59, IGLVIV-64, IGLVIV-65, IGLVIV-66-1, IGLVV-58, IGLVV-66, IGLVVI-22-1, IGLVVI-25-1, and IGLVVII-41-1.

16. The method of claim 14, wherein the one or more gene segments at the IgH locus or the IgH orphon gene segment comprises a sequence selected from the group consisting of SEQ ID NOs: 1-174, wherein the one or more gene segments at the IgK locus or the IgK orphon gene segment comprises a sequence selected from the group consisting of SEQ ID NOs: 175-260, or wherein the one or more gene segments at the IgL locus or the IgL orphon gene segment comprises a sequence selected from the group consisting of SEQ ID NOs: 261-350.

17. The method of any one of claims 1-16, wherein the level of expression of Ig is the sum of the expression levels of more than one gene segment of the IgH locus, IgK locus, and/or IgL locus and/or more than one IgH orphon gene segment, IgK orphon gene segment, and/or IgK orphon gene segment.

18. The method of claim 17, wherein the level of expression of Ig is the sum of the expression levels of all the gene segments of the IgH locus and all the IgH orphon gene segments.

19. The method of claim 17, wherein the level of expression of Ig is the sum of (i) the levels of expression of all the gene segments of the IgH locus and all the IgH orphon gene segments, (ii) the levels of expression of all the gene segments of the IgK locus and all the IgK orphon gene segments, and (iii) the levels of expression of all the gene segments of the IgL locus and all the IgL orphon gene segments.

20. The method of any one of claims 1-19, comprising measuring the level of expression of Ig and the level of expression of FCGR2B in the sample.

21. The method of any one of claims 1-20, further comprising measuring the level of expression of one of more genes listed in Table 4, optionally, wherein the level of expression of two, three, four, five, six, seven, eight, nine, ten, or more genes listed in Table 4 are measured.

22. The method of any one of claims 1-21, wherein the reference level is a reference level of Ig expression.

23. The method of any one of claims 1-22, wherein the measured level of Ig expression and/or the measured level of FCGR2B expression is at least 2-fold greater than the reference level.

24. The method of any one of claims 1-23, wherein the measured level of Ig expression and/or the measured level of FCGR2B expression is at least 3-fold greater than the reference level.

25. The method of any one of claims 1-24, wherein the measured level of Ig expression and/or the measured level of FCGR2B expression is at least 4-fold greater than the reference level.

26. The method of any one of claims 1-22, wherein the reference level is a cutoff correlative with a % specificity of at least 50% and a % sensitivity of at least 50%, as determined by a receiver operating characteristic (ROC) curve, optionally, wherein the ROC curve is based on (i) the distribution of Ig expression levels and/or FCGR2B expression levels of responders and (ii) the distribution of Ig expression levels and/or FCGR2B expression levels of non-responders.

27. The method of any one of claims 1-22, wherein the reference level is a cutoff correlative with a % specificity of at least 75% and a % sensitivity of at least 75%, as determined by a receiver operating characteristic (ROC) curve, optionally, wherein the ROC curve is based on (i) the distribution of Ig expression levels and/or FCGR2B expression levels of responders and (ii) the distribution of Ig expression levels and/or FCGR2B expression levels of non-responders.

28. The method of any one of claims 1-27, wherein the subject (i) has previously been treated for multiple myeloma or (ii) has previously been diagnosed with multiple myeloma or (iii) is a human patient having or suspected of having multiple myeloma, refractory multiple myeloma, or relapsed multiple myeloma.

29. The method of any one of claims 1-28, wherein measuring the level of expression of Ig and/or FCGR2B in a sample comprises (i) amplifying a fragment of a human Ig mRNA or human FCGR2B mRNA; (ii) measuring the Ig expression level in the cell using a microarray platform that map to genes encoding Ig-related proteins; or (iii) measuring the Ig protein load in the cells with an anti-human Ig antibody.

30. The method of any one of claims 1-29, wherein the measuring comprises amplifying a fragment of a human Ig mRNA and/or human FCGR2B mRNA.

31. The method of claim 30, wherein the amplifying is by polymerase chain reaction (PCR) or RT-PCR.

32. The method of any one of claims 1-31, wherein the measuring comprises measuring the presence, absence, or amount of a human Ig protein in the sample.

33. The method of claim 32, wherein the measuring uses an antibody that specifically binds to a human Ig protein, a human FCGR2B, or a human protein encoded by a gene listed in Table 4.

34. The method of claim 33, wherein the measuring is by an ELISA assay, a western blot assay, or an immunohistochemical assay.

35. A kit comprising one or more binding agents to an Ig gene or gene product, optionally an IgH, IgK or IgL gene segment or gene segment product, or an IgH, IgK, or IgL orphon gene segment or gene segment product, and a binding agent to FCGR2B gene or gene product.

36. A kit comprising (i) one or more binding agents to an Ig gene or gene product, optionally an IgH, IgK or IgL gene segment or gene segment product, or an IgH, IgK, or IgL orphon gene segment or gene segment product, or a binding agent to FCGR2B gene or gene product and (ii) at least one binding agent to a gene or gene product listed in Table 4.

37. The kit of claim 35, further comprising at least one binding agent to a gene or gene product listed in Table 4.

38. The kit of any one of claims 35 to 37, further comprising a proteasome inhibitor.

39. The kit of any one of claims 35-38, further comprising a reagent that produces a signal indicative of a reference level.

40. The kit of any one of claims 35-39, wherein the binding agent is a compound that binds to a nucleic acid molecule, optionally, wherein the binding agent is a nucleic acid molecule.

41. The kit of any one of claims 35 to 40, wherein the binding agent is a compound that binds to a protein, optionally, wherein the binding agent is an antibody, an antigen binding fragment thereof, or an antibody derivative.

42. A method of treating a tumor in a subject, comprising:
    a) measuring the level of expression of one or more genes listed in Table 4, in a sample obtained from the subject, wherein the sample comprises a cell from the tumor; and
    b) administering to the subject an effective amount of a proteasome inhibitor, when (i) the level of expression of the one or more genes listed in Table 4 in the sample greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

43. A method of treating a tumor in a subject from which a sample was obtained, wherein the level of expression of one or more genes or gene products listed in Table 4 has been measured from the sample, the method comprising the step of administering to the subject an effective amount of a proteasome inhibitor, when (i) the level of expression of the one or more genes listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

44. A method of determining a treatment regimen for a subject with a tumor, comprising:
    a) measuring the level of expression of one or more genes or gene products listed in Table 4 in a sample obtained from the subject, wherein the sample comprises a cell from the tumor, and
    b) selecting a treatment regimen comprising administration of a proteasome inhibitor, when (i) the level of expression of the one or more genes listed in Table 4 in the sample is greater than a reference level, and the change in gene expression level for the one or more genes or gene products is denoted in Table 4 as "up", or (ii) the level of expression of the one or more genes or gene products listed in Table 4 in the sample is less than a reference level, and the change in gene expression level for the one or more genes or gene products is denoted in Table 4 as "down", or (iii) both (i) and (ii).

45. The method of any one of claims 42-44, wherein the proteasome inhibitor is selected from the group consisting of carfilzomib, bortezomib, disulfiram, and oprozomib.

46. The method of any one of claims 42-45, wherein the tumor is a hematological tumor, optionally, a hematological tumor derived from lymphoid cells.

47. The method of claim 46, wherein the hematological tumor is a lymphoma, optionally, a non-Hodgkin's lymphoma.

48. The method of claim 47, wherein the a non-Hodgkin's lymphoma is mantel cell lymphoma.

49. The method of claim 46, wherein the hematological tumor is a multiple myeloma.

50. The method of claim 49, wherein the multiple myeloma is smouldering myeloma, relapsed multiple myeloma, or refractory myeloma.

51. The method of any one of claims 42-50, wherein the level of expression of the one or more genes or gene products in Table 4 is measured in CD138-positive tumor cells obtained from the subject.

52. The method of claim 51, comprising extracting RNA from the CD138-positive tumor cells.

53. The method of any one of claims 42-52, wherein the sample comprises bone marrow cells, blood, serum, or a biopsy sample.

54. The method of claim 53, comprising contacting antibodies specific for a gene product encoded by the one or more genes in Table 4 with the sample comprising bone marrow cells.

55. The method of any one of claims 42-54, further comprising measuring the level of expression of Ig and/or FCGF2B in the sample.

56. The method of claim 55, further comprising measuring the level of expression of one or more gene segments of the IgH locus, IgK locus, or IgL locus, or an IgH orphon gene segment, an IgK orphon gene segment, or an IgL orphon gene segment, or a combination thereof.

57. The method of claim 56, wherein the one or more genes of the IgH locus or the IgH orphon gene segment is/are selected from the group consisting of the group of gene segments of the IgH locus in claim 15, wherein the one or more gene segments of the IgK locus or the IgK orphon gene segment is/are selected from the group consisting of the group of gene segments of the IgK locus in claim 15, or wherein the one or more gene segments at the IgL locus or the IgL orphon gene segment is/are selected from the group consisting of the group of gene segments of the IgL locus in claim 15.

58. The method of claim 56, wherein the one or more gene segments at the IgH locus or the IgH orphon gene segment comprises a sequence selected from the group consisting of SEQ ID NOs: 1-174, wherein the one or more gene segments at the IgK locus or the IgK orphon gene segment comprises a sequence selected from the group consisting of SEQ ID NOs: 175-260, or wherein the one or more gene segments at the IgL locus or the IgL orphon gene segment comprises a sequence selected from the group consisting of SEQ ID NOs: 261-350.

59. The method of any one of claims 42 to 58, wherein the level of expression of Ig is the sum of the expression levels of more than one gene segment of the IgH locus, IgK locus, and/or IgL locus and/or more than one IgH orphon gene segment, IgK orphon gene segment, and/or IgK orphon gene segment.

60. The method of claim 59, wherein the level of expression of Ig is the sum of the expression levels of all the gene segments of the IgH locus and all the IgH orphon gene segments.

61. The method of any one of claims 42-60, wherein the level of expression of Ig is the sum of (i) the levels of expression of all the gene segments of the IgH locus and all the IgH orphon gene segments, (ii) the levels of expression of all the gene segments of the IgK locus and all the IgK orphon gene segments, and (iii) the levels of expression of all the gene segments of the IgL locus and all the IgL orphon gene segments.

62. The method of any one of claims 42 to 61, comprising measuring the level of expression of two of more genes listed in Table 4, optionally, wherein the level of expression of three, four, five, six, seven, eight, nine, ten, or more genes listed in Table 4 are measured.

63. The method of any one of claims 42-62, wherein the reference level is a reference value of expression level of the one or more genes.

64. The method of any one of claims 42-63, wherein the measured level of expression of the one or more genes is at least 2-foldless than or greater than the reference level.

65. The method of any one of claims 42-64, wherein the measured level of expression of the one or more genes is at least 3-fold less than or greater than,the reference level.

66. The method of any one of claims 42-65, wherein the measured level of expression of the one or more genes is at least 4-fold less than or greater than the reference level.

67. The method of any one of claims 42-66, wherein the reference level is a cutoff correlative with a % specificity of at least 50% and a % sensitivity of at least 50%, as determined by a receiver operating characteristic (ROC) curve, optionally, wherein the ROC curve is based on (i) the distribution of expression levels of responders, wherein the expression levels are the expression levels of the one or more genes listed in Table 4 and (ii) the distribution of expression levels of non-responders, wherein the expression levels are the expression levels of the one or more genes listed in Table 4.

68. The method of any one of claims 42-67, wherein the reference level is a cutoff correlative with a % specificity of at least 75% and a % sensitivity of at least 75%, as determined by a receiver operating characteristic (ROC) curve, optionally, wherein the ROC curve is based on (i) the distribution of expression levels of responders, wherein the expression levels are the expression levels of the one or more genes listed in Table 4 and (ii) the distribution of expression levels of non-responders, wherein the expression levels are the expression levels of the one or more genes listed in Table 4.

69. The method of any one of claims 42-67, wherein the subject (i) has previously been treated for multiple myeloma or (ii) has previously been diagnosed with multiple myeloma or (iii) is a human patient having or suspected of having multiple myeloma, refractory multiple myeloma, or relapsed multiple myeloma.

70. The method any one of claims 42-69, comprising (i) amplifying a fragment of a human mRNA encoded by the one or more genes; (ii) measuring the expression level in the cell using a microarray platform that map to the one or more genes; or (iii) measuring the protein load in the cells with an antibody specific for the protein product encoded by the one or more genes.

71. The method of any one of claims 42-70, comprising amplifying a fragment of a human mRNA encoded by the one or more genes.

72. The method of claim 71, wherein the amplifying is by polymerase chain reaction (PCR) or RT-PCR.

73. The method of any one of claims 42-72, comprising measuring the presence, absence, or amount of a human protein encoded by the one or more genes in the test sample.

74. The method of claim 73, comprising the use of an antibody that specifically binds to a gene produce encoded by a gene listed in Table 4.

75. The method of claim 74, comprising measuring by an ELISA assay, a western blot assay, or an immunohistochemical assay.

76. A kit comprising at least a first binding agent and a second binding agent, wherein the first binding agent binds to a first gene or gene product encoded by a first gene listed in Table 4, wherein the second binding agent binds to a second gene or gene product encoded by a second gene listed in Table 4, wherein the first gene is different from the second gene.

77. The kit of claim 76 further comprising a proteasome inhibitor.

78. The kit of claim 76 or 77, further comprising a binding agent to an Ig or FCGR2B.

79. The kit of any one of claims 76 to 78 further comprising a reagent that produces a signal indicative of a reference level.

80. The kit of any one of claims 76 to 79, wherein the binding agent is a compound that binds to a nucleic acid molecule, optionally, wherein the binding agent is a nucleic acid molecule.

81. The kit of any one of claims 76 to 80, wherein the binding agent is a compound that binds to a protein, optionally, wherein the binding agent is an antibody, an antigen binding fragment thereof, or an antibody derivative.

82. A computer readable-storage medium having stored thereon a plurality of reference levels or ranges of reference levels, each reference level or range of reference levels corresponding to (i) an expression level of Ig or (ii) an expression level of FCGR2B, or (iii) an expression level of a gene listed in Table 4, or (iv) a combination thereof; and a data value that is an expression level of Ig and/or an expression level of FCGR2B and/or an expression level of a gene listed in Table 4, measured from a cell from a sample from a patient.

83. The computer readable-storage medium of claim 82, wherein the data value that is the expression level of Ig is the sum of the expression levels of more than one gene segment of the IgH, IgK, and/or IgL locus, optionally, wherein the expression level of Ig is indicative of a responder or non-responder.

84. A computer readable-storage medium having stored thereon (I) a first set of data values and a second set of data values, wherein each data value of the first set is an expression level of Ig determined from a sample obtained from a responder and each data value of the second set is an expression level of Ig determined from a sample obtained from a non-responder; (II) a receiver operating characteristic (ROC) curve based on a first set of data values and a second set of data values, wherein each data value of the first set is an expression level of Ig determined from a sample obtained from a responder and each data value of the second set is an expression level of Ig determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

85. A computer readable-storage medium having stored thereon (I) a first set of data values and a second set of data values, wherein each data value of the first set is an expression level of FCGR2B determined from a sample obtained from a responder and each data value of the second set is an expression level of FCGR2B deteremined from a sample obtained from a non-responder; (II) a receiver operating characteristic (ROC) curve based on a first set of data values and a second set of data values, wherein each data value of the first set is an expression level of FCGR2B determined from a sample obtained from a responder and each data value of the second set is an expression level of FCGR2B deteremined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

86. A computer readable-storage medium having stored thereon (I) a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; (II) a receiver operating characteristic (ROC) curve based on a first set of data values and a second set of data values, wherein each data value of the first set is an expression level of a gene listed in Table 4 determined from a sample obtained from a responder and each data value of the second set is an expression level of a gene listed in Table 4 determined from a sample obtained from a non-responder; or (III) a table listing (a) a plurality of cut-off points on the ROC curve of (II), (b) the % sensitivity associated with each cut-off point of (a), and (c) the % specificity associated with each cut-off point of (a).

87. A computer readable storage medium comprising two or more of the computer storage media of claims 84-86.

88. A system comprising: a processor; a memory device coupled to the processor, and machine readable instructions stored on the memory device, wherein the machine readable instructions, when executed by the processor, cause the processor to:
  i. receive a data value, α, relating to a test level of Ig expression from a sample obtained from a test subject; and
  ii. display an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

89. A system comprising: a processor; a memory device coupled to the processor, and machine readable instructions stored on the memory device, wherein the machine readable instructions, when executed by the processor, cause the processor to:
  i. receive a data value, α, relating to a test level of FCGR2B expression from a sample obtained from a test subject; and
  ii. display an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

90. A system comprising: a processor; a memory device coupled to the processor, and machine readable instructions stored on the memory device, wherein the machine readable instructions, when executed by the processor, cause the processor to:
  i. receive a data value, α, relating to a test level of expression of a gene listed in Table 4, wherein the change in gene expression level for the gene is denoted in Table 4 as "up", from a sample obtained from a test subject; and
  ii. display an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

91. A system comprising: a processor; a memory device coupled to the processor, and machine readable instructions stored on the memory device, wherein the machine readable instructions, when executed by the processor, cause the processor to:
  i. receive a data value, α, relating to a test level of expression of a gene listed in Table 4, wherein the change in gene expression level for the gene is denoted in Table 4 as "down", from a sample obtained from a test subject; and
  ii. display an output relating to treating the subject for multiple myeloma with a proteasome inhibitor, when α is less than β, a cutoff correlative with a % specificity of at least 50% and a % sensitivity of at least 50%, as determined by a receiver operating characteristic (ROC) curve.

92. A computer-readable storage medium having stored thereon machine-readable instructions executable by a processor, comprising:
  i. instructions for receiving a data value, α, relating to a test level of Ig expression from a sample obtained from a test subject; and
  ii. instructions for displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

93. A computer-readable storage medium having stored thereon machine-readable instructions executable by a processor, comprising:
  i. instructions for receiving a data value, α, relating to a test level of FCGR2B expression from a sample obtained from a test subject; and
  ii. instructions for displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

94. A computer-readable storage medium having stored thereon machine-readable instructions executable by a processor, comprising:
  i. instructions for receiving a data value, α, relating to a test level of expression of a gene listed in Table 4 from a sample obtained from a test subject, wherein the change in gene expression level for the gene is denoted in Table 4 as "up"; and
  ii. instructions for displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

95. A computer-readable storage medium having stored thereon machine-readable instructions executable by a processor, comprising:
  (i) instructions for receiving a data value, α, relating to a test level of expression of a gene listed in Table 4 from a sample obtained from a test subject, wherein the change in gene expression level for the gene is denoted in Table 4 as "down"; and
  (ii) instructions for displaying an output relating to treating the subject for multiple myeloma with a proteasome inhibitor, when α is less than β, a cutoff correlative with a % specificity of at least 50% and a % sensitivity of at least 50%, as determined by a receiver operating characteristic (ROC) curve.

96. A method implemented by a processor in a computer, the method comprising the steps of:
   i. receiving a data value, α, relating to a test level of Ig expression from a sample obtained from a test subject; and
   ii. displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

97. A method implemented by a processor in a computer, the method comprising the steps of:
   i. receiving a data value, α, relating to a test level of FCGR2B expression from a sample obtained from a test subject; and
   ii. displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

98. A method implemented by a processor in a computer, the method comprising the steps of:
   i. receiving a data value, α, relating to a test level of expression of a gene listed in Table 4 from a sample obtained from a test subject, wherein the change in gene expression level for the gene is denoted in Table 4 as "up"; and
   ii. displaying an output relating to treating the subject for multiple myeloma with a proteasome inhibitor, when α is greater than β, a cutoff correlative with a % specificity of at least 50% and a % sensitivity of at least 50%, as determined by a receiver operating characteristic (ROC) curve.

99. A method implemented by a processor in a computer, the method comprising the steps of:
   (i) receiving a data value, α, relating to a test level of expression of a gene listed in Table 4 from a sample obtained from a test subject, wherein the change in gene expression level for the gene is denoted in Table 4 as "down"; and
   (ii) displaying an output relating to treating the subject for multiple myeloma with a proteasome inhibitor, when α is less than β, a cutoff correlative with a % specificity of at least 50% and a % sensitivity of at least 50%, as determined by a receiver operating characteristic (ROC) curve.

The following examples serve only to illustrate the invention or provide background information relating to the invention. The following examples are not intended to limit the scope of the invention in any way.

EXAMPLES

Several therapies for multiple myeloma (MM) are now approved and many more are in development, promising improved outcomes for patients with this incurable cancer. With expanding treatment options, however, comes a pressing need to pair each patient with the most efficacious and safe treatment. Proteasome inhibitors (PIs), such as carfilzomib and bortezomib, have become a standard therapy across all lines of MM therapy. Despite extensive study, the mechanism of selective tumor cell death following proteasome inhibition is poorly understood. However, the uniquely high sensitivity of myeloma cells to PI, the uniquely high burden of protein (immunoglobulin) secretion these cells experience, and the key role of the proteasome in maintaining protein homeostasis, together point toward a unifying model in which protein load drives PI sensitivity. This simple model is supported by published studies of murine and human myeloma cell lines (Meister et al. & Bianchi et al.). As part of company-sponsored Phase II & III clinical trials of PIs, CD138+ tumor cells collected during patient screening were banked for comprehensive genomic analyses. Patient samples banked on bortezomib trials were utilized in now-published microarray-based RNA studies (Mulligan et al.), while samples from carfilzomib trials are currently being used for NGS-based DNA and RNA studies. Here, examining the early carfilzomib data along with publically-available bortezomib data, the inventors demonstrate a strong association between higher immunoglobulin expression and sensitivity to each compound (Wilcoxon P-value=$3\times10^{-3}$ and P-value=$2\times10^{-4}$, respectively). In fact, using IGH expression alone, the inventors were able to classify response with 55% sensitivity and 91% specificity for the carfilzomib training data set. As expected for a bona fide predictive biomarker of PI, an association between IG expression and response was not found in patients treated with single agent dexamethasone (Wilcoxon P-value=0.82). Median time to progression for IGH-high carfilzomib patients was 6-fold longer than for IGH-low carfilzomib patients (7.6 months vs. 1.4 months; log-rank P-value=0.003). This is the first report that high levels of IG expression correlate with response to PIs and therefore IG expression represents, to our knowledge, the first validated biomarker for this important class of anti-tumor agents.

Example 1: Bortezomib Data Analysis

Publicly available RNA microarray data in tab-delimited text format were downloaded from the Gene Expression Omnibus (GEO ID: GSE9782). These data, originally reported in a publication by Mulligan et al., represent normalized, probe-level measurements of mRNA abundance in multiple myeloma tumor cells (CD138+ selected) collected from patients prior to treatment with either single-agent bortezomib or single-agent dexamethasone on Millennium's Phase 2 and Phase 3 clinical trials.

A list of 55 probes from this Affymetrix microarray platform that map to genes encoding immunoglobulin (Ig)-related proteins was obtained from Rody et al. Addition File 5. This example tested for an association between normalized intensity of each of these 55 probes and bortezomib response, which was labeled as "PGx_Responder=R" in the dataset. Of these, 13 showed a significant correlation (Wilcoxon P-value<=0.05) between higher expression values and response on the bortezomib arms of the studies: 211798_x_at, 211881_x_at, 216365_x_at, 216560_x_at, 217148_x_at, 217179_x_at, 217227_x_at, 217258_x_at, 211639_x_at, 216491_x_at, 211649_x_at, 216510_x_at, and 211637_x_at. The finding of 13 significant associations is far more than expected by chance (Binomial P-value=$2\times10^{-6}$). None of the 55 probes showed the opposite effect. It is not surprising that many probes are not associated, given that some map to rarer, patient-specific portions of the Ig loci and that others map to regions that are unusually highly-expressed, and therefore not well-measured with microarray technology (i.e., their fluorescence is likely to be saturated).

Figure 1B:
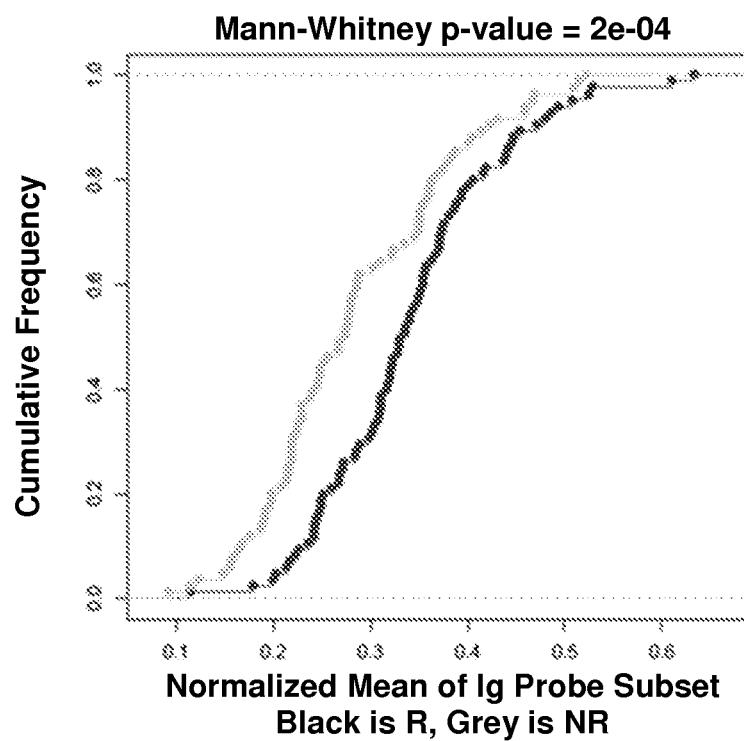
Figure 2A:
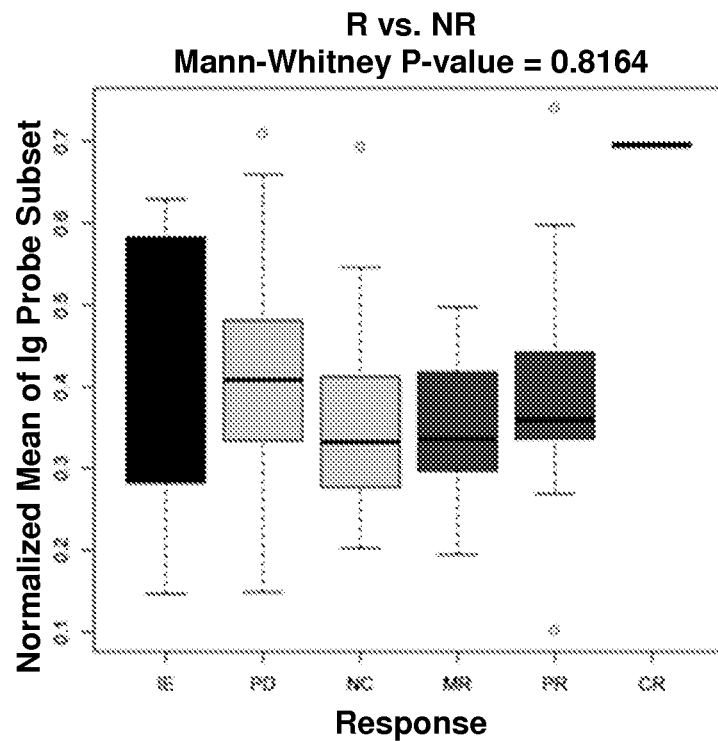
FIGS. 2A and 2B are graphs demonstrating the lack of association between IG expression and dexamethasone response. IE, response not evaluable; PD, progressive disease; no change, NC; minimal response, MR; partial response, PR; complete response, CR.
Figure 2B:
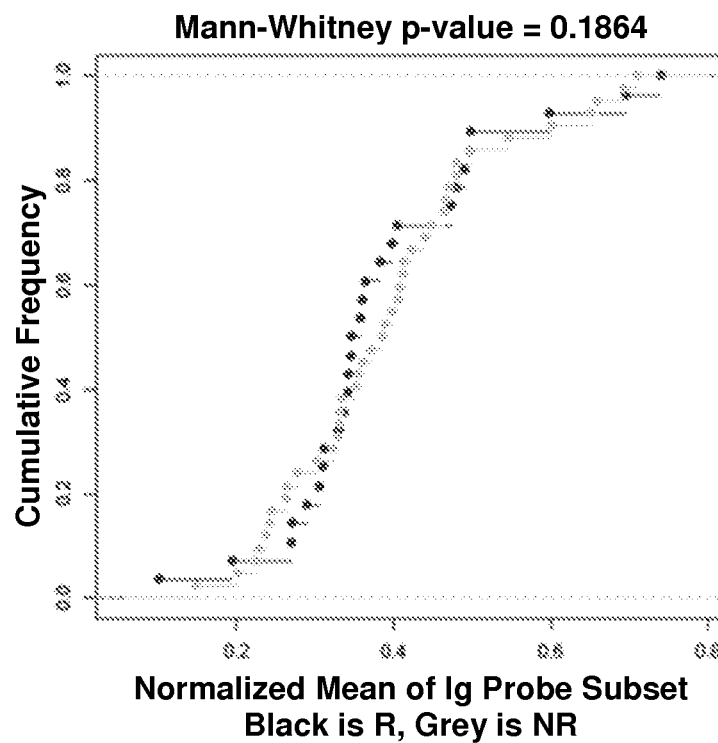

The 13 significantly-associated probes were each normalized to a [0, 1] scale and the mean was computed, yielding our combined Ig expression score. The combined score is very strongly associated with bortezomib response (Wilcoxon P-value=$2\times10^{-4}$; FIGS. 1A and 1B), but exhibits no association with response to dexamethasone (Wilcoxon P-value=0.82; FIGS. 2A and 2B). Patients were classified as achieving complete response (CR), partial response (PR), minimal response (MR), no change (NC), or progressive disease (PD), using European Group for Bone Marrow Transplantation criteria. In brief, PD requires 25% increase in paraprotein, whereas MR, PR, and CR require at least 25%, 50%, and 100% decreases, respectively. Further illustrating the specificity of this marker for predicting PI response, of the 55 Ig probes selected, only one showed an association with dexamethasone response (which is roughly what is expected by chance; Binomial P-value=0.23) and the P-value itself was only marginally significant (Wilcoxon P-value=0.0495).

Various mean IG expression cutoffs were considered to maximize the clinical utility of a potential diagnostic test. Ultimately, a cutoff of 0.29 (defining "IG-High">=0.29 and "IG-Low"<0.29) was chosen, predicting response in the training data with 71% sensitivity and 62% specificity. This same cutoff was then applied to time-to-progression (TTP) data for these patients, finding that IG-High patients in this cohort have a 1.4-fold longer median TTP than IG-Low patients (8.4 months vs. 6.0 months; log-rank P-value=0.025).

Example 2: Carfilzomib Data Analysis

Bone marrow samples were aspirated from patients enrolled on Onyx-sponsored Phase 2 trials (NCT00511238, NCT00530816, and NCT00721734) prior to treatment with single-agent carfilzomib. Myeloma tumor cells were isolated by EasySep® immunomagnetic bead-based CD138+ selection (StemCell Technologies), re-suspended in TRIzol (Life Technologies) and frozen at −80° F. RNA was extracted from these samples with the PureLink RNA kit from Life Technologies (Cat #12183018A), following the recommended protocol for cells in TRIzol suspension, including the optional on-column DNase treatment. Elution volumes ranged from 75 µl-30 µl depending on the total number of cells going into isolation. ERCC control sequences from Life Technologies (ERCC ExFold RNA Spike-In Mix; Cat #4456739) were spiked in to all total RNA samples of sufficient quantity (Nanodrop yield>=150 ng) and quality (Bioanalyzer RIN>=7.0). For 500 ng input libraries, 1 µl of a 1:100 dilution of Mix 1 was added to each total RNA sample and for 150 ng input libraries, 3 µl of a 1:1000 dilution of Mix 1 was added to each total RNA sample. The resulting material was used to construct RNA-Seq libraries with Illumina's TruSeq RNA sample prep kit v2 (Cat #RS-122-2001), with PolyA selection included as the first step. Libraries were sequenced on Illumina's HiSeq 2000 with a target of 70 million fragments using 100×100 bp paired-end sequencing to generate 140 million reads per sample and the resulting raw data was QC-ed with metrics implemented in OmicSoft Array Studio v6.1.

Raw sequence reads were aligned and expression of genes & isoforms were quantified with a customized pipeline also built in Array Studio v6.1 [Jun]. This pipeline accepts Illumina adapter-stripped, paired-end reads that are trimmed at the 5' end if a base reaches PHRED quality score Q2 or lower. All reads are aligned to the transcriptome, which consists of the RefGene annotation of human hg19 supplemented with the more rich Ig loci annotations available from ENSEMBL. Reads aligned with mismatches and unaligned reads are subsequently aligned to the entire human genome, searching for novel exon junctions. Reads that remain unaligned are then aligned to the newly identified exon junctions. Alignments to the different references are compared and the highest scoring alignment is retained, or in the event of a tie, the transcriptome alignment is preferentially kept. Finally, all transcriptome alignment locations are translated to genomic coordinates to estimate the expected number of mappings per gene/isoform using the EM algorithm [Dempster]. The EM algorithm assigns reads with multiple alignment locations to an isoform by calculating the conditional probability of a read aligning to a specific isoform, given all other alignments. Weighting the total number of aligned reads with this probability yields posterior expected read counts for each transcript. The EM counts are normalized by the length of the genes/isoforms and number of reads in a library to yield FPKM values (Fragments Per Kilobase per Million reads). Between-sample normalization is achieved by $75^{th}$ quantile normalization, where each sample is scaled by the median of $75^{th}$ quantiles from all samples to yield quantile-normalized FPKM or "FPKQ" values.

The FPKQ values corresponding to each "gene" of the three Ig loci, IGH (immunoglobulin heavy locus), IGK (immunoglobulin kappa locus) and IGL (immunoglobulin lambda locus), were summed to produce locus-level expression estimates.

For IGH, this included the following genes: IGHA1, IGHA2, IGHD, IGHD1-1, IGHD1-14, IGHD1-20, IGHD1-26, IGHD1-7, IGHD2-15, IGHD2-2, IGHD2-21, IGHD2-8, IGHD3-10, IGHD3-16, IGHD3-22, IGHD3-3, IGHD3-9, IGHD4-11, IGHD4-17, IGHD4-23, IGHD4-4, IGHD5-12, IGHD5-18, IGHD5-24, IGHD5-5, IGHD6-13, IGHD6-19, IGHD6-25, IGHD6-6, IGHD7-27, IGHE, IGHEP1, IGHEP2, IGHG1, IGHG2, IGHG3, IGHG4, IGHGP, IGHJ1, IGHJ1P, IGHJ2, IGHJ2P, IGHJ3, IGHJ3P, IGHJ4, IGHJ5, IGHJ6, IGHM, IGHMBP2, IGHV1-12, IGHV1-14, IGHV1-17, IGHV1-18, IGHV1-2, IGHV1-24, IGHV1-3, IGHV1-45, IGHV1-46, IGHV1-58, IGHV1-67, IGHV1-68, IGHV1-69, IGHV1-8, IGHV1OR21-1, IGHV2-10, IGHV2-26, IGHV2-5, IGHV2-70, IGHV2OR16-5, IGHV3-11, IGHV3-13, IGHV3-15, IGHV3-16, IGHV3-19, IGHV3-20, IGHV3-21, IGHV3-22, IGHV3-23, IGHV3-25, IGHV3-29, IGHV3-30, IGHV3-30-2, IGHV3-32, IGHV3-33, IGHV3-33-2, IGHV3-35, IGHV3-36, IGHV3-37, IGHV3-38, IGHV3-41, IGHV3-42, IGHV3-43, IGHV3-47, IGHV3-48, IGHV3-49, IGHV3-50, IGHV3-52, IGHV3-53, IGHV3-54, IGHV3-57, IGHV3-6, IGHV3-60, IGHV3-62, IGHV3-63, IGHV3-64, IGHV3-65, IGHV3-66, IGHV3-7, IGHV3-71, IGHV3-72, IGHV3-73, IGHV3-74, IGHV3-75, IGHV3-76, IGHV3-79, IGHV3-9, IGHV3OR16-8, IGHV4-28, IGHV4-31, IGHV4-34, IGHV4-39, IGHV4-4, IGHV4-55, IGHV4-59, IGHV4-61, IGHV4-80, IGHV5-51, IGHV5-78, IGHV6-1, IGHV7-27, IGHV7-34-1, IGHV7-40, IGHV7-56, IGHV7-81, IGHVII-1-1, IGHVII-15-1, IGHVII-20-1, IGHVII-22-1, IGHVII-26-2, IGHVII-28-1, IGHVII-30-1, IGHVII-31-1, IGHVII-33-1, IGHVII-40-1, IGHVII-43-1, IGHVII-44-2, IGHVII-46-1, IGHVII-49-1, IGHVII-51-2, IGHVII-53-1, IGHVII-60-1, IGHVII-62-1, IGHVII-65-1, IGHVII-67-1, IGHVII-74-1, IGHVII-78-1, IGHVIII-11-1, IGHVIII-13-1, IGHVIII-16-1, IGHVIII-2-1, IGHVIII-22-2, IGHVIII-25-1, IGHVIII-26-1, IGHVIII-38-1, IGHVIII-44, IGHVIII-47-1, IGHVIII-5-1, IGHVIII-51-1, IGHVIII-5-2, IGHVIII-67-2, IGHVIII-67-3, IGHVIII-67-4, IGHVIII-76-1, IGHVIII-82 and IGHVIV-44-1.

For IGK, this included the following genes: IGKC, IGKJ1, IGKJ2, IGKJ3, IGKJ4, IGKJ5, IGKV1-12, IGKV1-13, IGKV1-16, IGKV1-17, IGKV1-22, IGKV1-27, IGKV1-32, IGKV1-33, IGKV1-35, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-22, IGKV1D-27, IGKV1D-32, IGKV1D-33, IGKV1D-35, IGKV1D-37, IGKV1D-39, IGKV1D-42, IGKV1D-43, IGKV1D-8, IGKV1OR22-1, IGKV2-10, IGKV2-14, IGKV2-18, IGKV2-19, IGKV2-23, IGKV2-24, IGKV2-26, IGKV2-28, IGKV2-29, IGKV2-30, IGKV2-36, IGKV2-38, IGKV2-4, IGKV2-40, IGKV2D-10, IGKV2D-14, IGKV2D-18, IGKV2D-19, IGKV2D-23, IGKV2D-24, IGKV2D-26, IGKV2D-28, IGKV2D-29, IGKV2D-30, IGKV2D-36, IGKV2D-38, IGKV2D-40, IGKV2OR22-3, IGKV2OR22-4, IGKV3-11, IGKV3-15, IGKV3-20, IGKV3-25, IGKV3-31, IGKV3-34, IGKV3-7, IGKV3D-11, IGKV3D-15, IGKV3D-20, IGKV3D-25, IGKV3D-31, IGKV3D-34, IGKV3D-7, IGKV3OR22-2, IGKV4-1, IGKV5-2, IGKV6-21, IGKV6D-21, IGKV6D-41, and IGKV7-3.

For IGL, this included the following genes: IGLC1, IGLC2, IGLC3, IGLC4, IGLC5, IGLC6, IGLC7, IGLCOR22-1, IGLJ1, IGLJ2, IGLJ3, IGLJ4, IGLJ5, IGLJ6, IGLJ7, IGLL1, IGLL3, IGLON5, IGLV10-54, IGLV10-67, IGLV11-55, IGLV1-36, IGLV1-40, IGLV1-41, IGLV1-44, IGLV1-47, IGLV1-50, IGLV1-51, IGLV1-62, IGLV2-11, IGLV2-14, IGLV2-18, IGLV2-23, IGLV2-28, IGLV2-33, IGLV2-34, IGLV2-5, IGLV2-8, IGLV3-1, IGLV3-10, IGLV3-12, IGLV3-13, IGLV3-15, IGLV3-16, IGLV3-17, IGLV3-19, IGLV3-2, IGLV3-21, IGLV3-22, IGLV3-24, IGLV3-25, IGLV3-26, IGLV3-27, IGLV3-29, IGLV3-30, IGLV3-31, IGLV3-32, IGLV3-4, IGLV3-6, IGLV3-7, IGLV3-9, IGLV4-3, IGLV4-60, IGLV4-69, IGLV5-37, IGLV5-45, IGLV5-48, IGLV5-52, IGLV6-57, IGLV7-35, IGLV7-43, IGLV7-46, IGLV8-61, IGLV9-49, IGLVI-20, IGLVI-38, IGLVI-42, IGLVI-56, IGLVI-63, IGLVI-68, IGLVI-70, IGLVIV-53, IGLVIV-59, IGLVIV-64, IGLVIV-65, IGLVIV-66-1, IGLVV-58, IGLVV-66, IGLVVI-22-1, IGLVVI-25-1, and IGLVVII-41-1.

Patients with a best overall response of minimal response (MR) or better (i.e., MR, partial response [PR], very good partial response [VGPR] and complete response [CR]) were grouped into a responder category (N=27; abbreviated as "R") and patients with a best overall response of stable disease (SD) or worse (i.e., SD and progressive disease [PD]) were grouped into a non-responder category (N=33; abbreviated as "NR"). Associations between response and expression of IGH, IGK and IGL loci were then tested with the Wilcoxon test, yielding the following results (Table 1):

TABLE 1

| IG Locus | Wilcoxon P-Value |
| --- | --- |
| IGH | 0.003 |
| IGK | 0.49 |
| IGL | 0.05 |
| Max (IGK, IGL) | 0.13 |

Figure 3A:
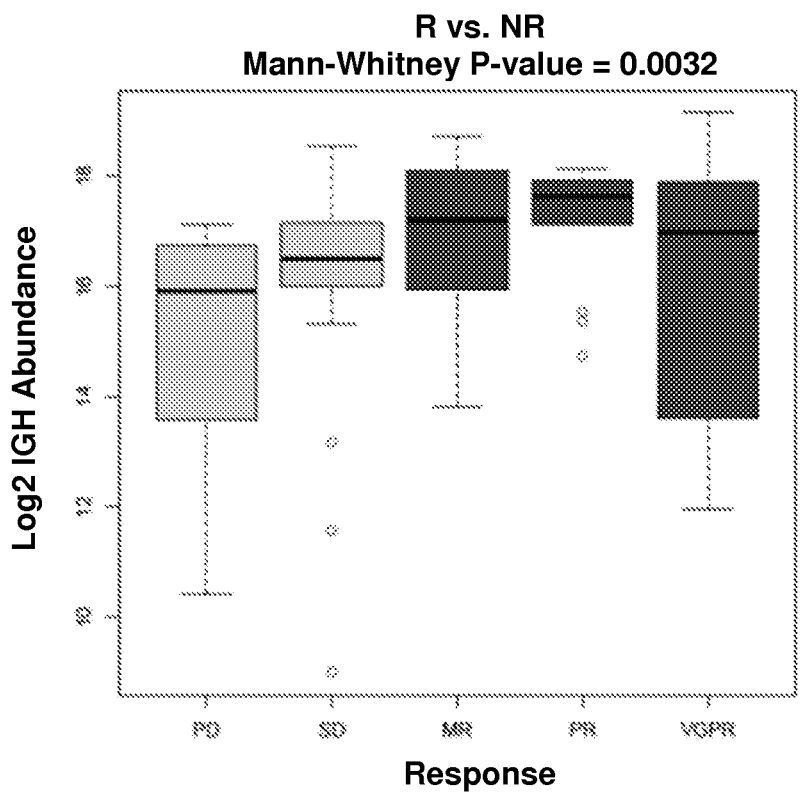
FIGS. 3A and 3B are graphs demonstrating the association between IGH expression and carfilzomib response. PD, progressive disease; stable disease, SD; minimal response, MR; partial response, PR; very good partial response, VGPR.
Figure 3B:
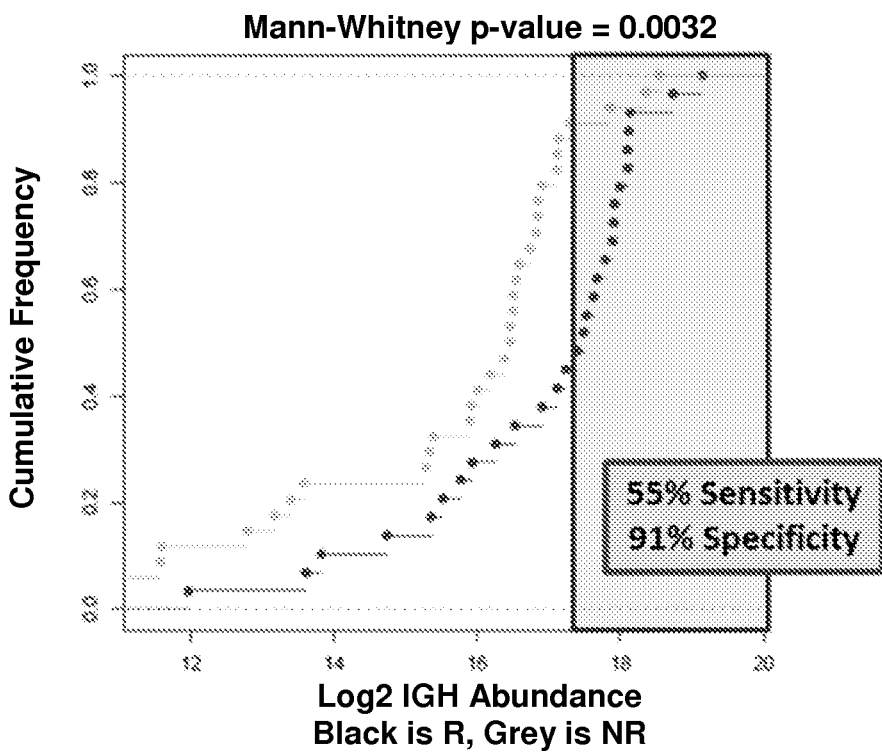
Figure 4:
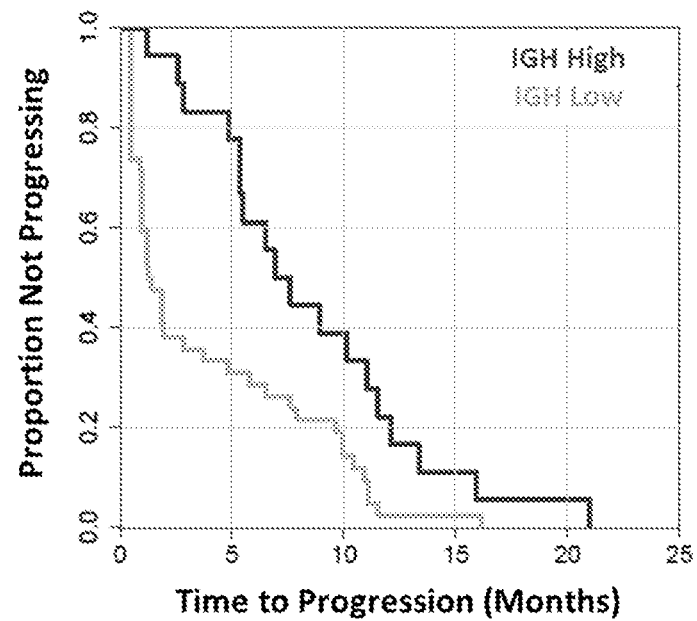
FIG. 4 is a graph demonstrating the time-to-progression (TTP) for IGH-High and IGH-Low patients treated with carfilzomib.

Due to the strength of the association, further analysis focused on IGH expression (FIGS. 3A and 3B). Various IGH locus expression cutoffs were considered and it was ultimately determined that an FPKQ cutoff of 160,000 (defining "IGH-High">=160,000 and "IGH-Low"<160,000) yielded the most clinically useful division the patients, predicting response in our training data with 55% sensitivity and 91% specificity. This same cutoff was then applied to time-to-progression (TTP) data for these patients, finding that IGH-High patients in this cohort have a 5.4-fold longer median TTP than IGH-Low patients (7.3 months vs. 1.3 months; log-rank P-value=0.003; FIG. 4).

To understand, how IG expression changes during treatment with proteasome inhibitors, the data was examined from one patient for which both a screening tumor sample and a sample collected on Cycle 1 Day 2 (C1D2) of treatment with single-agent carfilzomib were available. The results of this analysis are shown in Table 2.

TABLE 2

| | Expression | | |
| --- | --- | --- | --- |
| Gene | Screening | C1D2 | Fold-Change |
| IGHA1 | 4.2E+05 | 1.3E+05 | 3.37 |
| IGHV3-30 | 8.8E+04 | 2.4E+04 | 3.63 |
| IGHV3-33 | 7.7E+04 | 2.1E+04 | 3.77 |
| IGKC | 5.3E+05 | 1.4E+05 | 3.88 |
| ICKV3-20 | 3.9E+05 | 9.6E+04 | 4.11 |

Figure 5:
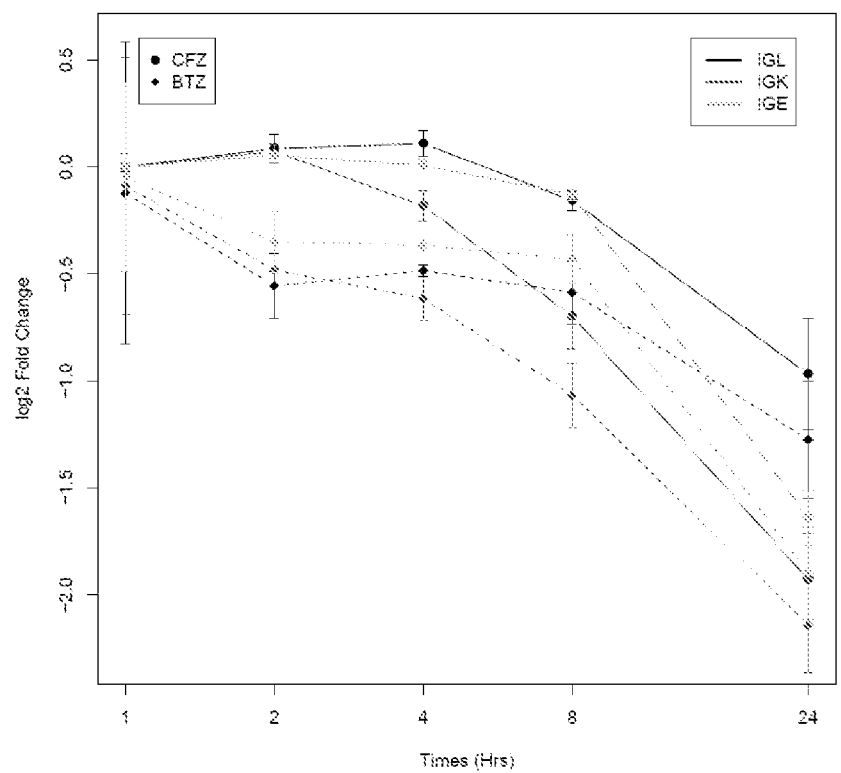
FIG. 5 is graph demonstrating the expression level of IG genes from multiple myeloma cell line (U266) continuously exposed to either bortezomib (BTZ) or carfilzomib (CFZ) for 24 hours.

As demonstrated in Table 2, IG expression is substantially (3- to 4-fold) lower in the sample collected one day after the first dose of carfilzomib. Similarly, RNA-Seq data from a multiple myeloma cell line (U266) continuously exposed to either bortezomib or carfilzomib for 24 hours was examined (FIG. 5). As in the patient samples above, expression of IG genes was substantially (3- to 4-fold) lower following exposure to either bortezomib or carfilzomib for 24 hours, which suggests that IG levels may be a proximal cause of death in cells exposed to proteasome inhibitors.

Figure 6:
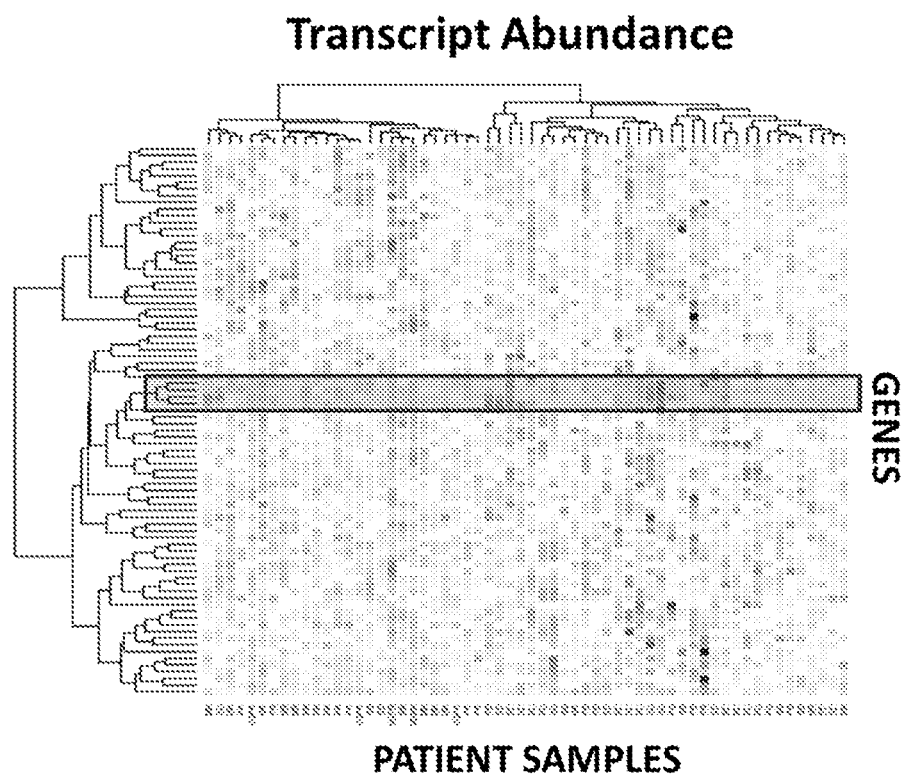
FIG. 6 is graphical representation of the transcriptional profiling data of tumors collected from patients subsequently treated with carfilzomib. Highlighted is a cluster of genes encoding proteins of the Ig structural superfamily, which includes FCGR2B
Figure 7A:
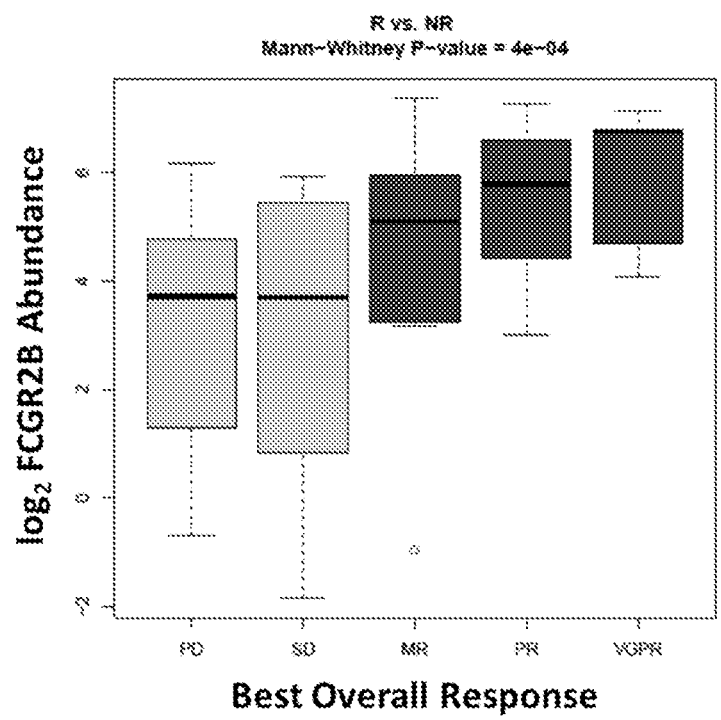
FIGS. 7A and 7B are graphs demonstrating the association between FCGR2b expression and carfilzomib response.
Figure 7B:
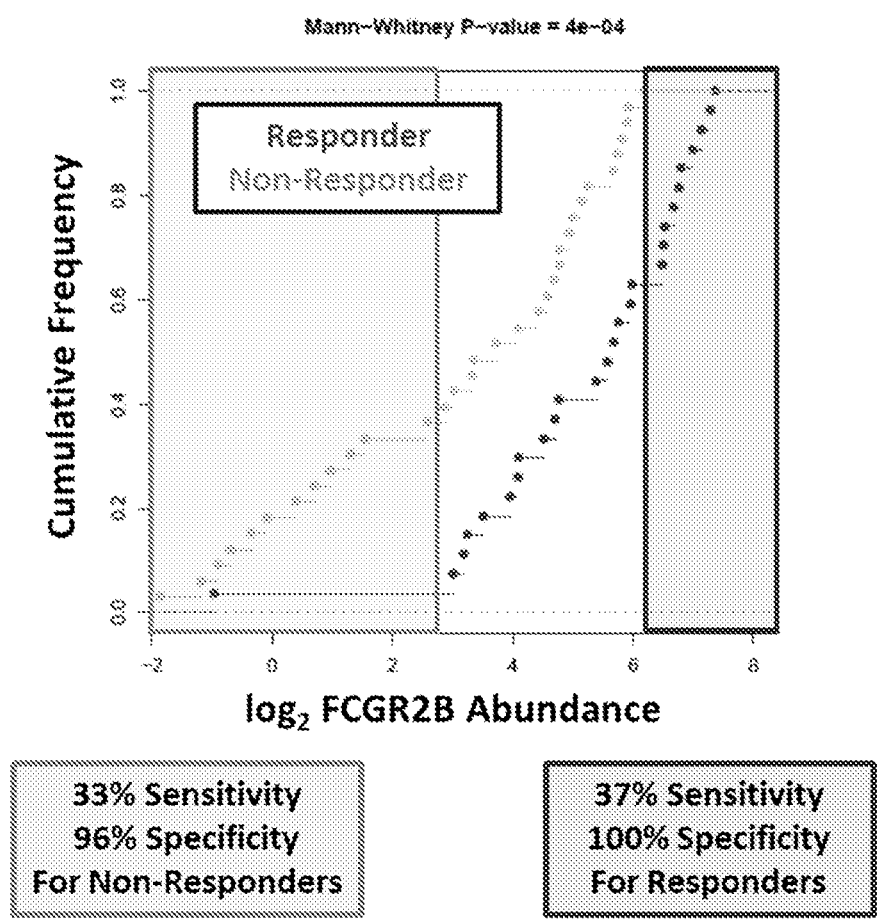

Looking more comprehensively, the inventors found a large set of genes (N=81) with expression that is significantly associated with response to carfilzomib (Wilcoxon P-value<10-3). The set includes an unexpectedly large number of genes encoding Ig folds that emerge as a small correlated cluster (FIG. 6), which implies that this class of proteins sensitizes cells to proteasome inhibition. This further suggests that high expression of immunoglobulin folds may be particularly proteotoxic to cells. A striking gene in this cluster is Fc gamma receptor 2B (FCGR2B), which is a receptor that normally binds Ig and down-modulates Ig production in B cells. Therefore, high FCGR2B expression may demarcate a tumor that is experiencing particularly high levels of proteotoxic stress from Ig production. Because of the close functional relationship between the IGH biomarker and FCGR2B, the inventors considered whether FCGR2B expression is an additional biomarker. The association between FCGR2B and response to carfilzomib (as defined above for IGH) is particularly strong (Wilcoxon P-value=4× 10–4; FIGS. 7A, 7B). Unlike for IGH, for FCGR2B it is apparent that both high and low FPKQ cutoffs are valuable for predicting responder and non-responder categories, respectively. In this case we determined that a high FPKQ cutoff of 75 (defining "FCGR2B-High">=75) and low FPKQ cutoff of 5 (defining "FCGR2B-Low"<5) yielded the most clinically useful division of our patients. The FCGR2B-High cutoff predicts responders in the training data with 37% sensitivity and 100% specificity, while the FCGR2B-Low cutoff predicts non-responders with 33% sensitivity and 96% specificity.

Figure 8:
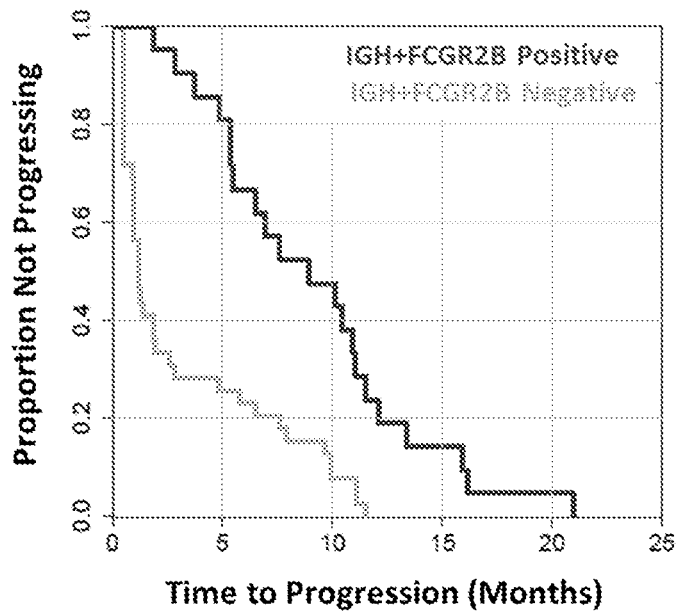
FIG. 8 is a is a graph demonstrating the time-to-progression (TTP) for IGH+FCGR2B positive an IGH+FCGR2G negative patients treated with carfilzomib.

Combining the two FCGR2B cutoffs with a slightly lowered IGH-High cutoff of 140,000, we are able to achieve sensitivity of 70% and specificity of 94% for predicting responders in the training data. Next, these same cutoffs were applied to time-to-progression (TTP) data for these patients, finding that IGH+FCGR2B-Positive patients in this cohort have a 7.3-fold longer median TTP than IGH+ FCGR2B-Negative patients (8.9 months vs. 1.2 months; log-rank P-value=3×10−5; FIG. 8).

Additional cutoffs for each individual biomarker (IGH and FCGR2B) and cutoffs for the combination of the two biomarkers were selected and the sensitivity and specificity for each of these additional cutoffs are listed in Tables 3A and 3B.

TABLE 3A

| Biomarker | Biomarker Cutoff | Sensitivity | Specificity |
|---|---|---|---|
| FCGR2B | 0 | 1 | 0 |
| FCGR2B | 1 | 0.962962963 | 0.151515152 |
| FCGR2B | 2 | 0.962962963 | 0.242424242 |
| FCGR2B | 3 | 0.962962963 | 0.272727273 |
| FCGR2B | 4 | 0.962962963 | 0.333333333 |
| FCGR2B | 7 | 0.962962963 | 0.363636364 |
| FCGR2B | 9 | 0.925925926 | 0.424242424 |
| FCGR2B | 10 | 0.851851852 | 0.424242424 |
| FCGR2B | 20 | 0.703703704 | 0.545454545 |
| FCGR2B | 30 | 0.592592593 | 0.666666667 |
| FCGR2B | 40 | 0.592592593 | 0.787878788 |
| FCGR2B | 50 | 0.481481481 | 0.818181818 |
| FCGR2B | 60 | 0.444444444 | 0.939393939 |
| FCGR2B | 70 | 0.37037037 | 0.96969697 |
| FCGR2B | 80 | 0.37037037 | 1 |
| FCGR2B | 100 | 0.259259259 | 1 |
| FCGR2B | 150 | 0.074074074 | 1 |
| FCGR2B | 170 | 0 | 1 |
| IGH | 0 | 1 | 0 |
| IGH | 10000 | 0.962962963 | 0.151515152 |
| IGH | 20000 | 0.925925926 | 0.212121212 |
| IGH | 30000 | 0.888888889 | 0.242424242 |
| IGH | 40000 | 0.888888889 | 0.242424242 |
| IGH | 50000 | 0.814814815 | 0.242424242 |
| IGH | 60000 | 0.814814815 | 0.272727273 |
| IGH | 70000 | 0.814814815 | 0.303030303 |
| IGH | 80000 | 0.814814815 | 0.363636364 |
| IGH | 90000 | 0.777777778 | 0.454545455 |
| IGH | 100000 | 0.777777778 | 0.484848485 |
| IGH | 110000 | 0.740740741 | 0.545454545 |
| IGH | 120000 | 0.703703704 | 0.606060606 |
| IGH | 130000 | 0.703703704 | 0.666666667 |
| IGH | 140000 | 0.703703704 | 0.696969697 |
| IGH | 150000 | 0.666666667 | 0.727272727 |
| IGH | 160000 | 0.666666667 | 0.727272727 |
| IGH | 200000 | 0.592592593 | 0.878787879 |
| IGH | 250000 | 0.333333333 | 0.909090909 |
| IGH | 300000 | 0.185185185 | 0.96969697 |
| IGH | 400000 | 0.074074074 | 0.96969697 |
| IGH | 450000 | 0.074074074 | 1 |
| IGH | 500000 | 0 | 1 |

TABLE 3B

| IGH_Cutoff | FCGR2B_low_Cutoff | FCGR2B_high_Cutofff | Sensitivity | Specificty |
|---|---|---|---|---|
| 100000 | 0 | 200 | 0 | 1 |
| 400000 | 100 | 200 | 0.074074074 | 1 |
| 1000000 | 0 | 110 | 0.148148148 | 1 |
| 200000 | 100 | 200 | 0.185185185 | 1 |
| 10000 | 100 | 200 | 0.222222222 | 1 |
| 1000000 | 3 | 110 | 0.259259259 | 1 |
| 150000 | 90 | 300 | 0.296296296 | 1 |
| 90000 | 90 | 500 | 0.333333333 | 1 |
| 1000000 | 2 | 90 | 0.37037037 | 1 |
| 90000 | 70 | 500 | 0.407407407 | 1 |
| 130000 | 50 | 110 | 0.444444444 | 0.96969697 |
| 200000 | 10 | 80 | 0.481481481 | 0.96969697 |
| 150000 | 40 | 90 | 0.518518519 | 0.96969697 |
| 110000 | 40 | 100 | 0.518518519 | 0.939393939 |
| 200000 | 10 | 200 | 0.518518519 | 0.909090909 |
| 200000 | 9 | 200 | 0.555555556 | 0.909090909 |
| 200000 | 8 | 500 | 0.592592593 | 0.909090909 |
| 200000 | 10 | 80 | 0.62962963 | 0.909090909 |
| 200000 | 9 | 90 | 0.666666667 | 0.909090909 |
| 200000 | 3 | 80 | 0.703703704 | 0.909090909 |
| 200000 | 2 | 80 | 0.703703704 | 0.878787879 |
| 200000 | 4 | 60 | 0.703703704 | 0.848484849 |
| 200000 | 0 | 60 | 0.703703704 | 0.818181818 |
| 140000 | 9 | 120 | 0.703703704 | 0.787878788 |
| 140000 | 5 | 80 | 0.777777778 | 0.787878788 |
| 130000 | 5 | 70 | 0.777777778 | 0.757575758 |
| 120000 | 2 | 80 | 0.777777778 | 0.727272727 |
| 200000 | 3 | 40 | 0.814814815 | 0.727272727 |
| 200000 | 0 | 40 | 0.814814815 | 0.696969697 |
| 200000 | 2 | 30 | 0.814814815 | 0.666666667 |
| 80000 | 5 | 70 | 0.814814815 | 0.636363636 |
| 80000 | 8 | 60 | 0.814814815 | 0.606060606 |
| 120000 | 5 | 40 | 0.851851852 | 0.606060606 |
| 100000 | 5 | 40 | 0.851851852 | 0.575757576 |
| 80000 | 4 | 40 | 0.888888889 | 0.575757576 |
| 80000 | 6 | 30 | 0.888888889 | 0.545454546 |
| 30000 | 6 | 110 | 0.888888889 | 0.515151515 |
| 10000 | 9 | 200 | 0.888888889 | 0.484848485 |
| 20000 | 5 | 100 | 0.925925926 | 0.484848485 |
| 40000 | 7 | 30 | 0.925925926 | 0.454545455 |
| 30000 | 3 | 40 | 0.925925926 | 0.424242424 |
| 10000 | 5 | 120 | 0.962962963 | 0.424242424 |
| 60000 | 5 | 10 | 0.962962963 | 0.393939394 |

TABLE 3B-continued

| IGH_Cutoff | FCGR2B_low_Cutoff | FCGR2B_high_Cutoff | Sensitivity | Specificty |
|---|---|---|---|---|
| 140000 | 1 | 10 | 0.962962963 | 0.363636364 |
| 10000 | 2 | 60 | 0.962962963 | 0.333333333 |
| 100000 | 1 | 10 | 0.962962963 | 0.303030303 |
| 10000 | 1 | 100 | 0.962962963 | 0.272727273 |
| 70000 | 1 | 10 | 0.962962963 | 0.242424242 |
| 20000 | 0 | 100 | 0.962962963 | 0.212121212 |
| 20000 | 0 | 50 | 0.962962963 | 0.181818182 |
| 10000 | 0 | 200 | 0.962962963 | 0.151515152 |
| 40000 | 0 | 20 | 0.962962963 | 0.121212121 |
| 60000 | 0 | 10 | 1 | 0.090909091 |
| 90000 | 70 | 0 | 1 | 0 |

Figure 9:
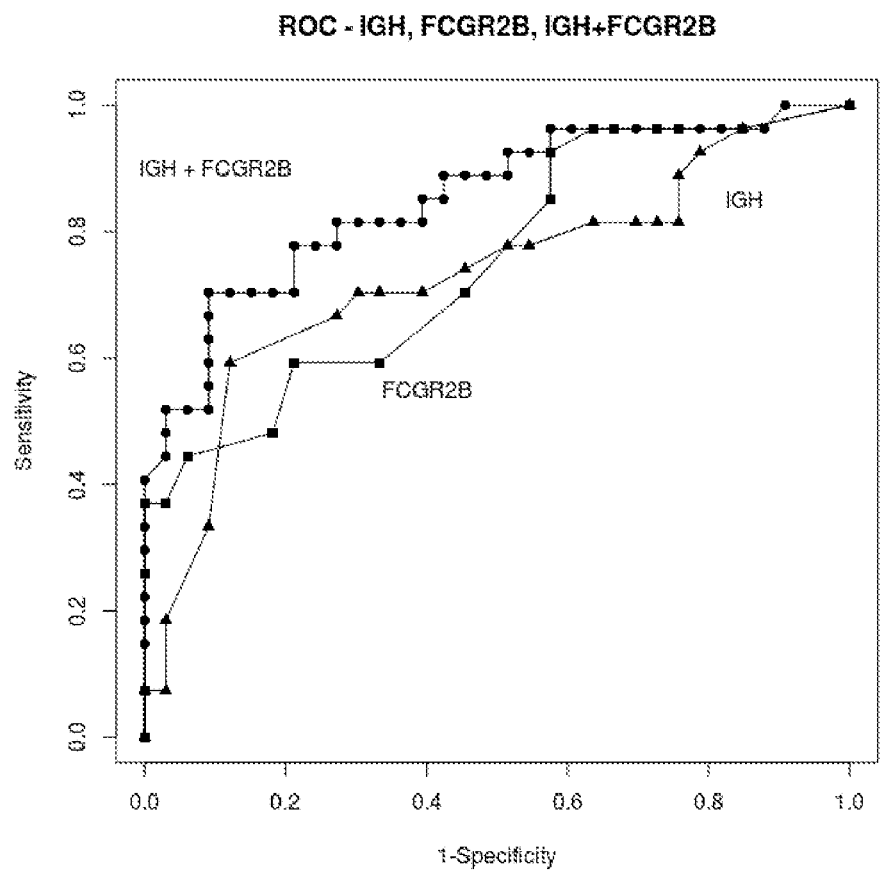
FIG. 9 is a graph containing three receiver operating characteristic (ROC) curves, each curve plotting cutoff values corresponding to a % specificity and % sensitivity: IGH, FCGR2B, and the combination of IGH and FCGR2B.

The % sensitivity and % specificity values shown in Tables 3A and 3B are datapoints of the response operating characteristic (ROC) curves shown in FIG. 9. FIG. 9 contains additional cutoffs (other than those in Tables 3A and 3B) as well as the corresponding % sensitivity and % specificity for each additional cutoff. The curve in FIG. 9 for IGH and FCGR2B (labeled as "IGH+FCGR2B") allows for one to evaluate different combined cutoffs in terms of % sensitivity and % specificity. The different cutoffs thus provide for a multitude of diagnostic thresholds above which are determinative of a patient's treatment regimen. Cutoffs having the desired % sensitivity/% specificity values are then applied to TTP data.

Example 3: Additional Biomarkers

As discussed in Example 2, a large set of genes demonstrated expression that is significantly associated with patient response to carfilzomib. A table listing this set of genes is set forth herein as Table 4. Table 4 includes, for each gene: (i) the HUGO gene symbol, if available, (ii) the Ensembl Gene Name, (iii) gene expression level data, and (iv) statistical data: the P-value and Q-value.

TABLE 4

| HUGO Gene Symbol | Ensembl Gene Name | log2 (R/NR) | Δ gene expression level | P-value | Q-value |
|---|---|---|---|---|---|
| ABI2 | ENSG00000138443 | 0.58949304 | up | 0.001738 | 0.1271 |
| AC004381.6 | ENSG00000005189 | -1.204670581 | down | 0.000103 | 0.090927 |
| AC005076.5 | ENSG00000224046 | -0.653150315 | down | 0.002953 | 0.154081 |
| AC005104.3 | ENSG00000223374 | 0.765035153 | up | 0.006398 | 0.199433 |
| AC005943.5 | ENSG00000267161 | -1.004306556 | down | 0.003757 | 0.167074 |
| AC006378.2 | ENSG00000236861 | 0.923095301 | up | 0.00163 | 0.125963 |
| AC007246.3 | ENSG00000231312 | 0.507143559 | up | 0.001835 | 0.1271 |
| AC007381.3 | ENSG00000228590 | 1.794650455 | up | 0.001471 | 0.125963 |
| AC007386.2 | ENSG00000237638 | 1.314108591 | up | 0.001551 | 0.125963 |
| AC009005.2 | ENSG00000267751 | -1.012595637 | down | 0.003809 | 0.167074 |
| AC108488.3 | ENSG00000234171 | -0.530514717 | down | 0.005379 | 0.185044 |
| ACAT2 | ENSG00000120437 | -0.691367312 | down | 0.001474 | 0.125963 |
| ACOT7 | ENSG00000097021 | -1.127585567 | down | 0.006514 | 0.199433 |
| ACYP1 | ENSG00000119640 | -0.679663744 | down | 0.001835 | 0.1271 |
| ADCK1 | ENSG00000063761 | -0.429549728 | down | 0.004209 | 0.174124 |
| ADIRF | ENSG00000148671 | 1.068032417 | up | 0.005074 | 0.182007 |
| AGMAT | ENSG00000116771 | -1.902702799 | down | 0.004209 | 0.174124 |
| AKAP9 | ENSG00000127914 | 0.578033255 | up | 0.005379 | 0.185044 |
| ALCAM | ENSG00000170017 | 1.998126961 | up | 1.29E-05 | 0.067115 |
| ALDH4A1 | ENSG00000159423 | -0.887790496 | down | 0.00488 | 0.180898 |
| AMDHD2 | ENSG00000162066 | -0.533471154 | down | 0.001937 | 0.129464 |
| AMH | ENSG00000104899 | -1.185346863 | down | 0.005212 | 0.184691 |
| ANKRD20A3 | ENSG00000132498 | 2.350221687 | up | 0.000209 | 0.090927 |
| ANKRD20A4 | ENSG00000172014 | 2.863800069 | up | 0.004287 | 0.175935 |
| ANKRD20A5P | ENSG00000186481 | 1.556593095 | up | 0.000788 | 0.112803 |
| ANLN | ENSG00000011426 | -1.397930353 | down | 0.000939 | 0.11973 |
| ANTXR1 | ENSG00000169604 | 2.166414183 | up | 0.004533 | 0.179635 |
| APH1B | ENSG00000138613 | 0.516819563 | up | 0.006212 | 0.196883 |
| APOBEC3H | ENSG00000100298 | -1.351138348 | down | 0.000744 | 0.112803 |
| ARHGAP11A | ENSG00000198826 | -0.655219921 | down | 0.006212 | 0.196883 |
| ARHGAP23 | ENSG00000225485 | 0.522801324 | up | 0.004647 | 0.179635 |
| ARHGAP31-AS1 | ENSG00000241155 | 0.652112201 | up | 0.000254 | 0.090927 |
| ARL8B | ENSG00000134108 | 0.292126417 | up | 0.003809 | 0.167074 |
| ARMC5 | ENSG00000140691 | -0.323867652 | down | 0.001474 | 0.125963 |
| ASB1 | ENSG00000065802 | -0.417067595 | down | 9.32E-06 | 0.067115 |
| ASF1B | ENSG00000105011 | -0.792494369 | down | 0.003622 | 0.165504 |
| ASPDH | ENSG00000204653 | 1.13291303 | up | 0.002752 | 0.149035 |
| ASPH | ENSG00000198363 | 0.552936064 | up | 0.006514 | 0.199433 |
| ATAD5 | ENSG00000176208 | -0.926161416 | down | 0.002804 | 0.149035 |
| ATG4A | ENSG00000101844 | 0.454441032 | up | 0.001474 | 0.125963 |
| ATP2C1 | ENSG00000017260 | 0.414259932 | up | 0.002044 | 0.13169 |

TABLE 4-continued

| HUGO Gene Symbol | Ensembl Gene Name | log2 (R/NR) | Δ gene expression level | P-value | Q-value |
|---|---|---|---|---|---|
| ATXN7L2 | ENSG00000162650 | −0.602432936 | down | 0.001947 | 0.12962 |
| AUNIP | ENSG00000127423 | −1.420068922 | down | 0.002804 | 0.149035 |
| B2M | ENSG00000166710 | 0.438515982 | up | 0.003272 | 0.160028 |
| B4GALT4 | ENSG00000121578 | 0.499817339 | up | 0.005922 | 0.194138 |
| BAHD1 | ENSG00000140320 | 0.521294292 | up | 0.001319 | 0.125963 |
| BBX | ENSG00000114439 | 0.442989973 | up | 0.001835 | 0.1271 |
| BCAR3 | ENSG00000137936 | 1.528931715 | up | 0.001937 | 0.129464 |
| BET1L | ENSG00000177951 | 0.544159583 | up | 0.004423 | 0.177259 |
| BEX2 | ENSG00000133134 | 1.389224675 | up | 0.001053 | 0.125345 |
| BIK | ENSG00000100290 | 0.790115837 | up | 0.002156 | 0.135243 |
| BIRC5 | ENSG00000089685 | −1.476698726 | down | 0.002526 | 0.144291 |
| BMPR1A | ENSG00000107779 | 1.417631639 | up | 0.002526 | 0.144291 |
| BRCA1 | ENSG00000012048 | −1.220603695 | down | 0.001179 | 0.125345 |
| BTD | ENSG00000169814 | 0.7332119 | up | 0.001474 | 0.125963 |
| BTLA | ENSG00000186265 | 1.270519458 | up | 0.002526 | 0.144291 |
| C12orf23 | ENSG00000151135 | 0.47094641 | up | 0.003809 | 0.167074 |
| C14orf80 | ENSG00000185347 | −0.701479303 | down | 0.000552 | 0.1043 |
| C16orf59 | ENSG00000162062 | −1.158684113 | down | 0.000622 | 0.106442 |
| C17orf53 | ENSG00000125319 | −0.565512324 | down | 0.006514 | 0.199433 |
| C19orf12 | ENSG00000131943 | 0.739111952 | up | 0.000135 | 0.090927 |
| C19orf40 | ENSG00000131944 | −0.636229388 | down | 0.002397 | 0.140035 |
| C1orf112 | ENSG00000000460 | −0.903350952 | down | 0.001835 | 0.1271 |
| C1orf132 | ENSG00000203709 | 0.77824824 | up | 0.005124 | 0.182007 |
| C22orf26 | ENSG00000182257 | −1.201787593 | down | 0.001295 | 0.125963 |
| C3orf17 | ENSG00000163608 | 0.355702903 | up | 0.001937 | 0.129464 |
| C3orf37 | ENSG00000183624 | 0.568954382 | up | 0.001319 | 0.125963 |
| CACNB1 | ENSG00000067191 | −1.119138756 | down | 0.004647 | 0.179635 |
| CAMK2B | ENSG00000058404 | 1.080919995 | up | 0.001079 | 0.125345 |
| CAPN15 | ENSG00000103326 | −0.314834712 | down | 0.003272 | 0.160028 |
| CAPN7 | ENSG00000131375 | 0.429443198 | up | 0.000661 | 0.106442 |
| CARHSP1 | ENSG00000153048 | −0.497561027 | down | 0.000661 | 0.106442 |
| CASC4 | ENSG00000166734 | 0.636516042 | up | 0.002044 | 0.13169 |
| CBX7 | ENSG00000100307 | 0.589142024 | up | 0.002804 | 0.149035 |
| CCDC101 | ENSG00000176476 | −0.295016908 | down | 0.004005 | 0.170766 |
| CCDC103 | ENSG00000167131 | −1.302299288 | down | 0.001137 | 0.125345 |
| CCDC137 | ENSG00000185298 | −0.344295242 | down | 0.001646 | 0.125963 |
| CCDC144CP | ENSG00000154898 | 1.94825361 | up | 0.001319 | 0.125963 |
| CCDC18 | ENSG00000122483 | −0.661657101 | down | 0.001835 | 0.1271 |
| CCDC34 | ENSG00000109881 | −1.207485494 | down | 0.001395 | 0.125963 |
| CCHCR1 | ENSG00000204536 | −0.487115512 | down | 0.005713 | 0.1918 |
| CCNA2 | ENSG00000145386 | −1.518792258 | down | 0.001937 | 0.129464 |
| CCNF | ENSG00000162063 | −0.797996486 | down | 0.000245 | 0.090927 |
| CCPG1 | ENSG00000260916 | 0.805364603 | up | 0.002044 | 0.13169 |
| CD200 | ENSG00000091972 | 2.296546672 | up | 0.000382 | 0.097757 |
| CD276 | ENSG00000103855 | 2.23215983 | up | 0.000202 | 0.090927 |
| CD46 | ENSG00000117335 | 0.535055566 | up | 0.005124 | 0.182007 |
| CD47 | ENSG00000196776 | 0.418206401 | up | 0.002397 | 0.140035 |
| CDC25B | ENSG00000101224 | −0.626962109 | down | 0.002397 | 0.140035 |
| CDC45 | ENSG00000093009 | −1.488486593 | down | 0.00488 | 0.180898 |
| CDC7 | ENSG00000097046 | −0.703380887 | down | 0.00488 | 0.180898 |
| CDCA2 | ENSG00000184661 | −1.693705194 | down | 0.005124 | 0.182007 |
| CDCA4 | ENSG00000170779 | −0.934167192 | down | 0.000279 | 0.092728 |
| CDCA7L | ENSG00000164649 | −0.90401625 | down | 0.003109 | 0.157059 |
| CDCA8 | ENSG00000134690 | −1.131192478 | down | 0.001474 | 0.125963 |
| CDKN3 | ENSG00000100526 | −0.866129394 | down | 0.003109 | 0.157059 |
| CDT1 | ENSG00000167513 | −1.509518103 | down | 0.000788 | 0.112803 |
| CENPC | ENSG00000145241 | 0.477584435 | up | 0.005379 | 0.185044 |
| CENPH | ENSG00000153044 | −1.059152551 | down | 0.006212 | 0.196883 |
| CENPL | ENSG00000120334 | −0.689597294 | down | 0.003622 | 0.165504 |
| CENPW | ENSG00000203760 | −1.336241011 | down | 8.35E−05 | 0.090927 |
| CEP250 | ENSG00000126001 | −0.533656922 | down | 0.001646 | 0.125963 |
| CEP55 | ENSG00000138180 | −1.336985816 | down | 0.004423 | 0.177259 |
| CEP78 | ENSG00000148019 | −0.713457762 | down | 6.76E−05 | 0.086188 |
| CFLAR-AS1 | ENSG00000226312 | 0.787576615 | up | 0.001474 | 0.125963 |
| CHAF1A | ENSG00000167670 | −0.516246117 | down | 0.001646 | 0.125963 |
| CHAF1B | ENSG00000159259 | −1.117439741 | down | 0.000155 | 0.090927 |
| CHTF18 | ENSG00000127586 | −0.923356052 | down | 6.21E−05 | 0.086188 |
| CIT | ENSG00000122966 | −1.008818794 | down | 0.001179 | 0.125345 |
| CLIC2 | ENSG00000155962 | 2.236011571 | up | 0.000245 | 0.090927 |
| CLIC5 | ENSG00000112782 | 1.869491174 | up | 0.001806 | 0.1271 |
| CLPTM1 | ENSG00000104853 | 0.466267313 | up | 0.000788 | 0.112803 |
| CLSPN | ENSG00000092853 | −1.383198126 | down | 0.000788 | 0.112803 |
| CNTN1 | ENSG00000018236 | 2.897399147 | up | 0.002156 | 0.135243 |
| COPZ2 | ENSG00000005243 | 2.563354592 | up | 0.000135 | 0.090927 |
| CRBN | ENSG00000113851 | 0.479237667 | up | 0.003809 | 0.167074 |
| CREB3L2 | ENSG00000182158 | 1.297905196 | up | 9.60E−05 | 0.090927 |

TABLE 4-continued

| HUGO Gene Symbol | Ensembl Gene Name | log2 (R/NR) | Δ gene expression level | P-value | Q-value |
|---|---|---|---|---|---|
| CRELD2 | ENSG00000184164 | 0.431307815 | up | 0.004209 | 0.174124 |
| CRYBG3 | ENSG00000080200 | 0.744498557 | up | 0.001319 | 0.125963 |
| CRYBG3 | ENSG00000233280 | 1.330532021 | up | 0.000519 | 0.103273 |
| CSPG4P11 | ENSG00000259622 | 1.650979674 | up | 0.000849 | 0.118158 |
| CSPG4P12 | ENSG00000259295 | 1.31746016 | up | 0.000744 | 0.112803 |
| CTD-2013N24.2 | ENSG00000244513 | 0.416073076 | up | 0.004647 | 0.179635 |
| CTD-2545G14.7 | ENSG00000262526 | 1.864150843 | up | 0.001937 | 0.129464 |
| CTD-2574D22.2 | ENSG00000247735 | −1.395823366 | down | 0.003752 | 0.167074 |
| CTIF | ENSG00000134030 | 0.507094853 | up | 0.006212 | 0.196883 |
| CTNNA1 | ENSG00000044115 | 0.445702107 | up | 0.000177 | 0.090927 |
| CXorf40B | ENSG00000197021 | 0.343593674 | up | 0.001558 | 0.125963 |
| CXXC5 | ENSG00000171604 | 0.520417324 | up | 0.005379 | 0.185044 |
| CYFIP1 | ENSG00000068793 | 0.603707882 | up | 0.001179 | 0.125345 |
| CYP4F35P | ENSG00000265787 | 2.131597155 | up | 0.001551 | 0.125963 |
| DAGLB | ENSG00000164535 | −0.338981228 | down | 0.003443 | 0.164705 |
| DBF4B | ENSG00000161692 | −0.536907475 | down | 0.00488 | 0.180898 |
| DBI | ENSG00000155368 | 0.437631696 | up | 0.003272 | 0.160028 |
| DCK | ENSG00000156431 | −0.710740223 | down | 0.002397 | 0.140035 |
| DDX42 | ENSG00000198231 | 0.208628409 | up | 0.002044 | 0.13169 |
| DEPDC1 | ENSG00000024526 | −1.138548661 | down | 0.002953 | 0.154081 |
| DERL1 | ENSG00000136986 | 0.629070039 | up | 0.000622 | 0.106442 |
| DERL3 | ENSG00000099958 | 0.87425742 | up | 0.000552 | 0.1043 |
| DGKI | ENSG00000157680 | 1.522742848 | up | 0.004528 | 0.179635 |
| DHFR | ENSG00000228716 | −0.596887056 | down | 0.001474 | 0.125963 |
| DLG1 | ENSG00000075711 | 0.720945313 | up | 0.003272 | 0.160028 |
| DLGAP5 | ENSG00000126787 | −1.781943562 | down | 0.002526 | 0.144291 |
| DNAJB9 | ENSG00000128590 | 0.762742522 | up | 0.000215 | 0.090927 |
| DNAJC1 | ENSG00000136770 | 0.851198135 | up | 0.003622 | 0.165504 |
| DNASE1L3 | ENSG00000163687 | 1.150573975 | up | 0.003411 | 0.164705 |
| DNMT1 | ENSG00000130816 | −0.401905618 | down | 0.001474 | 0.125963 |
| DOT1L | ENSG00000104885 | −0.440849834 | down | 0.001474 | 0.125963 |
| DQX1 | ENSG00000144045 | −1.58805775 | down | 0.005822 | 0.194138 |
| DST | ENSG00000151914 | 1.119680181 | up | 0.00488 | 0.180898 |
| DTL | ENSG00000143476 | −0.571087426 | down | 0.005458 | 0.187352 |
| DTYMK | ENSG00000168393 | −0.672857439 | down | 0.001835 | 0.1271 |
| DVL3 | ENSG00000161202 | 0.480840184 | up | 0.000622 | 0.106442 |
| E2F1 | ENSG00000101412 | −0.713005902 | down | 0.003809 | 0.167074 |
| E2F8 | ENSG00000129173 | −1.822880964 | down | 0.004647 | 0.179635 |
| ECHDC2 | ENSG00000121310 | 0.80675917 | up | 0.001319 | 0.125963 |
| EFCAB11 | ENSG00000140025 | −0.83951759 | down | 0.000316 | 0.09315 |
| EIF2AK4 | ENSG00000128829 | 0.889621607 | up | 0.004005 | 0.170766 |
| EIF2B5 | ENSG00000145191 | 0.52014902 | up | 0.001179 | 0.125345 |
| EMC7 | ENSG00000134153 | 0.527652572 | up | 0.002156 | 0.135243 |
| ENDOU | ENSG00000111405 | 0.996677877 | up | 0.000764 | 0.112803 |
| EPDR1 | ENSG00000086289 | 1.355276772 | up | 0.003109 | 0.157059 |
| EPM2AIP1 | ENSG00000178567 | 0.832768018 | up | 0.000622 | 0.106442 |
| ERBB2 | ENSG00000141736 | −0.520928902 | down | 0.000939 | 0.11973 |
| ERI1 | ENSG00000104626 | −0.601791404 | down | 0.000245 | 0.090927 |
| ESCO2 | ENSG00000171320 | −1.5468643 | down | 0.006514 | 0.199433 |
| ESPL1 | ENSG00000135476 | −0.932485167 | down | 0.003622 | 0.165504 |
| ETV5 | ENSG00000244405 | 0.880406053 | up | 0.001738 | 0.1271 |
| FAM114A1 | ENSG00000197712 | 0.986415082 | up | 0.00046 | 0.097757 |
| FAM174A | ENSG00000174132 | 0.851426172 | up | 0.005124 | 0.182007 |
| FAM219A | ENSG00000164970 | 0.431957782 | up | 0.001474 | 0.125963 |
| FAM64A | ENSG00000129195 | −1.675400995 | down | 0.000432 | 0.097757 |
| FAM72B | ENSG00000188610 | −0.874624959 | down | 0.000261 | 0.090927 |
| FAM83D | ENSG00000101447 | −0.996366514 | down | 0.000203 | 0.090927 |
| FAM95B1 | ENSG00000223839 | 1.618293895 | up | 0.004209 | 0.174124 |
| FANCA | ENSG00000187741 | −0.802052008 | down | 0.000406 | 0.097757 |
| FANCB | ENSG00000181544 | −0.733853593 | down | 0.001137 | 0.125345 |
| FBLN2 | ENSG00000163520 | 4.055675182 | up | 0.002318 | 0.139712 |
| FBXL15 | ENSG00000107872 | 0.347540494 | up | 0.00488 | 0.180898 |
| FCF1 | ENSG00000119616 | −0.367208753 | down | 0.000432 | 0.097757 |
| FCGR2B | ENSG00000072694 | 1.7069366 | up | 0.000552 | 0.1043 |
| FCGR2C | ENSG00000244682 | 1.833667492 | up | 0.001937 | 0.129464 |
| FCRL5 | ENSG00000143297 | 1.284877883 | up | 0.001179 | 0.125345 |
| FCRLA | ENSG00000132185 | 3.193292318 | up | 8.96E−05 | 0.090927 |
| FGFR1OP | ENSG00000213066 | −0.491542609 | down | 0.003272 | 0.160028 |
| FOXM1 | ENSG00000111206 | −1.131740677 | down | 0.004332 | 0.176822 |
| FUS | ENSG00000089280 | −0.352688172 | down | 0.000261 | 0.090927 |
| FXYD5 | ENSG00000089327 | 0.875760601 | up | 0.001646 | 0.125963 |
| FXYD7 | ENSG00000221946 | 1.006169767 | up | 0.003585 | 0.165504 |
| GALE | ENSG00000117308 | −0.542602271 | down | 0.002953 | 0.154081 |

TABLE 4-continued

| HUGO Gene Symbol | Ensembl Gene Name | log2 (R/NR) | Δ gene expression level | P-value | Q-value |
|---|---|---|---|---|---|
| GBF1 | ENSG00000107862 | 0.476441929 | up | 0.000279 | 0.092728 |
| GINS2 | ENSG00000131153 | −0.805724953 | down | 0.003809 | 0.167074 |
| GINS4 | ENSG00000147536 | −0.996858828 | down | 0.000661 | 0.106442 |
| GLMN | ENSG00000174842 | −0.690322855 | down | 0.001247 | 0.125963 |
| GMEB1 | ENSG00000162419 | −0.25590121 | down | 0.004423 | 0.177259 |
| GNG7 | ENSG00000176533 | 0.927431553 | up | 0.004209 | 0.174124 |
| GOLGA4 | ENSG00000144674 | 0.386722654 | up | 0.004005 | 0.170766 |
| GOLGA6L4 | ENSG00000184206 | 0.812716533 | up | 0.000189 | 0.090927 |
| GPBP1 | ENSG00000062194 | 0.242730418 | up | 0.006514 | 0.199433 |
| GPR176 | ENSG00000166073 | 2.035062721 | up | 0.001114 | 0.125345 |
| GPRASP1 | ENSG00000198932 | 1.071771461 | up | 0.003443 | 0.164705 |
| GPSM2 | ENSG00000121957 | −0.885489534 | down | 6.29E−05 | 0.086188 |
| GRIP1 | ENSG00000155974 | 1.231430795 | up | 0.004231 | 0.174124 |
| GSG2 | ENSG00000177602 | −1.394544327 | down | 0.000406 | 0.097757 |
| GTF2I | ENSG00000077809 | 0.40001011 | up | 0.000886 | 0.118955 |
| HAUS4 | ENSG00000092036 | −0.602117697 | down | 0.002397 | 0.140035 |
| HDAC9 | ENSG00000048052 | 0.684068321 | up | 0.001646 | 0.125963 |
| HELLS | ENSG00000119969 | −0.623431519 | down | 0.001558 | 0.125963 |
| HENMT1 | ENSG00000162639 | −0.624504013 | down | 0.001474 | 0.125963 |
| HERPUD1 | ENSG00000051108 | 0.778585363 | up | 0.001646 | 0.125963 |
| HLA-DOB | ENSG00000241106 | 1.443362687 | up | 3.51E−05 | 0.067115 |
| HMGB1P5 | ENSG00000132967 | −0.489741805 | down | 0.005645 | 0.190341 |
| HMGN2 | ENSG00000198830 | −0.343343082 | down | 0.004647 | 0.179635 |
| HNRNPCP1 | ENSG00000258900 | −0.953716452 | down | 0.004743 | 0.180898 |
| HSDL2 | ENSG00000119471 | −0.610519971 | down | 0.006212 | 0.196883 |
| ICAM5 | ENSG00000105376 | −1.044794924 | down | 0.004209 | 0.174124 |
| IDUA | ENSG00000127415 | 0.955710969 | up | 0.001646 | 0.125963 |
| IFT20 | ENSG00000109083 | 0.302770683 | up | 0.003109 | 0.157059 |
| ITPRIPL1 | ENSG00000198885 | −2.2280116 | down | 0.000586 | 0.106442 |
| ITSN1 | ENSG00000205726 | 0.905232008 | up | 0.002804 | 0.149035 |
| KATNA1 | ENSG00000186625 | −0.391521115 | down | 0.001179 | 0.125345 |
| KCNAB1 | ENSG00000169282 | 1.001128869 | up | 0.000359 | 0.097757 |
| KCNAB3 | ENSG00000170049 | −1.056336096 | down | 0.002273 | 0.138647 |
| KIAA0226 | ENSG00000145016 | 0.617682853 | up | 0.002953 | 0.154081 |
| KIAA0586 | ENSG00000100578 | −0.431753645 | down | 0.006212 | 0.196883 |
| KIAA1147 | ENSG00000257093 | 0.482751184 | up | 0.006514 | 0.199433 |
| KIAA1522 | ENSG00000162522 | 1.035387539 | up | 0.005124 | 0.182007 |
| KIAA1731 | ENSG00000166004 | −0.469427264 | down | 0.000788 | 0.112803 |
| KIF14 | ENSG00000118193 | −1.705333985 | down | 0.001474 | 0.125963 |
| KIF18A | ENSG00000121621 | −0.692732773 | down | 0.001179 | 0.125345 |
| KIF20B | ENSG00000138182 | −0.628519438 | down | 0.001053 | 0.125345 |
| KIF2C | ENSG00000142945 | −1.365646338 | down | 0.000432 | 0.097757 |
| KIF4A | ENSG00000090889 | −1.904610649 | down | 0.003622 | 0.165504 |
| KMT2C | ENSG00000055609 | 0.228004365 | up | 0.005645 | 0.190341 |
| KPNB1 | ENSG00000108424 | −0.394700087 | down | 0.001835 | 0.1271 |
| L2HGDH | ENSG00000087299 | −0.921327169 | down | 0.000836 | 0.117391 |
| LAMTOR5-AS1 | ENSG00000224699 | −0.981944468 | down | 0.002047 | 0.13169 |
| LINC00337 | ENSG00000225077 | −1.120082576 | down | 0.005676 | 0.19098 |
| LINC00662 | ENSG00000261824 | 0.773101729 | up | 0.005922 | 0.194138 |
| LINC00883 | ENSG00000243701 | 0.810773121 | up | 0.004005 | 0.170766 |
| LMF1 | ENSG00000103227 | 0.814937221 | up | 0.000622 | 0.106442 |
| LPCAT3 | ENSG00000111684 | −0.559209562 | down | 0.004005 | 0.170766 |
| LRRC4B | ENSG00000131409 | 0.793959329 | up | 0.004213 | 0.174124 |
| LRRN2 | ENSG00000170382 | 1.865843931 | up | 0.005922 | 0.194138 |
| MAGED2 | ENSG00000102316 | 0.720903224 | up | 0.001179 | 0.125345 |
| MAP4 | ENSG00000047849 | 0.724838313 | up | 0.002662 | 0.147631 |
| MAP4K3 | ENSG00000011566 | 0.589878912 | up | 0.004209 | 0.174124 |
| MAPRE3 | ENSG00000084764 | 0.784298761 | up | 0.000261 | 0.090927 |
| MBD4 | ENSG00000129071 | 0.276423792 | up | 0.000788 | 0.112803 |
| MCM10 | ENSG00000065328 | −1.334114767 | down | 0.001674 | 0.1271 |
| MCM2 | ENSG00000073111 | −1.247745579 | down | 0.001474 | 0.125963 |
| MCM4 | ENSG00000104738 | −0.927747184 | down | 0.001646 | 0.125963 |
| MEF2A | ENSG00000068305 | 0.506720645 | up | 0.000744 | 0.112803 |
| MEI1 | ENSG00000167077 | 1.179961962 | up | 0.000118 | 0.090927 |
| MEMO1 | ENSG00000162959 | −0.281226311 | down | 0.004209 | 0.174124 |
| MFN1 | ENSG00000171109 | 0.332545316 | up | 0.006212 | 0.196883 |
| MGAT1 | ENSG00000131446 | 0.290644604 | up | 0.006514 | 0.199433 |
| MGME1 | ENSG00000125871 | −0.433132545 | down | 0.003809 | 0.167074 |
| MGST3 | ENSG00000143198 | 0.659094058 | up | 0.005124 | 0.182007 |
| MICA | ENSG00000204520 | 0.620119411 | up | 0.000939 | 0.11973 |
| MID2 | ENSG00000080561 | 0.756163973 | up | 0.005645 | 0.190341 |
| MIR4435-1HG | ENSG00000172965 | −1.062297175 | down | 0.00488 | 0.180898 |
| MKX | ENSG00000150051 | 2.704795186 | up | 0.000382 | 0.097757 |
| MLF1IP | ENSG00000151725 | −0.868339353 | down | 0.005645 | 0.190341 |
| MMRN2 | ENSG00000173269 | 1.180392072 | up | 0.002662 | 0.147631 |

TABLE 4-continued

| HUGO Gene Symbol | Ensembl Gene Name | log2 (R/NR) | Δ gene expression level | P-value | Q-value |
|---|---|---|---|---|---|
| MOXD1 | ENSG00000079931 | 1.559687372 | up | 0.004647 | 0.179635 |
| MRAS | ENSG00000158186 | 1.52251306 | up | 0.00488 | 0.180898 |
| MSH2 | ENSG00000095002 | −1.009515534 | down | 0.006514 | 0.199433 |
| MTFR2 | ENSG00000146410 | −0.846036223 | down | 0.000489 | 0.099767 |
| MXD4 | ENSG00000123933 | 0.515542459 | up | 0.004423 | 0.177259 |
| MYBL2 | ENSG00000101057 | −1.035211825 | down | 0.001247 | 0.125963 |
| MYEF2 | ENSG00000104177 | 1.112353906 | up | 0.005124 | 0.182007 |
| MZB1 | ENSG00000170476 | 0.965983178 | up | 0.002662 | 0.147631 |
| NAA30 | ENSG00000139977 | −0.341182009 | down | 0.002662 | 0.147631 |
| NBEA | ENSG00000172915 | 1.297503689 | up | 0.005124 | 0.182007 |
| NCAPH | ENSG00000121152 | −1.60849361 | down | 0.005379 | 0.185044 |
| NDFIP1 | ENSG00000131507 | 0.620791298 | up | 0.000202 | 0.090927 |
| NDUFA3 | ENSG00000170906 | 0.577079384 | up | 0.002662 | 0.147631 |
| NEDD4L | ENSG00000049759 | 1.124026207 | up | 0.001247 | 0.125963 |
| NOL12 | ENSG00000256872 | −0.5896443 | down | 0.00046 | 0.097757 |
| NPRL3 | ENSG00000103148 | −0.392961317 | down | 0.00046 | 0.097757 |
| NR1D2 | ENSG00000174738 | 0.455919632 | up | 0.003622 | 0.165504 |
| NR3C1 | ENSG00000113580 | 0.731585314 | up | 0.005124 | 0.182007 |
| NSUN5 | ENSG00000130305 | −0.478595971 | down | 0.00488 | 0.180898 |
| NUDT1 | ENSG00000106268 | −0.852740182 | down | 0.000155 | 0.090927 |
| NUF2 | ENSG00000143228 | −1.103956787 | down | 0.001558 | 0.125963 |
| NXPE4 | ENSG00000137634 | 4.468868564 | up | 0.003745 | 0.167074 |
| OIP5 | ENSG00000104147 | −1.202560379 | down | 0.00488 | 0.180898 |
| ORC1 | ENSG00000085840 | −1.065526966 | down | 0.001835 | 0.1271 |
| P4HTM | ENSG00000178467 | 0.696412296 | up | 0.003272 | 0.160028 |
| PAIP2B | ENSG00000124374 | 0.608423558 | up | 0.003443 | 0.164705 |
| PAM | ENSG00000145730 | 0.736380555 | up | 0.001835 | 0.1271 |
| PAQR4 | ENSG00000162073 | −1.249506432 | down | 0.000316 | 0.09315 |
| PARL | ENSG00000175193 | 0.385732857 | up | 0.000519 | 0.103273 |
| PARPBP | ENSG00000185480 | −1.127390341 | down | 0.001319 | 0.125963 |
| PATZ1 | ENSG00000100105 | −0.613716272 | down | 0.002044 | 0.13169 |
| PC | ENSG00000173599 | −2.196281547 | down | 0.001835 | 0.1271 |
| PCBP3 | ENSG00000183570 | 1.620969616 | up | 0.001558 | 0.125963 |
| PCBP4 | ENSG00000090097 | 1.027008279 | up | 1.76E−05 | 0.067115 |
| PCDHB10 | ENSG00000120324 | 1.367015984 | up | 0.002959 | 0.154081 |
| PCDHB16 | ENSG00000196963 | 2.272079546 | up | 0.001461 | 0.125963 |
| PCDHB9 | ENSG00000177839 | 1.659119974 | up | 0.000156 | 0.090927 |
| PCDHGA10 | ENSG00000253846 | 1.761871736 | up | 0.001852 | 0.12771 |
| PCYT1A | ENSG00000161217 | 0.388019625 | up | 0.006514 | 0.199433 |
| PDCD1LG2 | ENSG00000197646 | 1.007150591 | up | 0.005645 | 0.190341 |
| PDE6G | ENSG00000185527 | −2.06520501 | down | 0.001474 | 0.125963 |
| PDE8A | ENSG00000073417 | 0.898071797 | up | 0.000661 | 0.106442 |
| PDIA3 | ENSG00000167004 | 0.599823335 | up | 8.96E−05 | 0.090927 |
| PDXDC2P | ENSG00000196696 | 0.390023823 | up | 0.002156 | 0.135243 |
| PDZK1IP1 | ENSG00000162366 | 2.059953642 | up | 0.005845 | 0.194138 |
| PFN2 | ENSG00000070087 | 1.726786978 | up | 0.002804 | 0.149035 |
| PGP | ENSG00000184207 | −0.394712174 | down | 0.001738 | 0.1271 |
| PHF19 | ENSG00000119403 | −0.59874177 | down | 0.000432 | 0.097757 |
| PKMYT1 | ENSG00000127564 | −1.403609452 | down | 0.001937 | 0.129464 |
| PLCB4 | ENSG00000101333 | 1.358514715 | up | 0.006212 | 0.196883 |
| PLK1 | ENSG00000166851 | −0.980915772 | down | 0.002804 | 0.149035 |
| PLK4 | ENSG00000142731 | −0.863342434 | down | 0.000215 | 0.090927 |
| POLA2 | ENSG00000014138 | −0.356587586 | down | 0.005645 | 0.190341 |
| POLD3 | ENSG00000077514 | −0.649754527 | down | 3.02E−05 | 0.067115 |
| PON2 | ENSG00000105854 | 1.064018977 | up | 3.25E−05 | 0.067115 |
| POPDC2 | ENSG00000121577 | 0.507108724 | up | 0.004647 | 0.179635 |
| POU2F2 | ENSG00000028277 | 0.829755089 | up | 0.001319 | 0.125963 |
| PPFIBP2 | ENSG00000166387 | 0.701578337 | up | 0.004209 | 0.174124 |
| PPIB | ENSG00000166794 | 0.480516293 | up | 0.002804 | 0.149035 |
| PPID | ENSG00000171497 | −0.266755933 | down | 0.002804 | 0.149035 |
| PPIP5K1 | ENSG00000168781 | 0.808884722 | up | 0.000939 | 0.11973 |
| PPP1R16B | ENSG00000101445 | −1.201260806 | down | 0.003809 | 0.167074 |
| PRIM1 | ENSG00000198056 | −0.995746296 | down | 0.000297 | 0.092779 |
| PRKAA1 | ENSG00000132356 | 0.401998563 | up | 0.001738 | 0.1271 |
| PRKAR1B | ENSG00000188191 | −0.660679976 | down | 0.002397 | 0.140035 |
| PRKCA | ENSG00000154229 | 1.369576279 | up | 0.001474 | 0.125963 |
| PSENEN | ENSG00000205155 | 0.368704282 | up | 0.002662 | 0.147631 |
| PTHLH | ENSG00000087494 | 2.864363043 | up | 0.000427 | 0.097757 |
| PTPRM | ENSG00000173482 | 1.799116837 | up | 0.003443 | 0.164705 |
| RAB3B | ENSG00000169213 | 1.817774395 | up | 0.005124 | 0.182007 |
| RABAC1 | ENSG00000105404 | 0.682722137 | up | 0.004005 | 0.170476 |
| RAC3 | ENSG00000169750 | −0.783424905 | down | 0.00488 | 0.180898 |
| RAD18 | ENSG00000070950 | −0.388012916 | down | 0.005922 | 0.194138 |
| RAD51B | ENSG00000182185 | −0.647226192 | down | 0.004866 | 0.180898 |
| RAPGEF3 | ENSG00000079337 | 1.460778486 | up | 0.001835 | 0.1271 |
| RASGRP3 | ENSG00000152689 | 1.361593186 | up | 0.000886 | 0.118955 |

TABLE 4-continued

| HUGO Gene Symbol | Ensembl Gene Name | log2 (R/NR) | Δ gene expression level | P-value | Q-value |
|---|---|---|---|---|---|
| RBBP8 | ENSG00000101773 | −0.420670803 | down | 0.006514 | 0.199433 |
| RBKS | ENSG00000171174 | −0.607072797 | down | 0.002273 | 0.138647 |
| RBL1 | ENSG00000080839 | −0.651514248 | down | 0.003109 | 0.157059 |
| RECQL4 | ENSG00000160957 | −1.055176871 | down | 0.002273 | 0.138647 |
| REEP5 | ENSG00000129625 | 0.483198621 | up | 0.00046 | 0.097757 |
| RFC3 | ENSG00000133119 | −0.845003493 | down | 0.005379 | 0.185044 |
| RFC5 | ENSG00000111445 | −0.488787867 | down | 0.002804 | 0.149035 |
| RHOQ | ENSG00000119729 | 0.981684777 | up | 0.001319 | 0.125963 |
| RIC3 | ENSG00000166405 | 2.061495289 | up | 0.000622 | 0.106442 |
| RMDN3 | ENSG00000137824 | 0.687762803 | up | 0.000661 | 0.106442 |
| RMI2 | ENSG00000175643 | −1.105998037 | down | 0.000701 | 0.111769 |
| RNASEH2A | ENSG00000104889 | −0.588788676 | down | 0.003272 | 0.160028 |
| RNF13 | ENSG00000082996 | 0.430500699 | up | 0.000406 | 0.097757 |
| RNF168 | ENSG00000163961 | 0.789370661 | up | 0.001835 | 0.1271 |
| RP11-110I1.12 | ENSG00000255121 | −1.089180897 | down | 0.001053 | 0.125345 |
| RP11-1277A3.1 | ENSG00000247679 | 0.494691737 | up | 0.005124 | 0.182007 |
| RP11-145F16.2 | ENSG00000261050 | 1 | up | 0.001558 | 0.125963 |
| RP11-22P6.3 | ENSG00000260442 | −1.218957746 | down | 0.000305 | 0.09315 |
| RP11-23N2.4 | ENSG00000260609 | 0.599669898 | up | 0.006212 | 0.196883 |
| RP11-295D4.1 | ENSG00000262712 | −0.543310808 | down | 0.004227 | 0.174124 |
| RP11-382J12.1 | ENSG00000246366 | 0.476637496 | up | 0.005645 | 0.190341 |
| RP11-386G11.10 | ENSG00000258017 | −0.732892348 | down | 0.002273 | 0.138647 |
| RP11-417F21.1 | ENSG00000250116 | 0.874469118 | up | 0.002044 | 0.13169 |
| RP11-680G24.5 | ENSG00000260872 | 0.813273679 | up | 0.001646 | 0.125963 |
| RP11-690I21.1 | ENSG00000237641 | 0.982445377 | up | 0.001045 | 0.125345 |
| RP11-81H14.2 | ENSG00000251301 | 1.154574974 | up | 0.002273 | 0.138647 |
| RP1-290I10.6 | ENSG00000229950 | 1.515905482 | up | 0.006057 | 0.196883 |
| RP3-412A9.11 | ENSG00000198832 | 1.332016018 | up | 5.86E−05 | 0.086188 |
| RP4-742C19.8 | ENSG00000233899 | 0.631077104 | up | 0.002526 | 0.144291 |
| RPL7AP10 | ENSG00000240522 | −1.230279468 | down | 0.002679 | 0.148063 |
| RPN1 | ENSG00000163902 | 0.384107056 | up | 0.003622 | 0.165504 |
| RPS11P5 | ENSG00000232888 | 0.666696911 | up | 0.004645 | 0.179635 |
| RSPH3 | ENSG00000130363 | −0.543360762 | down | 0.005922 | 0.194138 |
| RTKN | ENSG00000114993 | 0.84231452 | up | 0.002273 | 0.138647 |
| RTN4IP1 | ENSG00000130347 | −0.635965627 | down | 0.004005 | 0.170766 |
| S100Z | ENSG00000171643 | 1.755116374 | up | 0.000586 | 0.106442 |
| SAPCD1 | ENSG00000228727 | −0.731740287 | down | 0.006514 | 0.199433 |
| SAPCD2 | ENSG00000186193 | −1.176135844 | down | 0.005922 | 0.194138 |
| SASS6 | ENSG00000156876 | −0.232149316 | down | 0.005124 | 0.182007 |
| SBNO1 | ENSG00000139697 | −0.315910334 | down | 0.003622 | 0.165504 |
| SCAMP5 | ENSG00000198794 | 0.861087469 | up | 0.000836 | 0.117391 |
| SDHAP1 | ENSG00000185485 | 0.572219514 | up | 0.000489 | 0.099767 |
| SDHAP3 | ENSG00000185986 | −0.83746263 | down | 0.006514 | 0.199433 |
| SEC13 | ENSG00000157020 | 0.55661178 | up | 0.001053 | 0.125345 |
| SEC22C | ENSG00000093183 | 0.355646837 | up | 0.001738 | 0.1271 |
| SEC61A1 | ENSG00000058262 | 0.610846513 | up | 0.000886 | 0.118955 |
| SEC62 | ENSG00000008952 | 0.788131385 | up | 0.00011 | 0.090927 |
| SELK | ENSG00000113811 | 0.619756413 | up | 0.000432 | 0.097757 |
| SENP2 | ENSG00000163904 | 0.491242791 | up | 0.002273 | 0.138647 |
| SERP1 | ENSG00000120742 | 0.427941701 | up | 0.000886 | 0.118955 |
| SERPINI1 | ENSG00000163536 | 1.401734038 | up | 0.004423 | 0.177259 |
| SGOL1 | ENSG00000129810 | −1.315415063 | down | 0.001179 | 0.125345 |
| SGOL2 | ENSG00000163535 | −1.04754504 | down | 0.005379 | 0.185044 |
| SH3BP5-AS1 | ENSG00000224660 | 0.61664396 | up | 0.000489 | 0.099767 |
| SH3PXD2A | ENSG00000107957 | 0.855689288 | up | 0.000441 | 0.097757 |
| SHCBP1 | ENSG00000171241 | −0.653402279 | down | 0.005379 | 0.185044 |
| SHMT1 | ENSG00000176974 | −0.916266061 | down | 0.005379 | 0.185044 |
| SIT1 | ENSG00000137078 | 1.491042511 | up | 0.003622 | 0.165504 |
| SKA1 | ENSG00000154839 | −1.388698342 | down | 0.002156 | 0.135243 |
| SKA3 | ENSG00000165480 | −1.49596618 | down | 0.001179 | 0.125345 |
| SLAMF1 | ENSG00000117090 | 2.637174504 | up | 0.000552 | 0.1043 |
| SLC22A5 | ENSG00000197375 | 0.364043198 | up | 0.005379 | 0.185044 |
| SLC29A2 | ENSG00000174669 | −2.117487943 | down | 0.003109 | 0.157059 |
| SLC35B1 | ENSG00000121073 | 0.54289746 | up | 0.001558 | 0.125963 |
| SLC35G2 | ENSG00000168917 | 2.36121245 | up | 0.000417 | 0.097757 |
| SLC51A | ENSG00000163959 | 0.619956943 | up | 0.003272 | 0.160028 |
| SLIT1 | ENSG00000187122 | 2.454001823 | up | 0.005971 | 0.195061 |
| SLX4 | ENSG00000188827 | −0.309372634 | down | 0.005922 | 0.194138 |
| SMPD1 | ENSG00000166311 | 0.685554031 | up | 0.003622 | 0.165504 |
| SOGA3 | ENSG00000214338 | 2.141127737 | up | 0.004321 | 0.176822 |
| SOWAHB | ENSG00000186212 | 2.27080955 | up | 0.001624 | 0.125963 |

TABLE 4-continued

| HUGO Gene Symbol | Ensembl Gene Name | log2 (R/NR) | Δ gene expression level | P-value | Q-value |
|---|---|---|---|---|---|
| SOX5 | ENSG00000134532 | 1.658450619 | up | 0.003578 | 0.165504 |
| SRGAP3 | ENSG00000196220 | 1.029665782 | up | 0.000215 | 0.090927 |
| SRI | ENSG00000075142 | 0.37152875 | up | 0.000744 | 0.112803 |
| SSR3 | ENSG00000114850 | 0.4896736 | up | 0.001319 | 0.125963 |
| ST6GAL1 | ENSG00000073849 | 0.766044282 | up | 0.000939 | 0.11973 |
| ST8SIA4 | ENSG00000113532 | 0.850904988 | up | 0.001247 | 0.125963 |
| STARD4 | ENSG00000164211 | 0.367759238 | up | 0.006212 | 0.196883 |
| STARD5 | ENSG00000172345 | 0.709779447 | up | 0.003272 | 0.160028 |
| STIL | ENSG00000123473 | −0.577961832 | down | 0.003622 | 0.165504 |
| STMN1 | ENSG00000117632 | −0.958006821 | down | 0.005124 | 0.182007 |
| TANC2 | ENSG00000170921 | 2.470345102 | up | 0.004645 | 0.179635 |
| TBC1D31 | ENSG00000156787 | −0.55473257 | down | 0.005379 | 0.185044 |
| TBL3 | ENSG00000183751 | −0.371607611 | down | 0.00488 | 0.180898 |
| TCEAL3 | ENSG00000196507 | 1.039621308 | up | 0.000215 | 0.090927 |
| TCF12 | ENSG00000140262 | 0.573433117 | up | 0.003272 | 0.160028 |
| TCHP | ENSG00000139437 | −0.394692495 | down | 0.006212 | 0.196883 |
| TEX19 | ENSG00000182459 | −1.232891533 | down | 0.005548 | 0.189988 |
| TEX30 | ENSG00000151287 | −0.741242721 | down | 0.000997 | 0.125345 |
| TFG | ENSG00000114354 | 0.52087412 | up | 0.004647 | 0.179635 |
| THOC6 | ENSG00000131652 | −0.412866319 | down | 0.000261 | 0.090927 |
| TICAM2 | ENSG00000243414 | 0.757723382 | up | 0.002044 | 0.13169 |
| TIMELESS | ENSG00000111602 | −0.624056848 | down | 0.000661 | 0.106442 |
| TK1 | ENSG00000167900 | −1.120895213 | down | 0.002804 | 0.149035 |
| TMCO6 | ENSG00000113119 | −0.446075861 | down | 0.002662 | 0.147631 |
| TMED7 | ENSG00000134970 | 0.506103886 | up | 0.006514 | 0.199433 |
| TMEM108 | ENSG00000144868 | 1.262393672 | up | 0.005335 | 0.185044 |
| TMEM115 | ENSG00000126062 | 0.360490115 | up | 0.001179 | 0.125345 |
| TMEM150A | ENSG00000168890 | 0.292194 | up | 0.006514 | 0.199433 |
| TMEM243 | ENSG00000135185 | 0.771028169 | up | 0.005379 | 0.185044 |
| TMEM50B | ENSG00000142188 | 0.479584127 | up | 0.003443 | 0.164705 |
| TMEM57 | ENSG00000204178 | 0.382913174 | up | 0.005124 | 0.182007 |
| TMEM63C | ENSG00000165548 | 2.463768871 | up | 0.002526 | 0.144291 |
| TMOD2 | ENSG00000128872 | 1.778485679 | up | 0.006212 | 0.196883 |
| TMPO-AS1 | ENSG00000257167 | −0.726697259 | down | 0.003851 | 0.168443 |
| TPX2 | ENSG00000088325 | −1.221950415 | down | 0.003809 | 0.167074 |
| TRGV5 | ENSG00000211697 | 0.933839652 | up | 0.004528 | 0.179635 |
| TRIM52 | ENSG00000183718 | 0.558151646 | up | 0.004209 | 0.174124 |
| TROAP | ENSG00000135451 | −1.70863633 | down | 0.000297 | 0.092779 |
| TSKU | ENSG00000182704 | 1.51653736 | up | 0.005976 | 0.195061 |
| TSPAN3 | ENSG00000140391 | 0.841070593 | up | 0.002156 | 0.135243 |
| TTC17 | ENSG00000052841 | 0.342525973 | up | 0.003622 | 0.165504 |
| TTK | ENSG00000112742 | −0.988321296 | down | 0.003109 | 0.157059 |
| TTLL5 | ENSG00000119685 | −0.327071817 | down | 0.000406 | 0.097757 |
| TUB | ENSG00000166402 | 1.767676597 | up | 0.002317 | 0.139712 |
| TUBA1B | ENSG00000123416 | −0.538417101 | down | 0.001646 | 0.125963 |
| TXNDC15 | ENSG00000113621 | 0.575328234 | up | 0.003809 | 0.167074 |
| TXNDC5 | ENSG00000239264 | 0.756015355 | up | 0.003443 | 0.164705 |
| TYMS | ENSG00000176890 | −1.081232402 | down | 0.002397 | 0.140035 |
| UBA7 | ENSG00000182179 | 0.856044718 | up | 0.001395 | 0.125963 |
| UBE2C | ENSG00000175063 | −1.269467358 | down | 0.001179 | 0.125345 |
| UBE2E2 | ENSG00000182247 | 0.870140435 | up | 2.40E−05 | 0.067115 |
| UBXN4 | ENSG00000144224 | 0.38181031 | up | 0.006514 | 0.199433 |
| UHRF1 | ENSG00000034063 | −1.469473531 | down | 0.001738 | 0.1271 |
| USP32P3 | ENSG00000189423 | 3.195455286 | up | 0.001473 | 0.125963 |
| VAPB | ENSG00000124164 | −0.257533585 | down | 0.004423 | 0.177259 |
| VIMP | ENSG00000131871 | 0.687773457 | up | 0.003809 | 0.167074 |
| VPS37D | ENSG00000176428 | 1.550120285 | up | 0.005095 | 0.182007 |
| WASL | ENSG00000106299 | 0.492658686 | up | 0.004647 | 0.179635 |
| WBP5 | ENSG00000185222 | 1.50717312 | up | 0.000297 | 0.092779 |
| WDHD1 | ENSG00000198554 | −1.152433926 | down | 0.001632 | 0.125963 |
| WDR62 | ENSG00000075702 | −1.166051204 | down | 0.000245 | 0.090927 |
| WEE1 | ENSG00000166483 | −1.043540913 | down | 0.000359 | 0.097757 |
| XRCC2 | ENSG00000196584 | −0.775604531 | down | 0.005922 | 0.194138 |
| XRCC3 | ENSG00000126215 | −0.655292946 | down | 0.000939 | 0.11973 |
| YIPF2 | ENSG00000130733 | 0.686984318 | up | 0.003109 | 0.157059 |
| ZBTB4 | ENSG00000174282 | 0.59662837 | up | 0.005124 | 0.182007 |
| ZC2HC1A | ENSG00000104427 | 0.629482721 | up | 0.003622 | 0.165504 |
| ZGLP1 | ENSG00000220201 | −0.463720366 | down | 0.005124 | 0.182007 |
| ZHX1-C8ORF76 | ENSG00000259305 | 0.431039293 | up | 0.001835 | 0.1271 |
| ZMAT3 | ENSG00000172667 | 0.647710648 | up | 0.002397 | 0.140035 |
| ZNF101 | ENSG00000181896 | −0.605225083 | down | 0.001474 | 0.125963 |
| ZNF14 | ENSG00000105708 | −0.800698079 | down | 0.002662 | 0.147631 |
| ZNF204P | ENSG00000204789 | 3.260061269 | up | 0.002317 | 0.139712 |
| ZNF358 | ENSG00000198816 | 0.767920473 | up | 0.003109 | 0.157059 |
| ZNF565 | ENSG00000196357 | 0.615820899 | up | 0.005922 | 0.194138 |

TABLE 4-continued

| HUGO Gene Symbol | Ensembl Gene Name | log2 (R/NR) | Δ gene expression level | P-value | Q-value |
|---|---|---|---|---|---|
| ZNF609 | ENSG00000180357 | 0.312449173 | up | 0.001114 | 0.125345 |
| ZNF706 | ENSG00000120963 | 0.465206779 | up | 0.004005 | 0.170766 |
| ZNF738 | ENSG00000172687 | −1.270195442 | down | 0.006256 | 0.197853 |
| ZNF827 | ENSG00000151612 | 0.722894271 | up | 0.006212 | 0.196883 |
| ZNF829 | ENSG00000185869 | −1.490325627 | down | 0.001114 | 0.125345 |
| ZNF852 | ENSG00000178917 | 0.526992277 | up | 0.00488 | 0.180898 |
| ZNF880 | ENSG00000221923 | −2.04089136 | down | 0.004423 | 0.177259 |
| ZNF93 | ENSG00000184635 | −1.691498564 | down | 0.003943 | 0.170766 |
| Not available | ENSG00000233488 | −1.126553625 | down | 1.76E−05 | 0.067115 |
| Not available | ENSG00000259850 | 0.317164674 | up | 0.00488 | 0.180898 |
| Not available | ENSG00000165406 | 0.486776476 | up | 0.000135 | 0.090927 |
| Not available | ENSG00000233165 | 1.051483435 | up | 0.00488 | 0.180898 |
| Not available | ENSG00000266348 | 1.615869627 | up | 0.002819 | 0.149305 |

Log2 (R/NR), gene expression level of responders relative (R) to non-responders (NR). The terms "responder" and "non-responder" used in this example have the same meanings as those in Example 2.
Δ Gene expression level indicates the change in gene expression level of responders (R) relative to non-responders (NR); "up" means that the gene expression level was upregulated in R vs. NR and "down" means that the gene expression level was downregulated in R vs. NR.
Not available, HUGO gene name is not available.

Expression data was determined as essentially described in Example 2. Associations between response and expression of the indicated gene were tested with the Wilcoxon test yielding the P values indicated in Table 4. Q was determined as essentially described in Storey and Tibshirani, "Statistical significance for genome-wide experiments, *Proceedings of the National Academy of Sciences* 100:9440-9445 (2003).

Genes demonstrating strength of association between expression and response to carfilzomib are further analyzed by considering different expression cutoffs. An ROC curve for each gene is made so that each cutoff may be evaluated in terms of % specificity and % sensitivity. The cutoff is then applied to time-to-progression (TTP) data for the patients and clinical relevance is considered.

Example 4: Validation Studies

The analysis of bone marrow samples from carfilzomib (CFZ) Phase 2 clinical studies has shown that high IGH and FCGR2B [0] gene expression levels are predictive of response to the proteasome inhibitor carfilzomib in relapsed and refractory multiple myeloma patients [1]. Bone marrow samples from the carfilzomib Phase 3 clinical studies are analyzed to confirm these analysis results. Additionally, it is determined whether high IGH and FCGR2B gene expression levels are predictive of response to other therapeutic regimens such as corticosteroids plus optional cyclophosphamide (best supportive care; BSC) in patients with relapsed and refractory multiple myeloma and lenalidomide plus dexamethasone (Rd) in patients with multiple myeloma who have received one to three prior lines of therapy.

RNA sequencing data from CD138+ selected bone marrow samples from the carfilzomib Phase 3 clinical studies are analyzed with the goal of confirming that high IGH and/or FCGR2B gene expression levels are predictive of response to the proteasome inhibitor CFZ and not predictive of response to other therapeutic regimens, such as corticosteroids plus optional cyclophosphamide (BSC) and lenalidomide plus dexamethasone (Rd). At the time of patient screening during the trials, bone marrow samples were collected and aspirated. These samples were used to obtain RNA sequencing data. RNA sequencing of these samples are performed at the Translational Genomics Research Institute (TGen).

The RNA samples are divided across the trial arms as follows: There were a total of 192 samples collected as part of the Phase 3 trial from patients treated either with CFZ or according to best supportive care (BSC) that were successfully sequenced. There were 424 samples collected as part of the Phase 3 trial from patients treated either with CFZ, lenalidomide, and dexamethasone (CRd) or with lenalidomide and dexamethasone (Rd) that were successfully sequenced.

Raw sequence reads are aligned and expression of genes and isoforms are quantified with a customized pipeline built in Array Studio v6.1. This pipeline [3] accepts Illumina adapter stripped, paired-end reads that are trimmed at the 5' end if a base reaches PHRED quality score Q2 or lower. All reads are mapped to the transcriptome, as defined by the Ensembl annotation R.70 [4]. Reads mapped with mismatches and unmapped reads are subsequently aligned to the entire human genome, searching for novel exon junctions. Mappings of a particular read pairs to the genome and transcriptome are compared and the highest scoring mapping is kept, with transcriptome mappings preferred in the case of a tie. Reads that remain unmapped at this point are aligned against the newly identified exon junctions. Finally, all transcriptome mapping locations are translated to genomic coordinates to estimate the expected number of mappings using the EM algorithm [5]. The EM algorithm assigns reads with multiple mapping locations to a transcript isoform by calculating the conditional probability of a read mapping to a specific isoform, given all other mappings. Weighting the total number of mapped reads with this probability yields posterior expected read counts for the transcript. The EM counts are normalized by the length of the genes and number of reads in a library to yield FPKM values (Fragments Per Kilobase per Million reads). An additional normalization, referred to as quantile normalization, is applied to correct for biases introduced by the presence of one or two dominant transcripts (e.g., IGH, IGK, & IGL) in many of the samples. In the quantile normalization step each FPKM value in a sample is scaled by the 85th percentile FPKM value of that same sample to yield quantile normalized FPKM, referred to as FPKQ values.

IGH consists of many separately annotated genes in the ENSEMBL annotation. Therefore, estimates of IGH expression are calculated by summing the corresponding FPKQ of each gene of the IGH locus (cf. U.S. Patent No. 61/863,809

'Immunoglobulin Expression Levels as Biomarker for Proteasome Inhibitor', 9/2013, for details). Expression cutoffs for IGH and FCGR2B determined as described above, are employed to quantify enrichment of responders, PFS, and OS on the four clinical trial arms in the biomarker positive versus negative subsets. For this analysis responders are defined as patients achieving a best overall response as determined by the PI of MR, PR, VGPR, or CR and non-responders as SD and PD.

The determined thresholds are then used to select the biomarker positive and negative samples for the biomarker subgroup analysis. In each group, comparison between treatments arms are performed and reported in tables accompanied by survival plots. A Cox regression model including the treatment group is fit and the hazard ratio for the CFZ arm and BSC (Rd) arm and their corresponding 95% confidence intervals are reported. A hazard ratio smaller than 1 implies that an extension of PFS in the CFZ arm compared to the BSC (Rd) arm was observed within the biomarker positive or negative subgroup of patients. The ratio of biomarker positive and biomarker negative hazard ratios are determined to fulfill the key Go criteria. A Wald interaction test is performed and a p-value reported as an indication whether the treatment effect varies according to biomarker status.

Example 5: qPCR

The RNA-Seq analysis of bone marrow samples from carfilzomib (CFZ) Phase 2 clinical studies has shown that high IGH and FCGR2B [0] gene expression levels are predictive of response to the proteasome inhibitor carfilzomib in relapsed and refractory multiple myeloma patients [1]. Bone marrow samples from the carfilzomib Phase 2 and Phase 3 clinical studies are analyzed using an alternative method to confirm these analysis results.

RNA from CD138+ selected bone marrow samples from the carfilzomib Phase 2 and Phase 3 clinical studies are analyzed with the goal of confirming that high IGH and/or FCGR2B gene expression levels can be measured using an RT-qPCR assay and can be used to determine predictiveness of response to the proteasome inhibitor CFZ and non predictiveness of response to other therapeutic regimens, such as corticosteroids plus optional cyclophosphamide (BSC) and lenanlidomide plus dexamethasone (Rd). At the time of patient screening during the trials, bone marrow samples were collected and aspirated.

There were a total of 75 samples collected as part of the Phase 2 study. There were a total of 192 samples collected as part of the Phase 3 trial from patients treated either with CFZ or according to best supportive care (BSC). There were 424 samples collected as part of the Phase 3 trial from patients treated either with CFZ, lenalidomide, and dexamethasone (CRd) or with lenalidomide and dexamethasone (Rd).

First, reverse transcription of RNA previously used for RNA-Seq data is performed. Then RT-qPCR (quantitative polymerase chain reaction) [2][3] is performed to determine the amount of Ig and/or FCGR2B in a sample by measuring the threshold cycle (Ct) or crossing point value. The Ct reflects the cycle at which the measured signal exceeds a defined background threshold. The flourescence signal is measured at the end of each amplification cycle and the Ct value results from the interpolation of the two signal measurements between which the threshold was crossed [2]. Negative specimens do not yield a Ct value. The quantitative Ct value is negatively associated with the (log) concentration of nucleic acids detected, i.e. the higher the Ct value the lower the input concentration.

Targeted primers are used to amplify the IgH locus and/or the FCGR2B gene of each sample. The expression levels of these two targets are normalized using house-keeping genes. A correlation between Ig and/or FCGR2B expression levels as measured using the RNA-Seq data (cf. Example 4) and as measured using the RT-qPCR method is established. RT-qPCR being representative of the amount of Ig and/or FCGR2B in a patient sample is validated. A pilot study performed on 19 samples from the Phase 3 trials has shown a good correlation ($R^2=0.919$) between RNA-Seq and RT-qPCR expression leves of the FCGR2B gene.

After this correlation is established for the Ig locus, an optimal cutoff to distinguish between responders and non-responders is determined by calculating sensitivity and specificity for all possible cut-off combinations within the range of the assay. An ROC analogous to the method described above is used to find an optimal cutoff to enrich for responders in the data.

The determined thresholds are then used to select the biomarker positive and negative samples for the biomarker subgroup analysis. In each group, comparisons between treatments arms are performed and reported in tables accompanied by survival plots. A Cox regression model including the treatment group is fitted and the hazard ratio for the CFZ arm and BSC (Rd) arm and their corresponding 95% confidence intervals are reported. A hazard ratio smaller than 1 implies that an extension of PFS in the CFZ arm compared to the BSC (Rd) arm was observed within the biomarker positive or negative subgroup of patients. A Wald interaction test is performed and a p-value reported as an indication whether the treatment effect varies according to biomarker status.

Example 6: Immunofluorescence Assay

An immunofluorescence (IF) based assay [2] is used to quantify the amount of Ig and/or FCGR2B protein in a sample. The IF technique comprises of two phases: (1) slide preparation (specimen fixation and permeabilization) and immunoreaction (in order: antigen retrieval, non-specific site block, primary antibody incubation, secondary incubation, couterstaining with a nuclear dye, and mounting the slide); (2) employment of systems of detection, interpretation and quantification of the obtained expression. As part of the clinical Phase 2 and 3 trials, cyto spin slides of bone marrow aspirates were prepared from each sample. To visually confirm the presence of plasma cells, a CD138+ antibody was used to stain the sample. Specific antibodies against Ig and/or FCGR2B antigens that can also be visualized by staining are employed. The amount of staining is quantified using a flourescence microscope and standard image processing tools.

A correlation between Ig and/or FCGR2B expression levels as measured using the RNA-Seq data (cf. Example 4) and as measured using the IF method is establised. The IF assay being representative of the amount of Ig and/or FCGR2B in a patient sample is validated.

After this correlation is established, an optimal cutoff to distinguish between responders and non-responders is determined by calculating sensitivity and specificity for all possible cut-off combinations within the range of the assay. An ROC analogous to the method described above is used to find an optimal cutoff to enrich for responders in our data.

The determined thresholds are then used to select the biomarker positive and negative samples for the biomarker subgroup analysis. In each group, comparison between treatments arms are performed and reported in tables accompanied by survival plots. A Cox regression model including the treatment group is fitted and the hazard ratio for the CFZ arm and BSC (Rd) arm and their corresponding 95% confidence intervals are reported. A hazard ratio smaller than 1 implies that an extension of PFS in the CFZ arm compared to the BSC (Rd) arm was observed within the biomarker positive or negative subgroup of patients. A Wald interaction test is performed and a p-value reported as an indication whether the treatment effect varies according to biomarker status.

Example 7: Validation

This example demonstrates that sensitivity to carfilzomib correlates with level of expression of immunoglobulin.

Figure 11A:
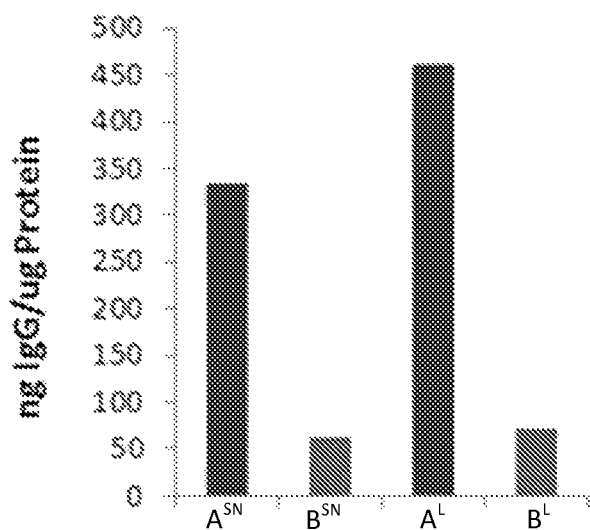
FIG. 11A is a graph of the immunoglobulin expression (ng IgG protein per μg total cellular protein) by cells of Line A or Line B, as measured by ELISA. SN, supernatant of cell culture; L, cell lysate.

Two hybridoma cell lines, Line A and Line B, were tested for immunoglobulin (Ig) gene expression levels by ELISA assay. Either hybridoma cell culture supernatant or hybridoma cell lysates were added to wells containing antibody specific for mouse IgG (Cat. No. E99-131; Lot No. E99-131-130419 Bethyl Laboratories Inc). As shown in FIG. 11A, hybridoma cells of Line A expressed Ig to a greater extent, relative to the Ig expression levels exhibited by Line B. Line A accordingly was considered as a high Ig-expressing (high Ig) hybridoma cell line, and Line B was considered a low Ig-expressing (low Ig) hybridoma cell lines.

Figure 11B:
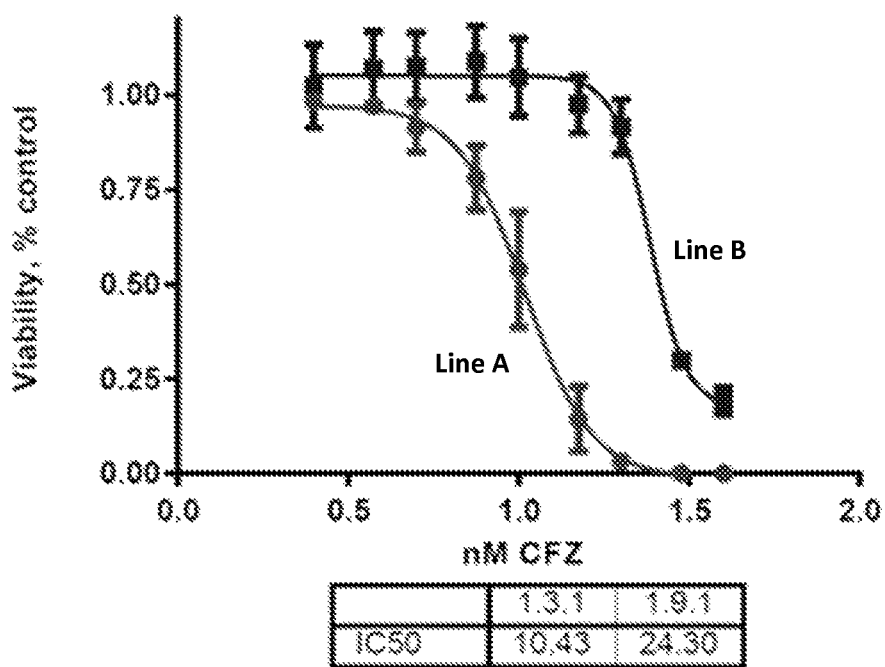
FIG. 11B is a graph of the viability of cells of Line A and Line B upon treatment with carfilzomib (CFZ). Viability is expressed as % viable cells relative to untreated control.

The two hybridoma cell lines were tested for sensitivity to carfilzomib. Cells of each of Line A (high Ig) and Line B (low Ig) were treated with various doses (40 nM, 30 nM, 20 nM, 15 nM, 10 nM, 7.5 nM, 5 nM, 3.75 nM and 2.5 nM) of carfilzomib for 72h. The viability of the cells were then measured by CellTiter-Glo® Luminescent Cell Viability Assay (Cat. No. G7570; Promega Corporation) and compared to no treatment control. As shown in FIG. 11B, cells of Line A were more sensitive to carfilzomib, relative to cells of Line B. The inhibitory concentration (IC50) of carfilzomib on the cells of Line A was 10.43 nM, whereas the IC50 of carfilzomib on the cells of Line B was 24.30.

The drug sensitivity assay performed on two additional pairs of hybridoma cell lines, each pair consisted of a high and a low Ig-expressing hybridoma cell line produced similar results to those achieved with Line A and Line B. For each pair, the cells of the high Ig-expressing hybridoma cell lines demonstrated a greater sensitivity to carfilzomib, relative to the cells of the low Ig-expressing lines.

Example 8: Quantitative RT-PCR

Taqman primers and probes for PCR amplification of FCGR2B was purchased from Life Technologies (Cat#4331182).

CD138 positive cells were collected from bone-marrow aspirates obtained from patients. Total RNA was then isolated from these cells using Trizol reagent (Cat.#15596-026; Life Technologies). The cDNAs were made using QuantiTect Reverse Transcription kit from Qiagen (Cat.#205310) and qRT-PCR assays were performed using Taqman assay reagents (Cat.#4440042; Life Technologies).

Figure 12:
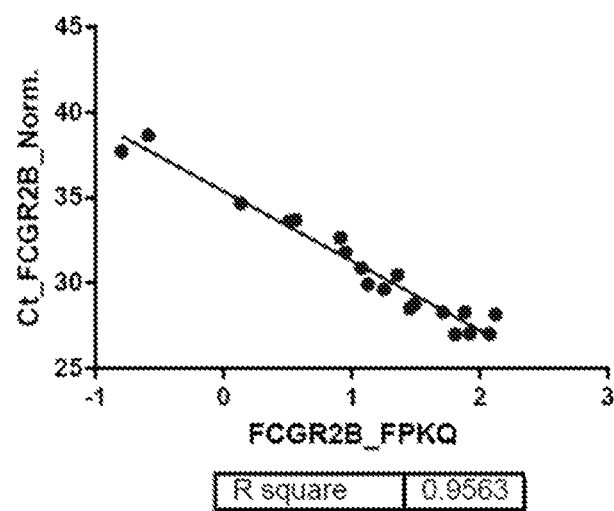
FIG. 12 is a graph of the amount of FCGR2B RNA as measured by qPCR. The FCGR2B RNA amount is expressed as normalized threshold cycle (Ct).

As shown in FIG. 12, the amplification and quantification of the expression of FCGR2B using the above primer pairs were successful. A strong correlation between RNA Seq data (FPKQ) and qRT-PCR data ($R^2$=0.9563) indicate that the Taqman assay can be reliably used to determine FCGR2B transcript level from patient samples. Development of similar assays for IGH genes are in progress.

Once the assays are developed patient samples from a Phase II clinical trial will be subjected to the same quantitative RT-PCR measurements to establish a qRT-PCR based cut-off that will separate the responders from the non-responders.

Patient samples from a Phase III clinical trial will then be subjected to the same qRT-PCR assays and the cut-off established from Phase II study will be applied to parse responder from non-responder.

REFERENCES

References Cited in Examples 1 and 2

Dempster, A. P.; Laird, N. M., Rubin, D. B. (1977). Maximum Likelihood from Incomplete Data via the EM Algorithm. Journal of the Royal Statistical Society, Series B 39 (1): 1-38

Jun Hu, Huanying Ge, Matt Newman and Kejun Liu. OSA: a fast and accurate alignment tool for RNA-Seq. Bioinformatics (2012) 28 (14): 1933-1934.

Mulligan G, Mitsiades C, Bryant B, Zhan F, Chng W J, Roels S, Koenig E, Fergus A, Huang Y, Richardson P, Trepicchio W L, Broyl A, Sonneveld P, Shaughnessy J D Jr, Bergsagel P L, Schenkein D, Esseltine D L, Boral A, Anderson K C. Gene expression profiling and correlation with outcome in clinical trials of the proteasome inhibitor bortezomib. Blood. 2007 Apr. 15; 109(8):3177-88.

Rody A, Holtrich U, Pusztai L, Liedtke C, Gaetje R, Ruckhaeberle E, Solbach C, Hanker L, Ahr A, Metzler D, Engels K, Karn T, Kaufmann M. T-cell metagene predicts a favorable prognosis in estrogen receptor-negative and HER2-positive breast cancers. Breast Cancer Res. 2009; 11(2):R15.

References Cited in Example 4

[0] Gray, K. A., Daugherty, L. C., Gordon, S. M., Seal, R. L., Wright, M. W., Bruford, E. A. 'genenames.org: the HGNC resources in 2013'
Nucleic Acids Res. 2013 January; 41(Database issue):D545-52. doi: 10.1093/nar/gks1066. Epub 2012 Nov. 17 PMID: 23161694

[1] Tuch, B. B., Löhr, A., Degenhardt, J. D., Kwei, K. A., Lowe, E., Keats, J. J., Kirk, C. J.
U.S. Patent No. 61/863,809 'Immunoglobulin Expression Levels as Biomarker for Proteasome Inhibitor', September 2013

[2] Robert Hajek, Richard Vryce, Sunhee Ro, Barbara Klencke, Heinz Ludwig
'Design and rationale of FOCUS(PX-171-011): A randomized, open-label, phase 3 study of carfolzomib versus best supportive care regimen in patients with relapsed and refractory multiple myeloma' BMC Cancer 2012, 12:415

[3] Jun Hu, Huanying Ge, Matt Newman and Kejun Liu
'OSA: a fast and accurate alignment tool for RNA-Seq' Bioinformatics (2012) 28 (14): 1933-1934.

[4] Paul Flicek, Ikhlak Ahmed, M. Ridwan Amode, Daniel Barrell, Kathryn Beal, Simon Brent, Denise Carvalho-Silva, Peter Clapham, Guy Coates, Susan Fairley, Stephen Fitzgerald, Laurent Gil, Carlos Garcia-Giron, Leo Gordon, Thibaut Hourlier, Sarah Hunt, Thomas Juettemann, Andreas Kahari, Stephen Keenan, Monika Komorowska, Eugene Kulesha, Ian Longden, Thomas Maurel, William McLaren, Mattieu Muffato, Rishi Nag, Bert Overduin, Miguel Pignatelli, Bethan Pritchard, Emily Pritchard, Harpreet Singh Riat, Graham R. S. Ritchie, Magali Ruffier, Michael Schuster, Daniel Sheppard, Daniel Sobral, Kieron Taylor, Anja Thormann, Stephen Trevanion, Simon White, Steven P. Wilder, Bronwen L. Aken, Ewan Birney, Fiona Cunningham, Ian Dunham, Jennifer Harrow, Javier Herrero, Tim J. P. Hubbard, Nathan Johnson, Rhoda Kinsella, Anne Parker, Giulietta Spudich, Andy Yates, Amonida Zadissa and Stephen M. J. Searle 'Ensembl 2013' Nucleic Acids Research 2013 41 Database issue:D48-D55

[5] Dempster, A. P.; Laird, N. M., Rubin, D. B. (1977) 'Maximum Likelihood from Incomplete Data via the EM Algorithm' Journal of the Royal Statistical Society, Series B 39 (1): 1-38

[6] Soreide, K. (2009) 'Receiver-operating characteristic curve analysis in diagnostic, prognostic and predictive biomarker research', Journal of Clinical Pathology 62:1-5

[7] Jiang, W., Freidlin, B., Simon, R. (2007) 'Biomarker-adaptive threshold design: a procedure for evaluating treatment with possible biomarker-defined subset effect' Journal of the National Cancer Institute 99(13):1036-43

References Cited in Example 5

[0] Gray, K. A., Daugherty, L. C., Gordon, S. M., Seal, R. L., Wright, M. W., Bruford, E. A. 'genenames.org: the HGNC resources in 2013' Nucleic Acids Res. 2013 January; 41(Database issue):D545-52. doi: 10.1093/nar/gks1066. Epub 2012 Nov. 17 PMID: 23161694

[1] Tuch, B. B., Löhr, A., Degenhardt, J. D., Kwei, K. A., Lowe, E., Keats, J. J., Kirk, C. J.
U.S. Patent No. 61/863,809 'Immunoglobulin Expression Levels as Biomarker for Proteasome Inhibitor', September 2013

[2] Caraguel, C. G. B., Stryhn, H., Gagne, N., Dohoo, I. R., Hammell, K. L., "Selecting a Cutoff Value for Real-Time Polymerase Chain Reaction Results to Fit a Diasgnostic Purpose", J VET Diagn Invest 2011, 32:2

[3] Mackay I M, Arden K E, Nitsche A: 2002, "Real-time PCR in virology". Nucleic Acids Res 30:1292-1305.

References Cited in Example 6

[0] Gray, K. A., Daugherty, L. C., Gordon, S. M., Seal, R. L., Wright, M. W., Bruford, E. A. 'genenames.org: the HGNC resources in 2013' Nucleic Acids Res. 2013 January; 41(Database issue):D545-52. doi: 10.1093/nar/gks1066. Epub 2012 Nov. 17 PMID: 23161694

[1] Tuch, B. B., Löhr, A., Degenhardt, J. D., Kwei, K. A., Lowe, E., Keats, J. J., Kirk, C. J.
U.S. Patent No. 61/863,809 'Immunoglobulin Expression Levels as Biomarker for Proteasome Inhibitor', September 2013

[2] Odell, I. D., Cook D., 'Immunofluorescence Techniques', J of Investig. Dermatology, 2013, 133 e4

A number of embodiments of the invention have been described. Nevertheless, it will be understood that various modifications may be made without departing from the spirit and scope of the invention. Accordingly, other embodiments are within the scope of the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10870889B2). An electronic copy of the "Sequence Listing" will also be available from the USPTO upon request and payment of the fee set forth in 37 CFR 1.19(b)(3).

What is claimed is:

1. A method for treating a tumor in a subject, said method comprising (i) determining the subject as responsive to treatment with a proteasome inhibitor by (a) obtaining a sample from the subject, wherein the sample comprises a cell from the tumor, (b) measuring the level of expression of Fc gamma receptor 2B (FCGR2B) in the sample and (c) determining the subject as responsive to treatment with a proteasome inhibitor when the level of expression of FCGR2B of the sample is greater than or equal to an FPKQ cutoff of 75 and (ii) administering to the subject an effective amount of a proteasome inhibitor.

2. The method of claim 1, wherein the proteasome inhibitor is carfilzomib, bortezomib, or oprozomib.

3. The method of claim 1, wherein the tumor is a hematological tumor.

4. The method of claim 2, wherein the proteasome inhibitor is bortezomib.

5. The method of claim 3, wherein the hematological tumor is a multiple myeloma.

6. The method of claim 1, comprising measuring the level of expression of FCGR2B in CD138-positive tumor cells obtained from the subject.

7. The method of claim 1, comprising extracting RNA from CD138-positive tumor cells.

8. The method of claim 1, wherein the sample comprises CD138-positive tumor cells isolated from bone marrow cells.

9. The method of claim 1, wherein
the subject (i) has previously been treated for multiple myeloma or (ii) has previously been diagnosed with multiple myeloma or (iii) is a human patient having or suspected of having multiple myeloma, refractory multiple myeloma, or relapsed multiple myeloma.

10. The method of claim 1, wherein the method comprises use of a kit comprising one or more binding agents to FCGR2B gene or gene product.

11. The method of claim 2, wherein the proteasome inhibitor is carfilzomib.

12. The method of claim 5, wherein the multiple myeloma is relapsed multiple myeloma or refractory multiple myeloma.

13. The method of claim 1, wherein the proteasome inhibitor is disulfiram.

* * * * *